United States Patent
Lienkamp et al.

(10) Patent No.: US 10,889,726 B2
(45) Date of Patent: Jan. 12, 2021

(54) POLYMER HAVING ANTIMICROBIAL AND/OR ANTIFOULING PROPERTIES

(71) Applicant: ALBERT-LUDWIGS-UNIVERSITÄT FREIBURG, Freiburg (DE)

(72) Inventors: Karen Lienkamp, Gundelfingen (DE); David Boschert, Gundelfingen (DE); Alexandra Schneider - Chaabane, Freiburg (DE); Ali Al-Ahmad, Freiburg (DE)

(73) Assignee: ALBERT-LUDWIGS-UNIVERSITÄT FREIBURG, Freiburg (DE)

(*) Notice: Subject to any disclaimer, the term of this patent is extended or adjusted under 35 U.S.C. 154(b) by 216 days.

(21) Appl. No.: 15/776,101

(22) PCT Filed: Nov. 15, 2016

(86) PCT No.: PCT/EP2016/077756
§ 371 (c)(1),
(2) Date: May 15, 2018

(87) PCT Pub. No.: WO2017/085069
PCT Pub. Date: May 26, 2017

(65) Prior Publication Data
US 2018/0327607 A1  Nov. 15, 2018

(30) Foreign Application Priority Data

Nov. 18, 2015 (DE) .......... 10 2015 120 009
Nov. 18, 2015 (DE) .......... 10 2015 120 010

(51) Int. Cl.
| | |
|---|---|
| *C08F 8/12* | (2006.01) |
| *A61L 2/00* | (2006.01) |
| *A61L 31/10* | (2006.01) |
| *A61L 27/34* | (2006.01) |
| *C09D 5/16* | (2006.01) |
| *A61L 29/08* | (2006.01) |
| *C08F 220/54* | (2006.01) |
| *C08F 222/22* | (2006.01) |
| *C08F 22/22* | (2006.01) |

(52) U.S. Cl.
CPC .............. *C09D 5/1637* (2013.01); *A61L 2/00* (2013.01); *A61L 27/34* (2013.01); *A61L 29/085* (2013.01); *A61L 31/10* (2013.01); *C08F 8/12* (2013.01); *C08F 22/22* (2013.01); *C08F 220/54* (2013.01); *C08F 222/22* (2013.01); *C09D 5/1668* (2013.01); *A61L 2300/404* (2013.01); *A61L 2420/02* (2013.01); *C08F 2810/50* (2013.01)

(58) Field of Classification Search
None
See application file for complete search history.

(56) References Cited

U.S. PATENT DOCUMENTS

| | | | |
|---|---|---|---|
| 5,208,016 A | 5/1993 | Ohmae et al. | |
| 2006/0024264 A1* | 2/2006 | Kuroda | ............... A61K 31/765 424/78.3 |
| 2010/0317870 A1* | 12/2010 | Tew | ..................... C07D 225/06 548/453 |

FOREIGN PATENT DOCUMENTS

| | | | |
|---|---|---|---|
| CA | 2763773 A1 | * | 12/2010 |
| EP | 2 636 693 A1 | | 9/2013 |
| JP | 2000-007505 A | | 1/2000 |

OTHER PUBLICATIONS

International Search Report & Written Opinion dated Jan. 31, 2017 corresponding to International Patent Application No. PCT/EP2016/077756.
International Preliminary Report with the Written Opinion International Application No. PCT/EP2016/077756 dated May 22, 2018.

* cited by examiner

*Primary Examiner* — Sheeba Ahmed
(74) *Attorney, Agent, or Firm* — Squire Patton Boggs (US) LLP

(57) ABSTRACT

The present invention provides a polymer having antimicrobial and/or antifouling (protein-repellent) properties, a monomer that can be used in a method of producing the polymer of the invention, and a use of the polymer of the invention, including a method for coating the surface of a material, substrate or product with the polymer of the invention, as well as to products comprising the polymer of the invention and/or a coating comprising the polymer of the invention.

36 Claims, 2 Drawing Sheets

POLYMER HAVING ANTIMICROBIAL AND/OR ANTIFOULING PROPERTIES

The present invention relates to a polymer having antimicrobial and/or antifouling (protein-resistant) properties, to monomers that can be used in a method of producing the polymer of the invention, and to a use of the polymer of the invention, including a method for coating the surface of a material, substrate or product with the polymer of the invention, as well as to products comprising the polymer of the invention and/or to a coating comprising the polymer of the invention.

PRIOR ART

Since the discovery of penicillin by Fleming in 1928, antibiotics have gained an ever increasing importance in the fight against infectious diseases caused by bacteria. The first antibiotic was tested 1941 with human patients. Soon, antibiotics became the regular treatment even for minor infections. This led to the formation of resistance against antibiotics among an ever increasing number of bacterial strains, causing massive problems in public institutions such as hospitals, schools and homes for the elderly, where bacteria can easily spread. In 2011, there were about 25 000 deaths that could be clearly related to bacterial infections in the European Union, and the number of annual deaths in the USA is estimated to about 100 000. At the same time, only few new antibiotic substance classes have been developed in the last decades, and those that were had severe side effects. Novel antibiotic substances, particularly such that do not cause antibiotic resistance, are thus direly needed.

Synthetic mimics of antimicrobial peptides (SMAMPs) could meet this need. SMAMPs are molecules that imitate the properties of antimicrobial peptides (AMPs), a class of compounds that are part of the immune system of multicellular organisms. AMPs are facially amphiphilic molecules that are able to selectively attack bacteria, but not mammalian cells. While antibiotics have defined cell targets, typically receptors, AMPs act unspecifically and use the physical properties of the cell to operate. With their hydrophilic, cationic groups, they attach to the outer envelope of negatively charged bacterial cells. They then cluster and insert their hydrophobic groups through the lipid bilayer of the bacterial membrane. This causes either pore formation or rupture of the bacteria, associated with leakage of cytoplasm and cell death or at least bacteriostasis. Because of this unspecific mode of action, so far there are only very few reports of bacterial resistance against AMPs. These involve changes of the chemistry and/or charge of the bacterial envelope; however, these AMP-resistant bacteria could so far not prevail in the evolutionary competition with non-resistant strains. Considering the time-span of evolution, the resistance rate against AMPs is thus negligible, compared to today's resistance rates against antibiotics.

Several families of synthetic mimics of antimicrobial peptides that imitate the properties and mechanism of action of AMPs have been reported so far: for example, Tew and Lienkamp reported poly(oxonorbornene) based SMAMPs (cf. e.g. Lienkamp et al., J. Am. Chem. Soc. 2008, 130(30), 9836); Kuroda and Degrado reported methacrylate based SMAMPs (cf. e.g. Kuroda, K.; DeGrado, W. F., J. Am. Chem. Soc. 2005, 127(12), 4128); and Gellman and coworkers reported nylon-3 based SMAMPs (cf. e.g. Mowery et al., J. Am. Chem. Soc. 2007, 129(50), 15474). Each of these systems has strong features, such as high antimicrobial activity; however, there are also substantial drawbacks. For example, while some of the poly(oxonornornene) SMAMPs consists of facially amphiphilic repeat units, which is crucial to achieve cell selectivity, they require a metal catalyst for their synthesis that may be difficult to remove, and some of these SMAMPs undergo hydrolysis under physiological conditions that limits their applications. The methacrylate SMAMPs do not require a metal catalyst but can be obtained by simple free radical polymerization; however, they consist of hydrophobic and hydrophilic co-repeat units instead of amphiphilic monomers. This causes hydrophobic domains in the polymer chain, which mediates cell toxicity towards mammalian cells and severely limits the cell selectivity of these polymers. The nylon-3 polymers also consist of co-repeat units, but thanks to their generally more hydrophilic backbone the cell selectivity is not as adversely affected as the methacrylates. Their precursors, however, are difficult to synthesize (cf. e.g. Lee et al., J. Am. Chem. Soc. 2009, 131(46), 16779). Additionally, all of the above examples rely on polymers that are mainly obtained from fossil fuels.

Several studies have shown that SMAMPs operate in a similar way as AMPs (cf. e.g. Al-Ahmad et al., PLoS One 2013, 8(9), e73812, A. E. Madkour, A. H. R. Koch, K. Lienkamp, G. N. Tew, *Macromolecules* 2010, 43, 4557-4561), thus it is clear that these substances are promising materials in the fight against multiresistant bacteria if the drawbacks that limit their application can be solved.

Further information on SMAMPs is published in: K. Lienkamp, G. N. Tew, *Chemistry—A European Journal* 2009, 15, 11784-11800; K. Lienkamp, A. E. Madkour, G. N. Tew, *Advances in Polymer Science* 2013, 251, 141-172; W. Hu, A. Som, G. N. Tew, *J. Phys. Chem. B* 2011, 115, 8474-8480; G. N. Tew, R. W. Scott, M. L. Klein, W. F. De Grado, *Acc. Chem. Res.* 2010, 43, 30-39; A. Som, S. Vemparala, I. Ivanov, G. N. Tew, *Biopolymers* 2008, 90, 83-93; R. W. Scott, W. F. DeGrado, G. N. Tew, *Curr. Opin. Biotechnol.* 2008, 19, 620-627; G. J. Gabriel, J. G. Pool, A. Som, J. M. Dabkowski, E. B. Coughlin, M. Muthukumar, G. N. Tew, *Langmuir* 2008, 24, 12489-12495; L. Yang, V. D. Gordon, A. Mishra, A. Som, K. R. Purdy, M. A. Davis, G. N. Tew, G. C. L. Wong, *Journal of the American Chemical Society* 2007, 129, 12141-12147; and G. J. Gabriel, A. Som, A. E. Madkour, T. Eren, G. N. Tew, *Mater. Sci. Eng., R* 2007, R57, 28-64.

Problem to be Solved by the Present Invention

In view of the above problems associated with the SMAMPs of the prior art, there is a continuous need for novel polymer-based synthetic mimics of antimicrobial peptides (SMAMPs) that (a) are stable under physiological conditions and typical conditions for biomedical applications (medication formulations, surfaces coatings, sterilization conditions, storage conditions); (b) consists of facially amphiphilic repeat units to enable fine-tuning of the biological properties of the resulting polymer, so that cell toxicity can be avoided; (c) can be polymerized by standard polymerization methods using a non-toxic, preferentially non-metal based polymerization initiator that remains covalently attached to the polymer chain and thus does not have to be removed from the polymer by laborious workup; (d) are based on a flexible synthetic platform and can be obtained in a few easy synthetic steps; and (e) are preferentially obtained from components that are available from renewable resources.

Advantageously, the new SMAMPs should be based on a source independent of mineral oil. Moreover, it should be possible to prepare the new SMAMPs without the need for reagents, which are too hazardous, toxic, or the like, in order to avoid a contamination of the SMAMPs, e.g. by (heavy) metals, or the like. Moreover, the new SMAMP should be producible in a cost-efficient manner and allow for industrial production. Advantageously, the new SMAMPs should allow the coating of a surface, e.g., of a material, substrate or product, in order to provide said material, substrate or product with a surface having antimicrobial and/or antifouling (protein-repellant) properties.

Thus, it is an object of the present invention to provide a novel polymer-based synthetic mimic of antimicrobial peptides (SMAMPs), which fulfills all of the above requirements.

This object is solved by the subject matter of the attached claims. The different embodiments as described in the following description can be suitably combined with each other.

SUMMARY OF THE INVENTION

The present invention provides a polymer, which has antimicrobial and/or antifouling (protein-repellant) properties and is useful as a synthetic mimic of antimicrobial peptides (SMAMP).

In particular, the present invention provides the following items:

(1) A polymer, comprising a repeat unit A having a general formula selected from one of the following general formulae (I-a), (I-b), (I-c), (I-d), (I-e) and (I-f):

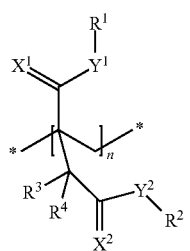
(I-a)

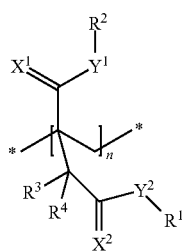
(I-b)

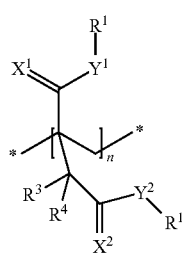
(I-c)

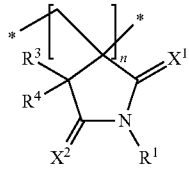
(I-d)

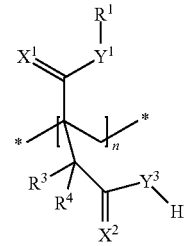
(I-e)

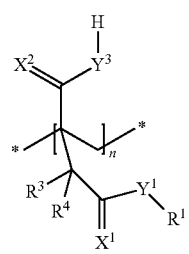
(I-f)

wherein
$R^1$ is an optionally substituted organic residue that comprises at least one cationic moiety having at least one positive charge;
$R^2$ is an optionally substituted organic residue;
$R^3$ and $R^4$ are selected independently of each other from H and an optionally substituted organic residue;
$X^1$ and $X^2$ are selected independently of each other from O and S;
$Y^1$ and $Y^2$ are selected independently of each other from O, S, NH, $NR^5$ and $PR^5$, wherein $R^5$ is $C_1$ to $C_{12}$ alkyl;
$Y^3$ is selected from O and S; and
n is from 2 to 4500.

(2) The polymer according to item (1), wherein $R^1$ and $R^2$ are selected independently of each other from an optionally substituted residue selected from the group consisting of linear or branched $C_1$ to $C_{30}$ alkyl, linear or branched $C_2$ to $C_{30}$ alkenyl, linear or branched $C_2$ to $C_{30}$ alkynyl, linear or branched $C_1$ to $C_{30}$ heteroalkyl, linear or branched $C_2$ to $C_{30}$ heteroalkenyl, linear or branched $C_2$ to $C_{30}$ heteroalkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl, $C_3$ to $C_{30}$ heterocycloalkyl, $C_4$ to $C_{30}$ heterocycloalkenyl, $C_5$ to $C_{30}$ heterocycloalkynyl, $C_6$ to $C_{30}$ aryl, linear or branched $C_7$ to $C_{30}$ arylalkyl, $C_5$ to $C_{30}$ heteroaryl, and linear or branched $C_6$ to $C_{30}$ heteroarylalkyl.

(3) The polymer according to item (1) or (2), wherein $R^2$ is selected from the group consisting of $C_1$ to $C_{12}$ alkyl, $C_3$ to $C_{12}$ cycloalkyl, $C_1$ to $C_{12}$ heteroalkyl, $C_5$ to $C_{12}$ heterocycloalkyl, $C_6$ to $C_{12}$ aryl and $C_5$ to $C_{12}$ heteroaryl.

(4) The polymer according to any one of the preceding items, wherein $R^3$ and $R^4$ are selected independently of each other from the group consisting of H, $C_1$ to $C_{12}$ alkyl, $C_3$ to $C_{12}$ cycloalkyl, $C_1$ to $C_{12}$ heteroalkyl, $C_5$ to $C_{12}$ heterocycloalkyl, $C_6$ to $C_{12}$ aryl and $C_5$ to $C_{12}$ heteroaryl.

(5) The polymer according to any one of the preceding items, wherein $R^1$ is a $C_1$ to $C_{30}$ heteroalkyl, $C_1$ to $C_{30}$ heteroalkenyl, $C_1$ to $C_{30}$ heteroalkynyl, $C_3$ to $C_{30}$ heterocycloalkyl, $C_4$ to $C_{30}$ heterocycloalkenyl, $C_5$ to $C_{30}$ heterocycloalkynyl, $C_1$ to $C_{30}$ heteroaryl, or $C_1$ to $C_{30}$ heteroarylalkyl selected from the group consisting of residues having the general formula (II), (III), (IV), (V) or (VI):

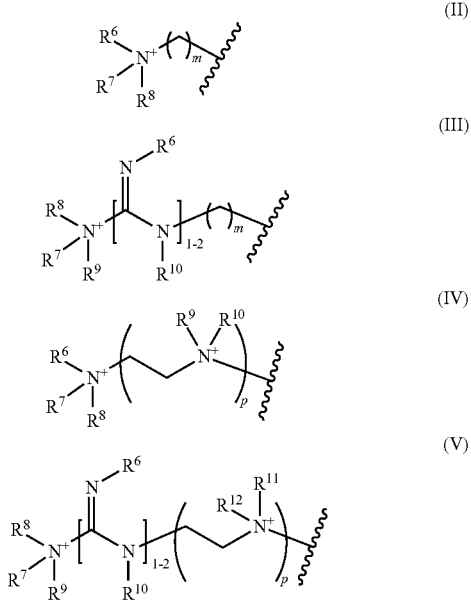

wherein
$R^6$, $R^7$, $R^8$, $R^9$, $R^{10}$, $R^{11}$ and $R^{12}$ are selected independently from each other from the group consisting of H, $C_1$ to $C_{12}$ alkyl, $C_2$ to $C_{12}$ alkenyl, $C_2$ to $C_{12}$ alkynyl, $C_3$ to $C_{12}$ cycloalkyl, $C_4$ to $C_{12}$ cycloalkenyl, $C_5$ to $C_{12}$ cycloalkynyl, $C_6$ to $C_{12}$ aryl, $C_7$ to $C_{12}$ arylalkyl, $C_1$ to $C_{12}$ heteroalkyl, $C_2$ to $C_{12}$ heteroalkenyl, $C_2$ to $C_{12}$ heteroalkynyl, $C_3$ to $C_{12}$ heterocycloalkyl, $C_4$ to $C_{12}$ heterocycloalkenyl, $C_5$ to $C_{12}$ heteroaryl, and $C_6$ to $C_{12}$ heteroarylalkyl;
m is an integer selected from 0 to 12; and
p is an integer selected from 1 to 12;

wherein
Z is selected from azolium ions or salts, imidazolium ions or salts, pyrazolium ions or salts, triazolium ions or salts, tetrazolium ions or salts, pyridinium ions or salts, pyrimidinium ions or salts, triazininum ions or salts, tetrazinium ions or salts, azepinium ions or salts, diazepinium ions or salts, thiazolium ions or salts, thiadiazolium ions or salts, thiazinium ions or salts, oxazolium ions or salts, oxadiazolium ions or salts, azirinidium ions or salts, azirinium ions or salts, azetidinium ions or salts, pyrrolidinium ions or salts, pyrrolidinium ions or salts, piperidinium ions or salts, azepanium ion or salts, imidazolinium ions or salts, purinium ions or salts, sulfonium ions or salts, phosphonium ions or salts, guanidinium ions or salts, biguanidinium ions or salts, polyguanidinium ions or salts, and combinations thereof; and q is an integer selected from 0 to 12.
(6) The polymer according to any one of the preceding items, which comprises a repeat unit A represented by general formula (I-a) or (I-b), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, $R^2$ is an unsubstituted $C_1$ to $C_{12}$ alkyl; both $R^3$ and $R^4$ are H; and each of $X^1$, $X^2$, $Y^1$ and $Y^2$ is O.
(7) The polymer according to any one of items (1) to (5), which comprises a repeat unit A represented by general formula (I-c), wherein both $R^1$ are a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.
(8) The polymer according to any one of items (1) to (5), which comprises a repeat unit A represented by general formula (I-d), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.
(9) The polymer according to any one of items (1) to (5), which comprises a repeat unit A represented by one of general formulae (I-e) or (I-f), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.
(10) The polymer according to any one of the preceding items, which consists of repeat units A only.
(11) The polymer according to item (10), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, $R^2$, if present, is an unsubstituted $C_1$ to $C_{12}$ alkyl, both $R^3$ and $R^4$ are H, and each of $X^1$, $X^2$, $Y^1$ and $Y^2$ is O.
(12) The polymer according to any one of items (1) to (9), wherein the polymer comprises at least one further repeat unit B which is derived from a monomer compound selected from the group consisting of vinyl ether, styrene or styrene derivatives, N-vinylpyrrolidone, vinyl chloride, vinyl acetate, vinylpyridine, vinylpyridinium ions or salts, a compound having general formula (VII), a compound having general formula (VIII), and itaconic acid, its sulfur containing analogues and its derivatives, as long as the respective repeat unit B is not a repeat unit A represented by one of general formulae (I-a), (I-b), (I-c), (I-d), (I-e) and (I-f):

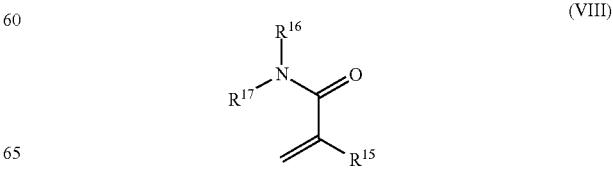

wherein
$R^{13}$ is selected from H and $C_1$ to $C_{12}$ alkyl; and
$R^{14}$ is selected from the group consisting of H and an organic residue selected from $C_1$ to $C_{12}$ alkyl and $C_1$ to $C_{12}$ heteroalkyl;

(VIII)

wherein
R$^{15}$ is selected from the group consisting of H and C$_1$ to C$_{12}$ alkyl; and
R$^{16}$ and R$^{17}$ are selected independently from each other from the group consisting of H and an organic residue selected from C$_1$ to C$_{12}$ alkyl and C$_1$ to C$_{12}$ heteroalkyl.

(13) The polymer according to item (12), wherein the repeat unit B is based on styrene or on a compound having general formula (VIII) with R$^{16}$ and R$^{17}$ selected from linear C$_1$ to C$_4$ alkyl, —CH$_2$OH, —CH$_2$CH$_2$OH or isopropyl, and the repeat unit A is represented by general formula (I-a) or (I-b), wherein R$^1$ is a residue having the general formula (II) or (III) with m being 1 or 2, and all of R$^6$, R$^7$, R$^8$, R$^9$ and R$^{10}$ being identically H or C$_1$ to C$_4$ alkyl, R$^2$ is an unsubstituted C$_1$ to C$_4$ alkyl, both R$^3$ and R$^4$ are H, and each of X$^1$, X$^2$, Y$^1$ and Y$^2$ is O.

(14) The polymer according to item (12) or (13), wherein the different versions of repeat unit A are referred to as A$_i$, and wherein the molar fractions of the different repeat units A$_i$ are referred to as r$_i$, and r is defined as the sum of all the respective molar fractions r$_i$ (r=Σr$_i$), and wherein the different versions of repeat unit B are referred to as B$_i$, and wherein the molar fractions of the different repeat units B$_i$ are referred to as s$_i$, and s is defined as the sum of all the respective molar fractions s$_i$ (s=Σs$_i$), and r=0.01 to 0.99, preferably 0.4 to 0.6, more preferably 0.5, and s=0.01 to 0.99, preferably 0.4 to 0.6, more preferably 0.5, and r+s=1 for each combination.

(15) the polymer according to one of the preceding items, wherein the polymer comprises at least one further repeat unit C, which comprises a crosslinking moiety, preferably selected from a photo-crosslinking moiety and a thermally activated crosslinking moiety.

(16) The polymer according to claim (15), wherein the polymer comprises at least one further repeat unit C, which is derived from a monomer compound having the general formula (IX):

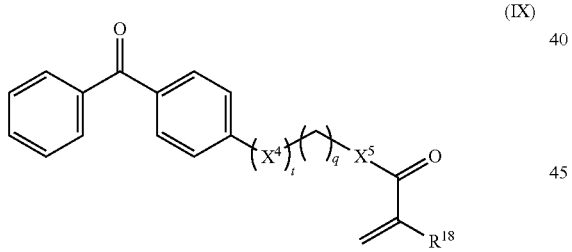

(IX)

wherein
R$^{18}$ is independently selected from H or an organic residue selected from C$_1$ to C$_{12}$ alkyl, C$_2$ to C$_{12}$ alkenyl, C$_2$ to C$_{12}$ alkynyl, C$_3$ to C$_{12}$ cycloalkyl, and C$_6$ to C$_{12}$ aryl; X$^4$ is selected from —O—, —S—, —NH—, —NR—, NR'—, —C(=O)—, —C(=S)—, —O—C(=O)—, —C(=O)—O—, —NH—C(=O)—, —NR—C(=O)—, —C(=O)—NH—, —C(=O)—NR—, —O—C(=O)—O—, —NH—C(=O)—NH—, —NR—C(=O)—NR—, —NH—C=NH—NH—, —NH—C=NR—NH, —NR—C=NH—NR—, and —NR—C=NR—NR—, wherein R represents a C$_1$ to C$_{30}$ alkyl residue and R' represents a C$_1$ to C$_{30}$ heteroalkyl residue;
X$^5$ is selected from —O—, —NH—, and —NR—, wherein R represents a C$_1$ to C$_{30}$ alkyl residue;
q is an integer of from 0 (zero) to 12; and
t is 0 (zero) or 1

(17) The polymer according to item (15) or (16), wherein the at least one repeat unit C is comprised in the polymer of the present invention in a ratio of up to 20%.

(18) The polymer according to any one of the preceding items, wherein the total number of all repeat units A, optional repeat units B, and optional repeat units C in the polymer is from 2 to 4500.

(19) The polymer according to any one of the preceding items, wherein the polymer has a number average molecular weight M$_n$ of from 220 to 1,000,000 g/mol.

(20) A use of the polymer according to any one of the preceding items for preventing microbial growth, and/or microbial adhesion, and/or protein adhesion, and/or biofouling, and/or biofilm formation by microbes or other organisms.

(21) A compound represented by one of general formulae (X-a), (X-b), (X-c), (X-d), (X-e), and (X-f):

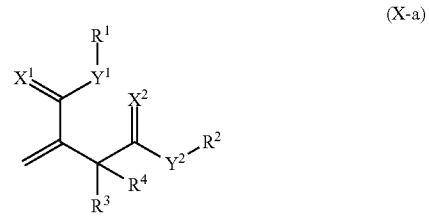

(X-a)

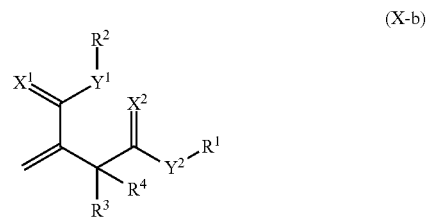

(X-b)

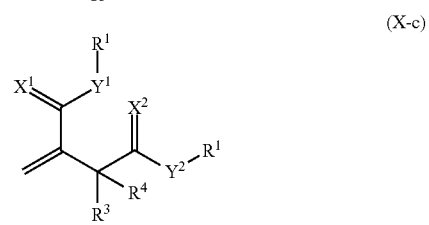

(X-c)

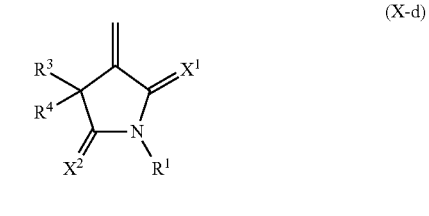

(X-d)

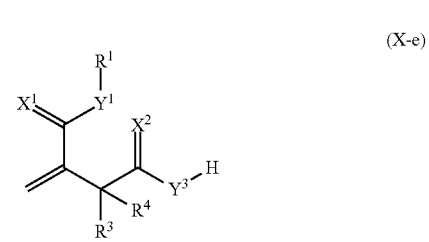

(X-e)

-continued

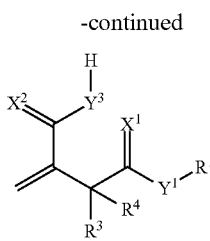
(X-f)

wherein $R^1$, $R^2$, $R^3$, $R^4$, $X^1$, $X^2$, $Y^1$, $Y^2$ and $Y^3$ are defined as for general formulae (I-a), (I-b), (I-c), (I-d), (I-e) and (I-f).

(22) The compound according to item (21), wherein $R^1$ is represented by a general formula selected from general formulae (II-P), (III-P), (IV-P) and (IV-P):

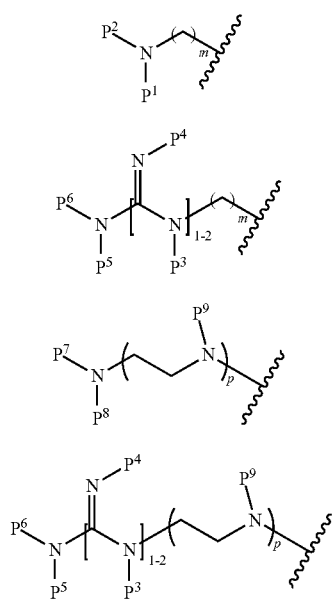

wherein m and p are as defined for formulae (II) and (III), and (IV) and (V), respectively, and $P^1$, $P^2$, $P^3$, $P^4$, $P^5$, $P^6$, $P^7$, $P^8$ and $P^9$ each represent, independently of each other, H, $C_1$ to $C_6$ alkyl or a suitable protective group, preferably selected from a tert-butyloxycarbonyl (Boc) group, a 9-fluorenylmethyloxycarbonyl (FMOC) group, and a carbamate group, or wherein $P^1$ and $P^2$, or $P^5$ and $P^6$, or $P^7$ and $P^8$, respectively, are linked and form a protective group, preferably a phthalimide group.

(23) A composition, comprising the polymer according to any one of items (1) to (19).

(24) The composition according to item (23), wherein the composition is a solution, preferably an aqueous solution or a non-aqueous solution, an emulsion, preferably a lipid emulsion or an O/W or W/O emulsion, or a formulation, a paste, a lotion, a cream or a gel.

(25) A use of the composition according to item (23) or (24) as a medical preparation for treating and/or preventing microbial infections in a patient.

(26) A use of the composition according to item (23) or (24) for preventing microbial growth on a substrate, device or tool.

(27) A medical formulation, comprising the polymer according to one of items (1) to (19) or the composition according to item (23) or (24).

(28) A substrate impregnated or coated with the polymer according to one of items (1) to (19) or with the composition according to item (23) or (24).

(29) The polymer according to items (1) to (19), wherein the polymer is bound to a surface of a substrate via a non-covalent or a covalent bond.

(30) A method of coating a substrate with the polymer according to any one of items (1) to (19), comprising the steps of:
a) optionally pretreating a surface of a substrate to comprise oxide or hydroxide groups, or other groups know to the skilled expert to react with a reactive silane;
b) functionalizing the optionally pretreated surface by covalently binding a reactive silane, thiol or disulfide compound comprising a photo-reactive crosslinker to the pretreated surface as obtained according to step a);
c) coating the surface with the optionally protected polymer according to any one of items (1) to (19), optionally adding an external photo-crosslinker, onto the surface as obtained according to step b),
d) irradiating the surface comprising the photo-reactive surface crosslinker and the optionally present external photo-crosslinker with UV light, thereby covalently binding the optionally protected polymer to a photo-reactive group of the photo-reactive surface crosslinker, thereby covalently binding the polymer to the surface and optionally crosslinking it to a surface attached network,
e) optionally carrying out a post-irradiaton treatment of the covalently bound polymer as obtained by step d) by deprotection, and/or carrying out washing steps.

(31) A method of coating a substrate with the polymer according to any one of items (1) to (19), comprising the steps of:
a) optionally pretreating a surface of a substrate to comprise oxide or hydroxide groups, or other groups know to the skilled expert to react with a reactive silane;
b) functionalizing the optionally pretreated surface by covalently binding a reactive silane, thiol or disulfide compound comprising a thermo-reactive crosslinker to the pretreated surface as obtained according to step a);
c) coating the surface with the optionally protected polymer according to any one of items (1) to (19), optionally adding an external thermo-crosslinker, onto the surface as obtained according to step b),
d) heating the surface comprising the thermo-reactive surface crosslinker and the optionally present external thermo-crosslinker, thereby covalently binding the optionally protected polymer to a thermo-reactive group of the thermo-reactive surface crosslinker, thereby covalently binding the polymer to the surface and optionally crosslinking it to a surface attached network,
e) optionally carrying out a post-irradiaton treatment of the covalently bound polymer as obtained by step d) by deprotection, and/or carrying out washing steps.

(32) A method of coating a substrate with the polymer according to any one of items (1) to (19), comprising the steps of:
a) optionally pretreating a surface of a substrate to comprise oxide or hydroxide groups, or other groups know to the skilled expert to react with a reactive silane;
b) functionalizing the optionally pretreated surface by covalently binding a reactive silane, thiol or disulfide compound comprising a photo-reactive crosslinker to the pretreated surface as obtained according to step a);

c) coating the surface with the optionally protected polymer according to any one of items (1) to (19), adding an external thermo-crosslinker, onto the surface as obtained according to step b),
d) irradiating the surface comprising the photo-reactive surface crosslinker with UV light, thereby covalently binding the optionally protected polymer to a photo-reactive group of the photo-reactive surface crosslinker, thereby covalently binding the polymer to the surface, and heating the external thermo-crosslinker, thereby crosslinking the polymer to a surface attached polymer network, e) optionally carrying out a post-irradiaton treatment of the covalently bound polymer as obtained by step d) by deprotection, and/or carrying out washing steps.
(33) A substrate coated with the polymer according to any one of items (1) to (19), obtainable or obtained by the method according to one of items (30), (31) or (32).
(34) The substrate according to one of items (28), (29), or (33), which is coated with the polymer according to any one of items (1) to (19), wherein the polymer coating has a thickness of from 10 nm to 1000 μm.

Figure 1:
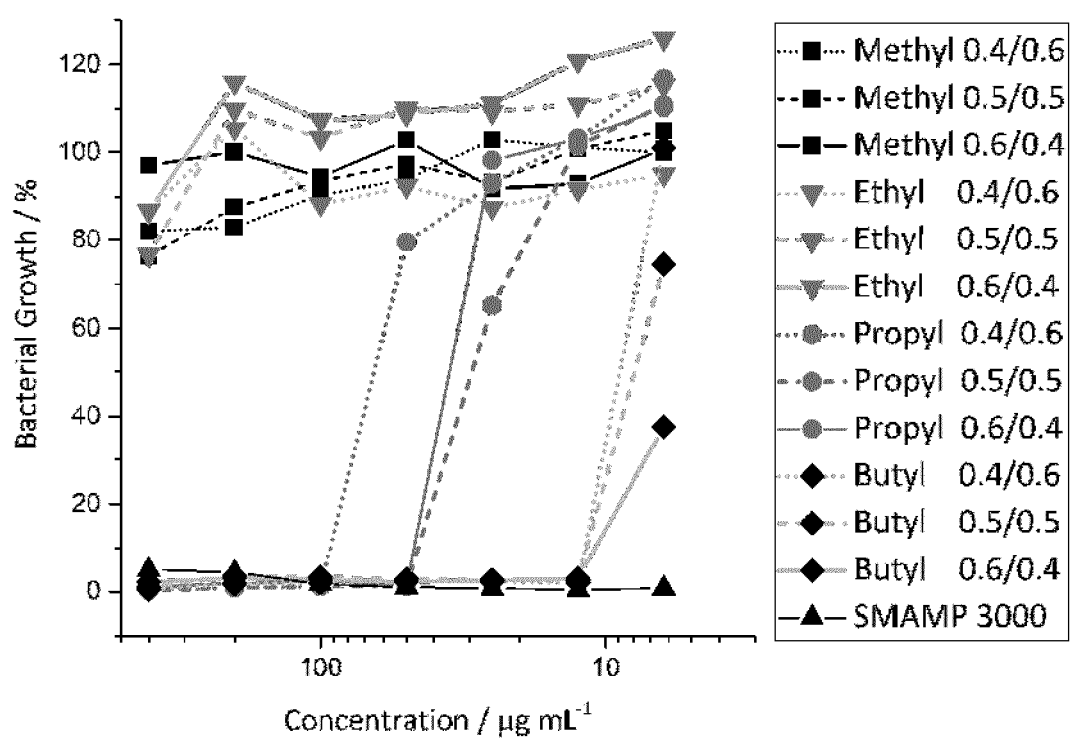
FIG. 1 shows the antimicrobial activity of Series 1 copolymers against *E. coli* (cf. Example 8).

In both figures, a legend of, for example, Methyl 0.4/0.6 refers to a copolymer comprising 40% methyl ester monomer and 60% DMAA monomer (cf. Example 6). The legend SMAMP 3000 refers to the reference propyl poly(oxanorbornene) SMAMP with a molecular mass of 3000 g mol$^{-1}$ as specified in Lienkamp, J. Am. Chem. Soc. 2008, 130, 9836.

DETAILED DESCRIPTION OF THE INVENTION

The present invention provides a polymer, which has antimicrobial and/or antifouling (protein-repellent) properties and is useful as a synthetic mimic of antimicrobial peptides (SMAMPs).

The polymer of the present invention is characterized by comprising a repeat unit derived from itaconic acid or its thiocarboxylic acid analogues (i.e. comprising the corresponding carbothioic O and/or S acid groups), which comprises at least one residue that is an organic residue comprising at least one cationic moiety having at least one positive charge.

In particular, the present invention provides a polymer, which comprises a repeat unit A having a general formula selected from one of the following general formulae (I-a), (I-b), (I-c), (I-d), (I-e) and (I-f):

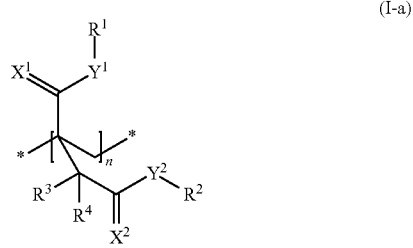

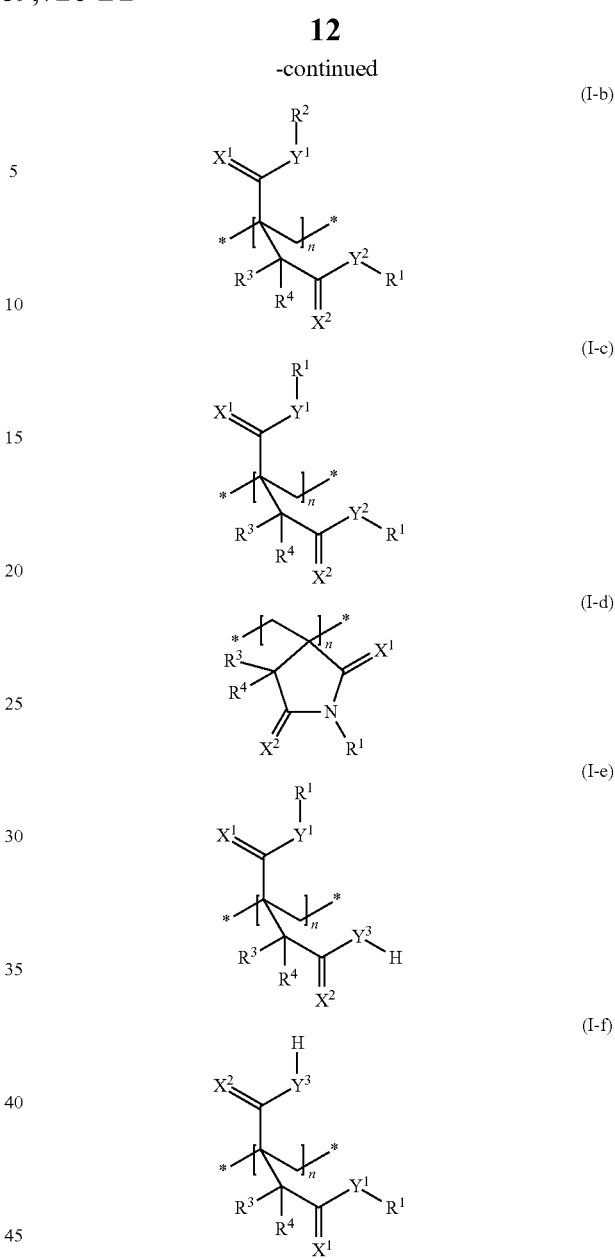

In general formulae (I-a), (I-b), (I-c), (I-d), (I-e), and (I-f), $R^1$ is an optionally substituted organic residue that comprises at least one cationic moiety having at least one positive charge.

In general formulae (I-a), (I-b), (I-c), (I-d), (I-e), and (I-f), $R^2$ is an optionally substituted organic residue.

In general formulae (I-a), (I-b), (I-c), (I-d), (I-e), and (I-f), $R^3$ and $R^4$ each represent independently of each other H or an optionally substituted organic residue.

In general formulae (I-a), (I-b), (I-c), (I-d), (I-e), and (I-f), $X^1$ and $X^2$ are selected independently of each other from O or S. Preferably, both $X^1$ and $X^2$ are O.

In general formulae (I-a), (I-b) and (I-c), $Y^1$ and $Y^2$ are selected independently of each other from O, S, NH, NR$^5$ or PR$^5$, wherein $R^5$ is $C_1$ to $C_{12}$ alkyl as defined below. Preferably, $R^5$ is $C_1$ to $C_5$ alkyl, more preferably $C_1$ to $C_3$ alkyl. Preferably, $Y^1$ and $Y^2$ are O or NH. In preferred embodiments, both $Y^1$ and $Y^2$ are O, or both $Y^1$ and $Y^2$ are NH, or one of $Y^1$ and $Y^2$ is O, and the other one is NH. In especially preferred embodiments, both $Y^1$ and $Y^2$ are O.

In specially preferred embodiments, both $X^1$ and $X^2$ are O and both $Y^1$ and $Y^2$ are O. In other especially preferred embodiments, both $X^1$ and $X^2$ are O and both $Y^1$ and $Y^2$ are NH.

In general formulae (I-e) and (I-f), $Y^3$ is selected independently of $Y^1$ from O and S. In preferred embodiments, both $Y^1$ and $Y^3$ are O, or both $Y^1$ and $Y^3$ are S, or one of $Y^1$ and $Y^3$ is O, and the other one is S. In especially preferred embodiments, both $Y^1$ and $Y^3$ are O. In specially preferred embodiments, both $X^1$ and $X^2$ are O and both $Y^1$ and $Y^3$ are O.

In general formulae (I-e) and (I-f), the group -C(=X)-$Y^3$-H may be present in its deprotonated form depending on environmental conditions, such as, e.g. adjacent groups, pH, ions contained in the environment, etc. Thus, the corresponding group -C(=$X^2$)-$Y^3$-H may be represented by -C(=O)O$^-$, -C(=O)S$^-$, -C(=S)O$^-$, or -C(=S)S$^-$, respectively. Optionally, these deprotonated groups may be conjugated with a suitable counterion, which may be a mono- or multivalent organic or inorganic cation. Preferred examples of suitable cations comprise alkali metal cations, such as, e.g., Na+, K+, etc., ammonium ions, such as, e.g., $NH_4^+$, $N(R^5)_4^+$, etc.

In general formulae (I-a), (I-b), (I-c), (I-d), (I-e), and (I-f), n represents the number of repeat units A present in the polymer. The repeat units A are connected to adjacent repeat units at the position marked by * in general formulae (I-a), (I-b), (I-c), (I-d), (I-e), and (I-f), n is from 2 to 4500, preferably from 5 to 450, and especially preferred from 10 to 100.

The repeat unit A of general formulae (I-a), (I-b), (I-c), (I-d), (I-e), and (I-f), is characterized by comprising at least one residue $R^1$ which is an organic residue that comprises at least one cationic moiety having at least one positive charge.

The polymer according to the invention provides a synthetic mimic of antimicrobial peptides (SMAMP), which exhibits the following advantages:
(a) it is stable under physiological conditions and typical conditions for biomedical applications (such as, e.g., medication formulations, surface coatings, sterilization conditions, and the like);
(b) it consists of facially amphiphilic repeat units, allowing for adjustment of its cell toxicity;
(c) it can be produced by standard polymerization methods, preferably free or controlled radical polymerization, using a non-toxic, non-metal based initiator;
(d) it can be obtained in a few easy synthetic steps making use of a flexible synthetic platform; and/or
(e) it can be obtained mostly from components that are available from renewable resources.

Advantageously, the polymer according to the present invention preferably exhibits an antimicrobial and/or antibiofouling (protein-repellent) property for preventing microbial growth and/or microbial adhesion and or/protein adhesion and/or biofouling. In the context of this invention, the term 'biofouling' refers to a process of adhering biological molecules, biological material and/or organisms or viruses, and the like, to a surface (e.g. of a polymer), for example protein adhesion, biofilm formation, etc. Accordingly, the term 'antibiofouling' refers to a property of repelling biological molecules, biological material, organisms or viruses, or the like, e.g. a protein-repellent property, a property of preventing the formation of a biofilm, and the like.

Particularly preferred, the polymer of the present invention inhibits the growth of bacteria and other pathogens (e.g. fungi), and simultaneously preferably exhibiting a low toxicity to human cells. Preferably, the inventive antimicrobial and/or antibiofouling polymer shows a significant growth reduction of bacterial pathogens of at least about 7%, more preferably at least about 70%, more preferably at least about 80%, even more preferably at least about 90%, likewise even more preferably at least about 95, 96, 97, 98, 99 or 99.99%, preferably of *E. coli, P. aeruginosa, K. pneumoniae, S. aureus, S. epidermidis,* and *E. faecalis* and other pathogens. In solution, this is preferably determined by a minimum inhibitory concentration assay as defined below. On surfaces, this is preferably determined by the spray assay defined below.

The antimicrobial activity in solution of the polymer according to the present invention can be determined by standard procedures, such as the minimum inhibitory concentration (MIC) assay, e.g., those described by Al-Ahmad et al., PLoS One 2013, 8(9), e73812 or by Rennie et al., Journal of Industrial Microbiology & Biotechnology 2005, 32(7), 296, or any other standard MIC assay e.g. according to ISO or EUCAST (European Committee on Antimicrobial Susceptibility Testing).

The antifouling activity of the polymer according to the present invention can be determined by standard procedures, e.g., those described by Jiang et al. (Quantification of the adhesion of fluorescently labeled proteins using fluorescence microscopy, after L. Mi, S. Jiang, Biomaterials 2012, 33, 8928-8933: Samples are immersed in 1 ml of 0.1 mg/ml FITC-labeled fibrinogen in PBS buffer at room temperature for 30 min to allow protein surface adsorption. After the protein incubation, samples are then rinsed gently with PBS buffer to remove any Fibrinogen that was only reversibly adhered to the surface. The surface fluorescence is then visualized using a Fluorescence Microscope through a FITC filter.) or Riihe et al. (Quantification of protein adhesion by surface plasmon resonance spectroscopy, after C. K. Pandiyarajan, O. Prucker, B. Zieger, J. Riihe, Macromol. Biosci. 2013, 13, 873-884: The adsorption of protein was evaluated by surface plasmon resonance spectroscopy. The dry thickness of the deposited surface-attached polymer network was measured, followed by the measurement of wet thickness in presence of buffer (PBS, 0.01M, pH 7.4, Sigma-Aldrich, Germany). Kinetic measurements were performed at an angle left of the minimum of the plasmon resonance curve. In a typical run, a peristaltic pump (Ismatec, Germany) was utilized to deliver the liquid samples to the SPR cell with a flow rate of 100 μL min$^{-1}$ (shear rate ca. 70 s$^{-1}$). The kinetic measurements were carried out in three stages. First, the PBS buffer was run through for 15 min to attain an equilibrium state (stable baseline). Second, fibrinogen in PBS (1 mg mL$^{-1}$) was flown in for 30 min and third, the PBS buffer was flown through for 15 min to remove non-adsorbed protein on the surface. During this process the change in the reflected intensity (R %) at the specified angle was recorded as a function of time. After completion of the kinetic measurement, the sample was dried and the dry thickness of organic layer was measured again, and the difference in the thickness before and after the experiment was taken as the adsorbed protein layer thickness.), or the like.

Preferably, $R^1$ and $R^2$ represent organic residues as defined herein, which are selected independently of each other from an optionally substituted organic residue selected from the group consisting of linear or branched $C_1$ to $C_{30}$ alkyl, linear or branched $C_2$ to $C_{30}$ alkenyl, linear or branched $C_2$ to $C_{30}$ alkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl, linear or branched $C_7$ to $C_{30}$ arylalkyl, linear or branched $C_1$ to $C_{30}$ heteroalkyl, linear or branched $C_2$ to $C_{30}$ heteroalkenyl, linear or branched $C_2$ to $C_{30}$ heteroalkynyl, $C_3$ to $C_{30}$ heterocycloalkyl, $C_3$ to $C_{30}$ heterocycloalkenyl, $C_4$ to $C_{30}$ heterocycloalkynyl, $C_5$ to $C_{30}$ heteroaryl, and linear or branched $C_6$ to $C_{30}$ heteroarylalkyl. Herein, $C_1$ to $C_{30}$ comprises $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, and $C_{30}$, referring to moieties having 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 carbon atoms.

In the context of the present invention, the term 'alkyl' refers to an organic residue on basis of a saturated hydrocarbon compound. The alkyl residue may be linear (straight-chain), branched or cyclic, or comprise combinations thereof. The alkyl residue may comprise from 1 to 30 carbon atoms, preferably from 1 to 12 carbon atoms, still more preferably from 1 to 8 carbon atoms, still more preferably from 1 to 6 carbon atoms, and especially preferred from 1 to 4 carbon atoms. Preferred examples of an alkyl residue are methyl, ethyl, n-propyl, isopropyl, n-butyl, isobutyl, sec-butyl, tert.-butyl, n-pentyl, n-hexyl, n-octyl, isooctyl, etc.

The term 'alkenyl' refers to an organic residue on basis of a partly or completely unsaturated hydrocarbon comprising at least one carbon-carbon double bond, preferably 1 to 6 double bonds, further preferred 1 to 3 double bonds, and especially preferred 1 or 2 double bonds. The alkenyl residue may be linear (straight-chain), branched or cyclic, or comprise combinations thereof. The alkenyl residue may comprise from 2 to 30 carbon atoms, preferably from 2 to 12 carbon atoms, still more preferably from 2 to 8 carbon atoms, still more preferably from 2 to 6 carbon atoms, and especially preferred from 2 to 4 carbon atoms. Preferred examples of an alkenyl residue are vinyl, allyl, propenyl, 1-butenyl, 2-butenyl, 3-butenyl, butadienyl, 1-pentenyl, 2-pentenyl, 2-methyl-3-butenyl, 2-methyl-3-pentenyl, 3-methyl-2-pentenyl, 4-methyl-3-pentenyl, etc.

The term 'alkynyl' refers to an organic residue on basis of a partly or completely unsaturated hydrocarbon comprising at least one carbon-carbon triple bond, preferably 1 to 3 triple bonds, and especially preferred 1 or 2 triple bonds. The alkynyl residue may be linear (straight-chain), branched or cyclic, or comprise combinations thereof. The alkynyl residue may comprise from 2 to 30 carbon atoms, preferably from 2 to 12 carbon atoms, still more preferably from 2 to 8 carbon atoms, still more preferably from 2 to 6 carbon atoms, and especially preferred from 2 to 4 carbon atoms. Preferred examples of an alkynyl residue are ethynyl, propynyl, 1-butynyl, 2-butynyl, 1-pentynyl, 2-pentynyl, 3-pentynyl, 2-methyl-3-butynyl, etc.

The term 'cycloalkyl' refers to an organic residue on basis of a saturated hydrocarbon compound that comprises at least one ring. The cycloalkyl residue preferably comprises 1 to 4 rings, further preferred 1 to 3 rings, still further preferred 1 or 2 rings, and especially preferred 1 ring. The cycloalkyl residue may comprise from 3 to 30 carbon atoms, preferably from 3 to 12 carbon atoms, still more preferably from 3 to 8 carbon atoms, still more preferably from 3 to 6 carbon atoms, and especially preferred 3, 4, 5, or 6 carbon atoms. Preferred examples of a cycloalkyl residue are cyclopropane, cyclobutane, cyclopentane, cyclohexane, cycloheptane, etc.

Similarly, the terms 'cycloalkenyl' and 'cycloalkynyl' refer to a (partly) unsaturated residue on basis of a corresponding hydrocarbon compound comprising at least one carbon-carbon double bond or carbon-carbon triple bond, respectively, which comprises at least one ring, preferably 1 to 4 rings, further preferred 1 to 3 rings, still further preferred 1 or 2 rings, and especially preferred 1 ring. The cycloalkenyl and cycloalkynyl residues preferably comprise 1 to 4 multiple bonds each, further preferred 1 to 3, and especially preferred 1 or 2. The cycloalkenyl residue may comprise from 4 to 30 carbon atoms, preferably from 4 to 12 carbon atoms, still more preferably from 4 to 8 carbon atoms, still more preferably from 4 to 6 carbon atoms, and especially preferred 4, 5, or 6 carbon atoms. Preferred examples of a cycloalkenyl residue are cyclobutene, cyclopentene, cyclohexene, cycloheptene, cyclohexadiene, cyclopropylmethyl, cyclobutylmethyl, etc.

The cycloalkynyl residue may comprise from 5 to 30 carbon atoms, preferably from 5 to 12 carbon atoms, still more preferably from 5 to 8 carbon atoms, and especially preferred 5 or 6 carbon atoms. Preferred examples of a cycloalkynyl residue are cyclopentinyl, cyclohexinyl, cycloheptinyl, etc.

The term 'aryl' refers to an organic residue on basis of an aromatic ring system that comprises at least one ring, preferably 1 to 4 rings, further preferred 1 to 3 rings, and especially preferred 1 or 2 rings. The aryl residue may comprise from 6 to 30 carbon atoms, preferably from 6 to 12 carbon atoms, and especially preferred 6, 10, or 12 carbon atoms. Preferred examples of an aryl residue are phenyl, naphthyl, biphenyl, etc.

The term 'arylalkyl' refers to an organic residue comprising both aliphatic and aromatic moieties, wherein the aliphatic moiety may be linear, branched or cyclic, as defined above, and the aromatic moiety comprises 1 to 4 rings, preferably 1 to 3 rings, and especially preferred 1 or 2 rings. The arylalkyl residue may comprise from 7 to 30 carbon atoms, preferably from 7 to 20 carbon atoms, further preferred from 7 to 11 carbon atoms, and especially preferred 6, 10, or 12 carbon atoms. Preferred examples of an arylalkyl residue are benzyl, tolyl, etc.

The terms 'heteroalkyl', 'heteroalkenyl', 'heteroalkynyl', 'heterocycloalkyl', 'heterocycloalkenyl', 'heterocycloalkynyl', 'heteroaryl', and 'heteroarylalkyl' refer to organic residues based on the corresponding alkyl, alkenyl, alkynyl, cycloalkyl, cycloalkenyl, cycloalkynyl, aryl, and arylalkyl residues, respectively, which comprise at least one atom other than carbon which is selected from N, O, P and S, which may be referred to as heteroatoms in the present description. The at least one heteroatom may replace a carbon and/or hydrogen atom of the respective hydrocarbon residue, or the at least one heteroatom may be inserted into a carbon-carbon or carbon-hydrogen bond of the respective hydrocarbon residue. Preferably, the total number of heteroatoms per residue is from 1 to 13, further preferred from 1 to 5, and especially preferred 1, 2, 3, 4, or 5. A residue may comprise one or more atoms of one kind of heteroatom, or one or more atoms of two or more kinds of heteroatoms. For example, a residue may comprise combinations of the heteroatoms N and O, N and S, O and P, O and S, etc., in different ratios. The heteroatoms may be comprised in the residue as a single atom or in form of a corresponding group formed from at least two heteroatoms, also formed from a combination of heteroatom(s) and carbon and/or hydrogen atoms. Preferred examples of heteroatoms and groups of heteroatoms or combinations of heteroatom/carbon/hydrogen, which may be comprised by a residue, are —O—, —NH—, —NR—, —N$^+$R$_2$—, —C(=O)—, —S$^+$—, —S+R—, —C(=S)—, —O—C(=O)—, —C(=O)—O—, —NH—C(=O)—, —NR—C(=O)—, —C(=O)—NH—, —C(=O)—NR—, —O—C(=O)—O—, —NH—C(=O)—NH—, —NR—C(=O)—NR—, —NH—C(=O)—CH=CH$_2$—, —NR—C(=O)—CH=CH$_2$—, —NH—C=NH—NH—, —NH—C=NR—NH—, —NR—C=NH—NR—, —NR—C=NR—NR—, etc., wherein R represents a corresponding part of the remaining moiety of the corresponding organic residue.

All of these heteroatom-comprising groups may be present in the residue in various combinations thereof, either adjacent to each other or at different sites within the residue. Moreover, the residue may comprise a heteroatom-comprising substituent. Examples of such substituents comprise groups, such as, e.g. hydroxyl, carboxylic acid, carboxylic acid amide, cyano, isocyano, amino, nitro, sulfhydryl, sulfonic acid, epoxy, alkoxy, such as, e.g., methoxy, etc.

Preferred examples of a heteroalkyl residue are linear or branched $C_1$ to $C_{30}$ alkoxy, preferably $C_1$ to $C_{12}$ alkoxy, such as methoxy, ethoxy, etc., or linear or branched $C_1$ to $C_{30}$ aminoalkyl, preferably $C_1$ to $C_{12}$ aminoalkyl, etc. Optionally, aminoalkyl groups may be protected using a suitable protective group, as defined below.

Preferred examples of a heteroalkenyl residue are guanidinyl, biguanidinyl, etc.

Preferred examples of a heteroalkynyl residue are nitrile, etc.

Preferred examples of a heterocycloalkyl residue are aziridinyl, epoxidyl, episulfidyl, diaziridinyl, oxetanyl, thietanyl, diazetidinyl, dioxetanyl, dithietanyl, pyrrolidinyl, oxolanyl, thiolanyl, phospholanyl, arsolanyl, imidazolidinyl, pyrazolidinyl, oxazolidinyl, isoxazolidinyl, thiazolidinyl, isothiazolidinyl, dioxolanyl, piperidinyl, oxanyl, thianyl, piperazinyl, morpholinyl, thiomorpholinyl, dioxanyl, trioxanyl, azepanyl, oxepanyl, homopiperazinyl, azocanyl, oxocanyl, thiocanyl, etc.

Preferred examples of a heterocycloalkenyl residue are azirin, aziridin, azacyclobutadien, furan, etc.

Preferred examples of a heteroaryl residue are pyrrol, furanyl, thiophenyl, pyrazolyl, oxazolyl, isoxazolyl, thiazolyl, pyridinyl, pyrazinyl, pyrimidinyl, pyridazinyl, benzofuranyl, indolyl, purinyl, indazolyl, chinolinyl, isochinolinyl, etc.

Preferably, at least one of the residues $R^1$ and $R^2$ comprises a hydrophilic function. For example, the residue $R^1$ or $R^2$ may comprise a heteroatom as specified above as part of an organic residue. Moreover, each of the above organic residues may be optionally substituted with one or more hydrophilic group(s). Herein, the term 'hydrophilic group' refers to a molecular moiety or substituent capable to interact with polar solvents, in particular water, or with other polar groups. In contrast, the term 'hydrophobic group' refers to a non-polar moiety or substituent incapable of interaction with water, leading to the tendency of exclusion from water and/or association in an aqueous environment.

Preferably, a hydrophilic group is selected from the group consisting of hydroxyl, methoxy, carboxylic acids and ions and salts thereof, amides, amino, cyano, isocyano, nitrile, ammonium ions or salts, sulfonium ions or salts, phosphonium ions or salts, guanidinium, biguanidinium, imidazolium mono- and di-alkyl substituted amino groups, polyethylene glycols, glycosyl groups, sugars, epoxy groups, acrylates, sulfonamides, nitro, aminate, acrylamide, pyridinium, piperidine, pyrazole, pyrol, imidazole, azirine, aziridine, diaziridine, azetidine, azete, diazetidine, azolidine, phosopholane, phosphole, arsolane, imidazolidine, pyrazolidine, imidazolin, pyrazoline, oxazolidine, isoxazolidine, oxazole, oxazoline, isoxazole, isoxazoline, thiazolidin, isothiazolidin, thiazole, thiazolin, isothiazole, isothiazoline, triazole, dithiazole, furazan, oxadiazole, thiadiazole, tetrazole, piperazine, diazine, morpholin, oxazin, thiazin, triazin, tetrazine, zwitterions or amino acids, and combinations thereof, or from $OP(O)(OCH_2CH_2N^+RRR)O^-$, wherein each R is independently selected from H or an alkyl as defined herein. Further examples include poly(methylene) chains poly(ethyleneoxide) chains substituted with alcohol, carboxylate, acrylate, or methacrylate. Hydrophilic moieties may also include alkyl chains having internal amino or substituted amino groups, for example, internal —NH, —NC(O)R, or —NC(O)CH═$CH_2$-groups, wherein R is H or an alkyl as defined herein. A person skilled in the art will know how to use an appropriate protective group in case that any of the above hydrophilic groups is not compatible with the radical polymerization conditions chosen. In such case, the group is additionally modified with the protective group prior to the polymerization, and the protective group is then removed after the polymerization by an appropriate method that does not to damage the chemical integrity of the polymer produced. Suitable protective groups and methods are known to the skilled person. Examples will be outlined below.

$R^1$ is an organic residue that comprises at least one cationic moiety having at least one positive charge. Preferably, $R^1$ is an organic residue, which is an optionally substituted organic residue selected from the group consisting of linear or branched $C_1$ to $C_{30}$ alkyl, linear or branched $C_2$ to $C_{30}$ alkenyl, linear or branched $C_2$ to $C_{30}$ alkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl, linear or branched $C_7$ to $C_{30}$ arylalkyl, linear or branched $C_1$ to $C_{30}$ heteroalkyl, linear or branched $C_2$ to $C_{30}$ heteroalkenyl, linear or branched $C_2$ to $C_{30}$ heteroalkynyl, $C_3$ to $C_{30}$ heterocycloalkyl, $C_3$ to $C_{30}$ heterocycloalkenyl, $C_4$ to $C_{30}$ heterocycloalkynyl, $C_5$ to $C_{30}$ heteroaryl, and linear or branched $C_6$ to $C_{30}$ heteroarylalkyl, each as defined above, under the proviso that the organic residue comprises at least one cationic moiety having at least one positive charge.

In this context, the term "having at least one positive charge" refers to a moiety having from one or more positive charges, preferably from one to thirteen positive charges, further preferred from one to five positive charges, still further preferred one, two or three positive charges, and especially preferred one positive charge.

Preferably, the at least one positive charge is located at a heteroatom, further preferred at a nitrogen atom, a sulfur atom or a phosphorous atom, and especially preferred at a nitrogen atom. The at least one positive charge may also be delocalized over more than one heteroatom or over a group of atoms comprising at least one heteroatom and one or more carbon atom(s). Preferably, the heteroatom bearing the positive charge may be an atom of a corresponding heteroalkyl, heteroalkenyl, heteroalkynyl, heterocycloalkyl, heterocycloalkenyl, heterocycloalkynyl, heteroaryl, and heteroarylalkyl residue, or an atom of a substituent of a corresponding alkyl, heteroalkyl, alkenyl, heteroalkenyl, alkynyl, heteroalkynyl, cycloalkyl, heterocycloalkyl, cycloalkenyl, heterocycloalkenyl, cycloalkynyl, heterocycloalkynyl, aryl, heteroaryl, arylalkyl and heteroarylalkyl residue, respectively, each as defined above.

Preferably, $R^1$ is an organic residue selected from a $C_1$ to $C_{30}$ heteroalkyl, $C_1$ to $C_{30}$ heteroalkenyl, $C_1$ to $C_{30}$ heteroalkynyl, $C_3$ to $C_{30}$ heterocycloalkyl, $C_4$ to $C_{30}$ heterocycloalkenyl, $C_5$ to $C_{30}$ heterocycloalkynyl, $C_1$ to $C_{30}$ heteroaryl, or $C_1$ to $C_{30}$ heteroarylalkyl, each as defined above.

Preferably, the at least one positive charge is located at a nitrogen atom which is a substituent, e.g. in form of a —$N^+H_3$ or ═$N^+H_2$ group, or which is part of a linear or branched chain, e.g. in form of a —$N^+H_2R$, —$N^+H(R')R$—, or —$N^+(R')_2R$— group (with R and R' independently of each other being selected from an organic residue as defined herein), or which is part of a (partly) unsaturated or aromatic ring, e.g. an azolium ring, am imidazolium ring, a pyrazolium ring, a pyridinium ring, and the like. Especially preferred, the at least one positive charge is located at an ammonium nitrogen atom. In especially preferred embodiments, $R^1$ comprises a $C_1$ to $C_7$ heteroalkyl carrying a positive charge, preferably —$CH_2CH_2NH_3^+$, —$CH_2CH_2CH_2NH_3^+$, —$CH_2CH_2CH_2CH_2NH_3^+$, or —$CH_2CH_2CH_2CH_2CH_2NH_3^+$; or —$CH_2CH_2$-guanidinium, —$CH_2CH_2CH_2$-guanidinium, —$CH_2CH_2CH_2CH_2$-guanidinium, or —$CH_2CH_2CH_2CH_2CH_2$-guanidinium; or —$CH_2CH_2$-biguanidinium, —$CH_2CH_2CH_2$-biguanidinium, —$CH_2CH_2CH_2CH_2$-biguanidinium, or —$CH_2CH_2CH_2CH_2CH_2$-biguanidinium.

Preferably, $R^2$ is selected from the group consisting of $C_1$ to $C_{12}$ alkyl, $C_3$ to $C_{12}$ cycloalkyl, $C_1$ to $C_{12}$ heteroalkyl, $C_5$ to $C_{12}$ heterocycloalkyl, $C_6$ to $C_{12}$ aryl and $C_5$ to $C_{12}$ heteroaryl, wherein the respective residues are as defined above. Further preferred, $R^2$ is selected from $C_1$ to $C_4$ alkyl.

Preferably, the residues $R^3$ and $R^4$ are selected independently of each other from the group consisting of H, $C_1$ to $C_{12}$ alkyl, $C_3$ to $C_{30}$ cycloalkyl, $C_1$ to $C_{12}$ heteroalkyl, $C_5$ to $C_{12}$ heterocycloalkyl, $C_6$ to $C_{12}$ aryl and $C_5$ to $C_{12}$ heteroaryl, wherein the respective residues are as defined above. Further preferred, the $C_1$ to $C_{12}$ heteroalkyl is $C_1$ to $C_{12}$ alkoxy. Preferably, $R^3$ and $R^4$ are selected from the group consisting of H and $C_1$ to $C_3$ alkyl. Especially preferred, both $R^3$ and $R^4$ are H.

In especially preferred embodiments, $R^1$ is a $C_1$ to $C_{30}$ heteroalkyl, $C_1$ to $C_{30}$ heteroalkenyl, $C_1$ to $C_{30}$ heteroalkynyl, $C_3$ to $C_{30}$ heterocycloalkyl, $C_4$ to $C_{30}$ heterocycloalkenyl, $C_5$ to $C_{30}$ heterocycloalkynyl, $C_1$ to $C_{30}$ heteroaryl, or $C_1$ to $C_{30}$ heteroarylalkyl selected from the group consisting of residues having one of the general formula (II), (III), (IV), (V) or (VI) as defined below.

The organic residues having general formulae (II), (III), (IV) and (V):

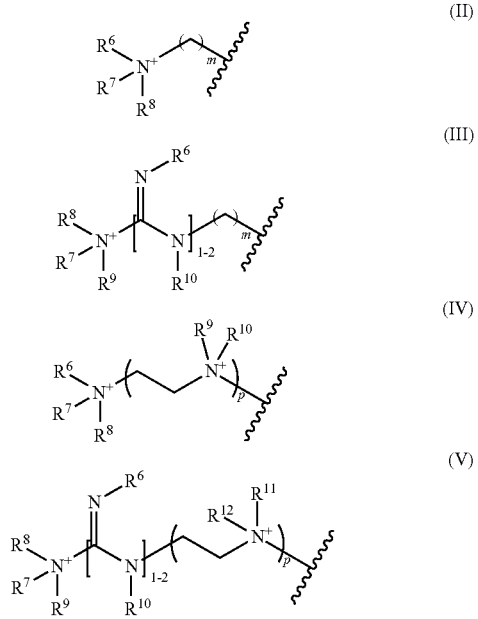

In general formulae (II), (III), (IV) and (V), $R^6$, $R^7$, $R^8$, $R^9$, $R^{10}$, $R^{11}$ and $R^{12}$ represent independently from each other H or an organic residue selected from linear, branched, cyclic, saturated, partially saturated and/or unsaturated $C_1$ to $C_{12}$ alkyl, $C_2$ to $C_{12}$ alkenyl, $C_2$ to $C_{12}$ alkynyl, $C_3$ to $C_{12}$ cycloalkyl, $C_4$ to $C_{12}$ cycloalkenyl, $C_5$ to $C_{12}$ cycloalkynyl, $C_1$ to $C_{12}$ heteroalkyl, $C_2$ to $C_{12}$ heteroalkenyl, $C_2$ to $C_{12}$ heteroalkynyl, $C_3$ to $C_{12}$ heterocycloalkyl, $C_4$ to $C_{12}$ heterocycloalkenyl, $C_5$ to $C_{12}$ heterocycloalkynyl, $C_6$ to $C_{12}$ aryl, $C_7$ to $C_{12}$ arylalkyl, $C_5$ to $C_{12}$ heteroaryl, and $C_6$ to $C_{12}$ heteroarylalkyl groups, which may be optionally substituted.

Preferably, $R^6$, $R^7$, $R^8$, $R^9$, $R^{10}$, $R^{11}$ and $R^{12}$ are selected from H and $C_1$ to $C_6$ alkyl, and especially preferred from H and $C_1$ to $C_4$ alkyl. In the case where any of $R^6$, $R^7$, $R^8$, $R^9$, $R^{10}$, $R^{11}$ and $R^{12}$ are H in formulae (III) and (V), these residues also comprise all the resonance structures of that molecule known to the skilled expert.

In general formulae (II) and (III), m is an integer selected from 0 to 12. Preferably, m is an integer from 1 to 4, more preferably 1 or 2, and especially preferred m=2.

In general formulae (IV) and (V), p is an integer selected from 1 to 12. Preferably, p is an integer from 1 to 4, more preferably 1 or 2, and especially preferred p=1.

Preferably, the organic residue having one of general formulae (II), (III), (IV) or (V) is present in form of a salt comprising a corresponding number of counterions (anions) per positive charge. Examples of corresponding anions are given below.

The organic residue having general formula (VI):

In general formula (VI), Z is selected from azolium ions or salts, imidazolium ions or salts, pyrazolium ions or salts, triazolium ions or salts, tetrazolium ions or salts, pyridinium ions or salts, pyrimidinium ions or salts, triazininum ions or salts, tetrazinium ions or salts, azepinium ions or salts, diazepinium ions or salts, thiazolium ions or salts, thiadiazolium ions or salts, thiazinium ions or salts, oxazolium ions or salts, oxadiazolium ions or salts, azirinidium ions or salts, azirinium ions or salts, azetidinium ions or salts, pyrrolidinium ions or salts, pyrrolidinium ions or salts, piperidinium ions or salts, azepanium ion or salts, imidazolinium ions or salts, purinium ions or salts, sulfonium ions or salts, phosphonium ions or salts, guanidinium ions or salts, biguanidinium ions or salts, polyguanidinium ions or salts, and combinations thereof; and q is an integer selected from 0 to 12.

Preferably, q is an integer selected from 1 to 4, more preferably 1 or 2.

Preferably, a salt of organic residues having general formulae (II), (III), (IV), (V) and (VI) comprises a corresponding number of counterions (anions) per positive charge. The anion comprises at least one negative charge, preferably from 1 to 3 negative charges. Preferably, the anion is a monovalent or divalent inorganic or organic anion. Preferably, the anion is a monovalent inorganic anion. Preferred examples of monovalent inorganic anions comprise hydroxide, halogenides, such as chloride, bromide, iodide, nitrate, hydrogen sulfate, dihydrogenphosphate or other conjugate bases of common monovalent inorganic acids. Preferred examples of divalent inorganic anions comprise sulfate, carbonate, hydrogen phosphate, etc., and other conjugate bases of common divalent inorganic acids. Preferred examples of trivalent inorganic anions comprise phospate and other conjugate bases of common divalent inorganic acids.

Preferred examples of monovalent/divalent organic anions comprise mono-, bi- or trivalent organic ions such as trifluoroacetate, acetate, alkylsulfonate, alkylsulfate, tosylate, arylsulfonate, arylsulfate, citrate, or other conjugate bases of common organic acids, etc.

In preferred embodiments of the polymer according to the present invention, $R^1$ is a heteroalkyl residue represented by one of general formulae (II) or (III) with m being 1 or 2, and all of $R^6$, $R^7$, $R^8$, $R^9$ and $R^{10}$ being identically H or $C_1$ to $C_4$ alkyl, preferably H or methyl or ethyl, and especially preferred H. In especially preferred embodiments of the polymer according to the present invention, $R^1$ is a $C_1$ to $C_7$ heteroalkyl carrying a positive charge, preferably —$CH_2CH_2NH_3^+$, —$CH_2CH_2CH_2NH_3^+$, —$CH_2CH_2CH_2CH_2NH_3^+$, or —$CH_2CH_2CH_2CH_2CH_2NH_3^+$; or —$CH_2CH_2$-guanidinium, —$CH_2CH_2CH_2$-guanidinium, —$CH_2 CH_2CH_2CH_2$-guanidinium, or —$CH_2CH_2CH_2CH_2 CH_2$-guanidinium; or —$CH_2CH_2$-biguanidinium, —$CH_2CH_2CH_2$-biguanidinium, —$CH_2CH_2CH_2CH_2$-biguanidinium, or —$CH_2CH_2CH_2CH_2CH_2$-biguanidinium. Especially preferred, $R^1$ is a —$CH_2$—$CH_2$—$N^+H_3$ group, a —$CH_2$—$CH_2$—NH—C(=NH)—$NH_3^+$ group or a —$CH_2$—$CH_2$—(NH—[C(=NH)])$_2$—$NH_3^+$ group.

It was found that polymers comprising a repeat unit A as defined in the preceding paragraphs provide synthetic mimics of antimicrobial peptides (SMAMPs), which are associated with especially advantageous properties, especially with advantageous antimicrobial and/or antifouling (protein-repellent) properties.

In especially preferred embodiments of the polymer according to the present invention, $R^1$ comprises an organic residue comprising a cationic moiety as defined herein, and $R^2$, if present, is a hydrophobic organic residue. Herein, a hydrophobic organic residue is as defined above, without including a hydrophilic substituent. Preferably, the hydrophobic organic residue is selected from the group consisting of $C_1$ to $C_{30}$ alkyl, $C_2$ to $C_{30}$ alkenyl, $C_2$ to $C_{30}$ alkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl and $C_7$ to $C_{30}$ arylalkyl, further preferred from the respective residues having up to 12 carbon atoms. Accordingly, $R^2$ is preferably selected from the group consisting of $C_1$ to $C_{30}$ alkyl, $C_2$ to $C_{30}$ alkenyl, $C_2$ to $C_{30}$ alkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl and $C_7$ to $C_{30}$ arylalkyl, further preferred from the respective residues having up to 12 carbon atoms. Especially preferred, $R^2$ is selected from the group consisting of $C_1$ to $C_{12}$ alkyl and $C_6$ to $C_{12}$ aryl.

In further preferred embodiments of the polymer according to the present invention, $R^1$ is a residue having the general formula (II) or (III), preferably with $R^6$, $R^7$, $R^8$, $R^9$ and $R^{10}$ being H or $C_1$ to $C_4$ alkyl, and $R^2$, if present, is an unsubstituted $C_1$ to $C_{12}$ alkyl, both $R^3$ and $R^4$ are H, and each of $X^1$, $X^2$, $Y^1$ and $Y^2$ is O. In an especially preferred embodiment, $R^1$ is a residue having the general formula (II) or (III) with m being 1 or 2, and all of $R^6$, $R^7$, $R^8$, $R^9$ and $R^{10}$ being identically H or $C_1$ to $C_4$ alkyl, and $R^2$, if present, is an unsubstituted $C_1$ to $C_4$ alkyl, both $R^3$ and $R^4$ are H, and each of $X^1$, $X^2$, $Y^1$ and $Y^2$ is O.

In preferred embodiments of the polymer according to the present invention comprising a repeat unit having formula (I-a) or (I-b), $R^1$ is selected from the group —$CH_2CH_2NH_3^+$, —$CH_2CH_2CH_2NH_3^+$, —$CH_2CH_2CH_2CH_2NH_3^+$, —$CH_2CH_2CH_2CH_2CH_2NH_3^+$; or —$CH_2CH_2$-guanidinium, —$CH_2CH_2CH_2$-guanidinium, —$CH_2 CH_2CH_2CH_2$-guanidinium, or —$CH_2CH_2CH_2CH_2 CH_2$-guanidinium; or —$CH_2CH_2$-biguanidinium, —$CH_2CH_2CH_2$-biguanidinium, —$CH_2CH_2CH_2CH_2$-biguanidinium, or —$CH_2CH_2CH_2CH_2CH_2$-biguanidinium, and $R^2$ is selected from the group consisting of $C_1$ to $C_7$ alkyl, both $R^3$ and $R^4$ are H, and each of $X^1$, $X^2$, $Y^1$ and $Y^2$ is O.

In especially preferred embodiments, the polymer according to the present invention comprises a repeat unit A represented by general formula (I-a) or (I-b), wherein $R^1$ is a residue having the general formula (II), preferably with $R^6$, $R^7$ and $R^8$ being H or $C_1$ to $C_4$ alkyl, and $R^2$ is an unsubstituted $C_1$ to $C_{12}$ alkyl; both $R^3$ and $R^4$ are H; and each of $X^1$, $X^2$, $Y^1$ and $Y^2$ is O. Especially preferred, $R^2$ is a $C_1$ to $C_4$ alkyl.

In alternative preferred embodiments of the polymer according to the present invention comprising a repeat unit A having formula (I-c), both $R^1$ are a residue having the general formula (II) or (III), preferably with $R^6$, $R^7$, $R^8$, $R^9$ and $R^{10}$ being H or $C_1$ to $C_4$ alkyl, both $R^3$ and $R^4$ are H, and each of $X^1$, $X^2$, $Y^1$ and $Y^2$ is O.

In other especially preferred embodiments, the polymer according to the present invention comprises a repeat unit A represented by general formula (I-c), wherein both $R^1$ are a residue having the general formula (II), preferably with $R^6$, $R^7$ and $R^8$ being H or $C_1$ to $C_4$ alkyl, both $R^3$ and $R^4$ are H; and each of $X^1$, $X^2$, $Y^1$ and $Y^2$ is O.

In other especially preferred embodiments, the polymer according to the present invention comprises a repeat unit A represented by general formula (I-d), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.

In other especially preferred embodiments, the polymer according to the present invention comprises a repeat unit A represented by one of general formulae (I-e) or (I-f), wherein $R^1$ is a residue having the general formula (II or III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.

In alternative preferred embodiments of the polymer according to the present invention comprising a repeat unit having formula (I-a) or (I-b), $R^1$ comprises a cationic moiety, preferably being an organic residue having one of general formulae (II), (III), (IV), (V), or (VI), as defined above, and especially preferred a —$CH_2$—$CH_2$—$N^+H_3$ group, a —$CH_2$—$CH_2$—NH—C(=NH)—$NH_3^+$ group or a —$CH_2$—$CH_2$—(NH—[C(=NH)])$_2$—$NH_3^+$ group, and $R^2$ comprises an anionic moiety, preferably a deprotonated carboxylic acid group, e.g. a $C_1$ to $C_{12}$ alkyl residue substituted with a deprotonated carboxylic acid group, similar as in the deprotonated repeat units of formulae (I-e) and (I-f).

It was surprisingly found that the polymer according to the present invention comprising a repeat unit having formula (I-a), (I-b), (I-c) or (I-d) as defined above exhibits very high antimicrobial properties. It is assumed that the general antimicrobial property is associated with the positive charge of residue $R^1$, and can be further amplified in combination with a hydrophobic residue $R^2$. Moreover, it was surprisingly found that the polymer according to the present invention comprising a repeat unit having formula (I-e) or (I-f) as defined above exhibits very high antifouling properties. It is assumed that the general antifouling property is associated with the Zwitterion character, which is present in those repeat units when $Y^3$ is deprotonated, preferably resulting in charge neutrality of the overall polymer. A similar effect may be observed in the polymer according to the present invention comprising a repeat unit having formula (I-a), (I-b), (I-c) or (I-d) when $R^2$ is an organic residue that comprises a group carrying a negative charge.

In an especially preferred embodiment of the polymer according to the present invention, the polymer consists of repeat units A only, wherein the repeat units A may be identical or different from each other. In case the repeat units A of the polymer are identical, the polymer may be referred to as a 'homopolymer' in the following.

A polymer according to the present invention preferably consists of repeat units A, wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, $R^2$, if present, is an unsubstituted $C_1$ to $C_{12}$ alkyl, both $R^3$ and $R^4$ are H, and each of $X^1$, $X^2$, $Y^1$ and $Y^2$ is O. In an especially preferred embodiment, $R^1$ is a residue having the general formula (II) or (III) with m being 1 or 2, and all of $R^6$, $R^7$ and $R^8$ being identically H or $C_1$ to $C_4$ alkyl, $R^2$, if present, is an unsubstituted $C_1$ to $C_4$ alkyl, both $R^3$ and $R^4$ are H, and each of $X^1$, $X^2$, $Y^1$ and $Y^2$ is O. Especially preferred, $R^1$ is a $-CH_2-CH_2-N^+H_3$ group, a $-CH_2-CH_2-NH-C(=NH)-NH_3^+$ group or a $-CH_2-CH_2-(NH-[C(=NH)])_2-NH_3^+$ group, $R^2$, if present, is an unsubstituted $C_1$ to $C_4$ alkyl, both $R^3$ and $R^4$ are H, and each of $X^1$, $X^2$, $Y^1$ and $Y^2$ is O.

It was found that a homopolymer of the invention consisting of repeat units A is associated with all advantageous properties required to solve the object of the present invention.

In particular, it was surprisingly found that the homopolymer comprising a repeat unit having formula (I-a), (I-b), (I-c) or (I-d) exhibits very high antimicrobial properties. Moreover, it was surprisingly found that the homopolymer comprising a repeat unit having formula (I-e) or (I-f) exhibits very high antifouling properties, especially when $Y^3$ is deprotonated.

Preferably, the homopolymer has a molecular weight of from 1000 g/mol to 1000000 g/mol, further preferred of from 2000 g/mol to 100000 g/mol, and especially preferred of from 3000 g/mol to 50000 g/mol.

In preferred embodiments of the present invention, the homopolymer comprises repeat units having the general formula (I-a), (I-b), (I-c) or (I-d) with $X^1=X^2=Y^1=Y^2=O$, $R^1$ being an organic residue having formula (II), (III), (IV) or (V), and $R^2=C_3$ to $C_7$ alkyl, cycloalkyl, heteroalkyl alkenyl, heteroalkenyl, cylcoalkenyl, heterocyloalkenyl, alkynyl, or heteroalkynyl or $C_5$ to $C_7$ aryl, heteroaryl, alkylaryl, or heteroalkylaryl, as defined above; preferably with $X^1=X^2=y=Y^2=O$, $R^1$ being an organic residue having formula (II), (III), (IV) or (V) (with m=2 or p=1 and $R^6$, $R^7$, $R^8$, $R^9$, $R^{10}$, $R^{11}$ and $R^{12}$=H), and $R^2=C_3$ to $C_7$ alkyl, heteroalkyl, benzyl or phenyl; and especially preferred with $X^1=X^2=Y^1=Y^2=O$, $R^1$ being an organic residue having formula (II) or (III) (with m=2 and $R^6$, $R^7$, $R^8$, $R^9$, $R^{10}$=H), and $R^2=C_3$ to $C_5$ alkyl or phenyl.

In other preferred embodiments of the present invention, the homopolymer comprises repeat units having the general formula (I-a), (I-b), (I-c) or (I-d) with $X^1=X^2=O$, and one of $Y^1$ or $Y^2$ being NH and the other one of $Y^1$ or $Y^2$ being O, $R^1$ being an organic residue having formula (II), (III), (IV) or (V), and $R^2=C_3$ to $C_7$ alkyl, cycloalkyl, heteroalkyl alkenyl, heteroalkenyl, cylcoalkenyl, heterocyloalkenyl, alkynyl, or heteroalkynyl or $C_5$ to $C_7$ aryl, heteroaryl, alkylaryl, or heteroalkylaryl, as defined above; preferably with $X^1=X^2=O$, and one of $Y^1$ or $Y^2$ being NH and the other one of $Y^1$ or $Y^2$ being O, $R^1$ being an organic residue having formula (II), (III), (IV) or (V) (with m=2 or p=1 and $R^6$, $R^7$, $R^8$, $R^9$, $R^{10}$, $R^{11}$ and $R^{12}$=H), and $R^2=C_3$ to $C_7$ alkyl, heteroalkyl, benzyl or phenyl; and especially preferred with $X^1=X^2=O$, and one of $Y^1$ or $Y^2$ being NH and the other one of $Y^1$ or $Y^2$ being O, $R^1$ being an organic residue having formula (II) or (III) (with m=2 and $R^6$, $R^7$, $R^8$, $R^9$, $R^{10}$=H), and $R^2=C_3$ to $C_5$ alkyl or phenyl.

In other preferred embodiments of the present invention, the homopolymer comprises repeat units having the general formula (I-a), (I-b), (I-c) or (I-d) with $X^1=X^2=O$, $Y^1=Y^2=NH$, $R^1$ being an organic residue having formula (II), (III), (IV) or (V), and $R^2=C_3$ to $C_7$ alkyl, cycloalkyl, heteroalkyl alkenyl, heteroalkenyl, cylcoalkenyl, heterocyloalkenyl, alkynyl, or heteroalkynyl or $C_5$ to $C_7$ aryl, heteroaryl, alkylaryl, or heteroalkylaryl, as defined above; preferably with $X^1=X^2=O$, $Y=Y^2=NH$, $R^1$ being an organic residue having formula (II), (III), (IV) or (V) (with m=2 or p=1 and $R^6$, $R^7$, $R^8$, $R^9$, $R^{10}$, $R^{11}$ and $R^{12}$=H), and $R^2=C_3$ to $C_7$ alkyl, heteroalkyl, benzyl or phenyl; and especially preferred with $X^1=X^2=O$, $Y^1=Y^2=NH$, $R^1$ being an organic residue having formula (II) or (III) (with m=2 and $R^6$, $R^7$, $R^8$, $R^9$, $R^{10}$=H), and $R^2=C_3$ to $C_5$ alkyl or phenyl.

In another especially preferred embodiment of the polymer according to the present invention, the polymer comprises, in addition to the at least one repeat unit A, at least one further repeat unit B. Repeat unit B is derived from another monomer that is copolymerizable with repeat units A, which are derived from itaconic acid, its sulfur containing analogues or its respective derivatives. Monomers known to copolymerize with itaconic acid and/or itaconates are known to a person skilled in the art, for example from M. Mishra/Y. Yagci: Handbook of Vinyl Polymers: Radical Polymerization, Process, and Technology, Second Edition (Plastics Engineering), CRC Press, 2016; or K. Matyjaszewski/T. P. Davis: Handbook of Radical Polymerzation; Wiley, 2002.

Preferably, repeat unit B is derived from a compound selected from the group consisting of vinyl ether, styrene or styrene derivatives, N-vinylpyrrolidone, vinyl chloride, vinyl acetate, vinylpyridine, vinylpyridinium ions or salts, a compound having general formula (VII) and a compound having general formula (VIII) as specified below. Preferably, a vinyl ether is a $C_1$ to $C_{12}$ alkyl, alkenyl, or alkynyl vinyl ether, more preferably a $C_2$ alkyl, alkenyl, or alkynyl vinyl ether.

Alternatively, repeat unit B may also be derived from itaconic acid, its sulfur containing analogues or its respective derivatives, as long as the respective repeat unit B is not a repeat unit A represented by one of general formulae (I-a), (I-b), (I-c), (I-d), (I-e) and (I-f). For example, repeat unit B may be itaconic acid, its anhydride or an itaconic acid derivative, such as, e.g., a mono or di alkyl ester or amide, and the like. For example, repeat unit B may also be a derivative of itaconic acid, as represented by general formula (I-c), (I-d), (I-e) or (I-f), wherein each residue $R^1$ is substituted by a residue $R^2$, and wherein all of $R^3$, $R^4$, $X^1$, $X^2$, $Y^1$, and $Y^2$ are as defined for general formulae (I-c), (I-d), (I-e) and (I-f). Especially preferred examples comprise the mono and di $C_1$ to $C_4$ alky esters or amides of itaconic acid as well as the $C_1$ to $C_4$ alkyl imide of itaconic acid.

The compound having general formula (VII):

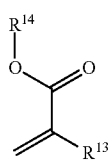

(VII)

Herein, $R^{13}$ is selected from the group consisting of H and $C_1$ to $C_{12}$ alkyl, preferably H and $C_1$ to $C_6$ alkyl, and especially preferred H and methyl.

$R^{14}$ is selected from the group consisting of H and an organic residue selected from $C_1$ to $C_{12}$ alkyl and $C_1$ to $C_{12}$ heteroalkyl. Preferably, $R^{14}$ is H, $C_1$ to $C_6$ alkyl or $C_1$ to $C_4$ heteroalkyl, more preferably H, $C_1$ to $C_4$ alkyl, especially methyl or ethyl, —$CH_2$—$CH_2$—OH or —$CH_2$—$CH_2$—$NH_2$.

The compound having general formula (VIII):

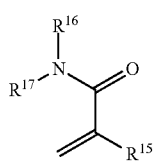

(VIII)

Herein, $R^{15}$ is selected from the group consisting of H and $C_1$ to $C_{12}$ alkyl, preferably from H and $C_1$ to $C_6$ alkyl, and especially preferred from H and methyl.

$R^{16}$ and $R^{17}$ are selected independently of each other from the group consisting of H and an organic residue selected from $C_1$ to $C_{12}$ alkyl and $C_1$ to $C_{12}$ heteroalkyl. Preferably, $R^{16}$ and $R^{17}$ are selected from H, $C_1$ to $C_6$ alkyl and $C_1$ to $C_4$ heteroalkyl, more preferably from H, linear $C_1$ to $C_4$ alkyl, isopropyl, —$CH_2OH$, —$CH_2$—$CH_2$—OH and —$CH_2$—$CH_2$—$NH_2$.

It was surprisingly found that a polymer according to the present invention comprising repeat units A and B is associated with all advantageous properties required to solve the object of the present invention. In particular, it was surprisingly found that the copolymer comprising repeat units A and B exhibits optimized antimicrobial activity and cell-compatibility with human cells (for overall positively charged polymers) and optimized antifouling (protein-repellent) activity and cell-compatibility with human cells (for overall zwitterionic polymers).

In an especially preferred embodiment, the repeat unit B is based on a compound having general formula (VIII) with $R^{16}$ and $R^{17}$ selected from linear $C_1$ to $C_4$ alkyl, —$CH_2OH$, —$CH_2CH_2OH$ or isopropyl, especially dimethylacrylamide (DMAA), dimethylmethacrylamide, or having the general formula (VII), especially hydroxyethylacrylate and hydroxymethylacrylate, and the repeat unit A is as defined above, wherein $R^1$ is a residue having the general formula (II) or (III) with m being 1 or 2, and all of $R^6$, $R^7$, $R^8$, $R^9$ and $R^{10}$ being identically H or $C_1$ to $C_4$ alkyl, $R^2$, if present, is an unsubstituted $C_1$ to $C_4$ alkyl, both $R^3$ and $R^4$ are H, and each of $X^1$, $X^2$, $Y^1$ and $Y^2$ is O. Especially preferred is a polymer comprising a repeat unit A, preferably having general formula (I-a) or (I-b), wherein $R^1$ is a residue having the general formula (II) or (III) with m being 2, and all of $R^6$, $R^7$, $R^8$, $R^9$ and $R^{10}$ being identically H, $R^2$ is an unsubstituted $C_1$ to $C_4$ alkyl, both $R^3$ and $R^4$ are H, and each of $X^1$, $X^2$, $Y^1$ and $Y^2$ is O in general formula (I), in combination with a repeat unit B derived from dimethylacrylamide (DMAA), dimethylmethacrylamide, hydroxyethylacrylate, hydroxymethylacrylate or N-isopropylacrylamide.

In another especially preferred embodiment, the repeat unit B is based on styrene as a co-monomer, in combination with a repeat unit A is as defined above, preferably having general formula (I-a) or (I-b), wherein $R^1$ is a residue having the general formula (II) or (III) with m being 2, and all of $R^6$, $R^7$, $R^8$, $R^9$ and $R^{10}$ being identically H, $R^2$, if present, is an unsubstituted $C_1$ to $C_4$ alkyl, both $R^3$ and $R^4$ are H, and each of $X^1$, $X^2$, $Y^1$ and $Y^2$ is O.

Preferably, the copolymer has a molecular weight of from 1000 g/mol to 1000000 g/mol, further preferred of from 2000 g/mol to 100000 g/mol, and especially preferred of from 3000 g/mol to 50000 g/mol.

In a preferred embodiment, the polymer according to the present invention is a copolymer consisting of repeat units A and B. Preferably, the molar ratio of repeat units A to repeat units B is from 99:1 to 1:99, preferably from 10:1 to 1:10, further preferred from 2:1 to 1:2, further preferred from 3:2 to 2:3, and especially preferred about 1:1.

Preferably, the overall molar fraction r of the different repeat units A (which are defined as $A_i$, wherein each $A_i$ is present at a molar fraction $r_i$) is from 0.01 to 0.99 and the overall molar fraction s of the different repeat units B (which are defined as $B_i$, where each $B_i$ is present at a molar fraction $s_i$) is from 0.01 to 0.99, wherein the sum of r and s is 1 (r+s=1) for each combination. Herein, r is defined as the sum of all the respective molar fractions $r_i$ ($r=\Sigma r_i$), wherein the molar fractions of the different repeat units $A_i$ are referred to as $r_i$, and the different versions of repeat unit A are referred to as $A_i$. Similarly, s is defined as the sum of all the respective molar fractions $s_i$ ($s=\Sigma s_i$), wherein the molar fractions of the different repeat units $B_i$ are referred to as $s_i$, and the different versions of repeat unit B are referred to as $B_i$. Further preferred, r is from 0.4 to 0.6 and s is from 0.4 to 0.6, wherein the sum of r and s is 1 for each combination. Especially preferred, both r and s are about 0.5 in the polymer according to the present invention.

Preferably, the polymer according to the present invention additionally comprises at least one repeat unit C comprising a crosslinking moiety. Preferably, a crosslinking moiety in repeat unit C is selected from a photo-crosslinking moiety and a thermally activated crosslinking moiety.

Herein, the term 'photo-crosslinking moiety' refers to a function that can be used to cross-link the polymer by radiation. Preferably, crosslinking is caused by irradiation with microwaves, NIR, visible or UV radiation, or the like, more preferably by irradiation with UV radiation. Suitable photo-crosslinking moieties are well-known to a person skilled in the art, e.g. from G. T. Hermanson, Bioconjugate Techniques, 3rd Edition, Academic Press, 2013, or V. V. Krongauz, A. D. Trifunac, Processes in Photo-reactive Polymers, Chapman & Hall, 1995; or Reiser/Arnost; Photoreactive Polymers: The Science and Technology of Resists, Wiley Interscience, 1989. Preferably, a photo-crosslinking moiety comprises a suitable photo-reactive group, e.g. a group comprising an aryl azide group (e.g. phenyl azides), an azide group, a diazo group, a diazirine group, a ketone group, a quinone group, an organic dye, or the like. Upon "activation" with an appropriate energy source, the photoreactive group generates an active species such as, e.g., a radical or biradical, including, for example, a nitrene, carbene, excited states of ketone, or the like.

Preferably, the photo-crosslinking moiety comprises an aryl ketone group, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photo-crosslinking moieties comprise quinone such as, for example, anthraquinone. The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (e.g., from a polymer, from a (pretreated) substrate and/or from a polymeric coating layer), thus creating a radical pair. Subsequent collapse of the radical pair leads to formation of a new carbon-carbon bond. If a reactive bond (e.g., carbon/hydrogen) is not available for bonding, the ultraviolet light-induced excitation of the benzophenone group is reversible and the molecule returns to ground state energy level upon removal of the energy source.

Alternatively, the photo-reactive crosslinking moiety may comprise a function selected from e.g. arylazide ($C_6R_5N_3$) such as phenyl azide and 4-fluoro-3-nitrophenyl azide; acyl azide (—CO—$N_3$) such as benzoyl azide and p-methylbenzoyl azide; azidoformate (—O—CO—$N_3$) such as ethyl azidoformate and phenyl azidoformate; sulfonyl azide (—$SO_2$—$N_3$) such as benzenesulfonyl azide; and phosphoryl azide $(RO)_2PON_3$ such as diphenyl phosphoryl azide and diethyl phosphoryl azide. Diazo compounds constitute another class of photo-reactive groups and include diazoalkanes (—$CHN_2$) such as diazomethane and diphenyldiazomethane; diazoketones (—C(=O)—$CHN_2$) such as diazoacetophenone and 1-trifluoromethyl-1-diazo-2-pentanone; diazoacetates (—O—C(=O)—$CHN_2$) such as t-butyl diazoacetate and phenyl diazoacetate; and beta-keto-alpha-diazoacetates (—C(=O)—$CN_2$—C(=O)—O—) such as t-butyl alpha diazoacetoacetate; etc. R may be preferably hydrogen or an alkyl as defined above. Other photo-reactive groups include the diazirines (—$CHN_2$) such as 3-trifluoromethyl-3-phenyldiazirine; and ketenes (—CH=C(=O)—) such as ketene and diphenylketene.

Advantageously, the inventive polymer comprising a repeat unit C with a photo-crosslinking moiety can be photo-crosslinked by itself. Thus, no external photo-crosslinker must be added. However, the inventive photo-crosslinkable polymer can also be used in combination with a suitable external photo-crosslinker, which may be selected from any suitable compound forming covalent bonds to a substrate and/or the polymer of the invention upon subjecting the compound to radiation, as defined above. For example, the inventive photo-crosslinkable polymer can be attached to the surface of a substrate by radiation if the surface of the substrate is previously provided with a suitable photo-crosslinker, for example $(EtO)_3$—Si—$CH_2$—$CH_2$—$CH_2$—O—$C_6H_4$—C(=O)—$C_6H_5$, or the like. Moreover, the inventive photo-crosslinkable polymer can also be used in combination with a suitable external thermo-crosslinker, as defined below.

The term 'thermally activated crosslinking moiety' refers to a function that can be used to cross-link the polymer by heat ('thermo-crosslinker'). Preferably, crosslinking is caused by heating in the range of from 40 to 200° C., more preferably in the range of from 60 to 120° C. In the context of the present invention, such a thermo-crosslinking moiety or thermo-crosslinker may be selected from any suitable compound forming covalent bonds to a substrate and/or the polymer of the invention upon subjecting the compound to heat treatment. Suitable thermo-crosslinking or thermo-setting groups are known in the art, e.g. from H. Dodiuk/S. Goodman, Handbook of Thermoset Plastics, 3rd Edition, 2013.

Advantageously, the inventive polymer comprising a repeat unit C with a thermo-crosslinking moiety can be thermally crosslinked by itself. Thus, no external thermo-crosslinker must be added. However, the inventive thermo-crosslinkable polymer can also be used in combination with a suitable external thermo-crosslinker, which may be selected from any suitable compound forming covalent bonds to a substrate and/or the polymer of the invention upon subjecting the compound to heat, as defined above. For example, the inventive thermo-crosslinkable polymer can be attached to the surface of a substrate by radiation if the surface of the substrate is previously provided with a suitable thermo-crosslinker, for example $Cl(Me)_2$-Si—$CH_2$—$CH_2$—$C_6H_4$—$SO_3$—$N_3$, or the like. Moreover, the inventive thermo-crosslinkable polymer can also be used in combination with a suitable external photo-crosslinker, as defined above.

To be able to react with a thermo-crosslinking moiety or a thermo-crosslinker, the polymer of the invention may have to be modified by a post-polymerization process in order to introduce suitable functional groups, for example a $C_6H_4$—$SO_3$—$N_3$ group, a vinyl group, a vinyl ether group, an acryloyl group, a methacryloyl group, or any other thermo-setting group known to those skilled in the art, e.g. as indicated in H. Dodiuk/S. Goodman, Handbook of Thermoset Plastics, 3rd Edition, 2013. For example, if any of the repeat units $A_i$ or $B_i$ carry a residue containing an alkyl hydroxy group, for example if $R_1$ or $R_2$ of any of the repeat units $A_i$ comprise an alkyl hydroxy group, or if any $B_i$ is 2-hydroxyethyl methacrylate, 2-hydroxyethyl acrylate, or the like, they may react with acryloyl chloride, methacryloyl chloride, vinyl chloride, allyl chloride, vinylbenzyl chloride, 2-(ethenyloxy)-1-methanesulfonate ethane diol, 2-e(ethenyloxy)-1-toluenesulfonate ethane diol, or the like, or any other reagent known to the skilled expert to introduce a vinyl, acryl or methacryl group into the polymer of the present invention by post-polymerization modification. The resulting modified polymer will then be thermo-crosslinkable without additional external crosslinker, and can be additionally surface-attached with a suitable thermo-crosslinker on a substrate, for example $C_1$—$Si(Me)_2$-$CH_2$—$CH_2$—$C_6H_4$—$SO_3$—$N_3$, or the like.

Advantageously, a polymer according to the present invention that comprises a repeat unit C comprising a crosslinking moiety can be (covalently) attached to a material or substrate, preferably comprising a C—H bond. Preferably, the material or substrate is a polymer material, or a material or substrate selected from glass, ceramic, metal, silicon (wafer), and the like, which has been optionally pre-treated (e.g. coated) with an organic moiety, preferably comprising a C—H bond.

Thereby, the polymer of the present invention that comprises a repeat unit C can be used, e.g., for coating the surface of another material, substrate or product, thus providing the coated surface of the other material, substrate or product with antimicrobial and/or antifouling properties. Further, the polymer of the invention may be crosslinked to form a crosslinked polymer network.

In preferred embodiments, the repeat unit C comprises a photo-crosslinking moiety, preferably, a photo-crosslinking moiety comprising a benzophenone group.

Preferably, the repeat unit C is represented by general formula (IX) as defined in the following.

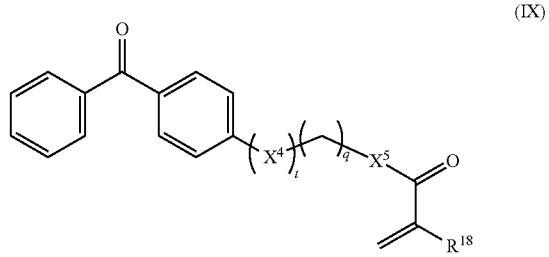

(IX)

In general formula (IX), $R^{18}$ is selected from H or an organic residue selected from $C_1$ to $C_{12}$ alkyl, $C_2$ to $C_{12}$ alkenyl, $C_2$ to $C_{12}$ alkynyl, $C_3$ to $C_{12}$ cycloalkyl, and $C_6$ to $C_{12}$ aryl. Preferably, $R^{18}$ is selected from H, or $C_1$ to $C_6$ alkyl, alkenyl, and alkynyl, and especially preferred from H, methyl, ethyl, or vinyl.

$X^4$ is selected from —O—, —S—, —NH—, —NR—, NR'—, —C(=O)—, —C(=S)—, —O—C(=O)—, —C(=O)—O—, —NH—C(=O)—, —NR—C(=O)—, —C(=O)—NH—, —C(=O)—NR—, —O—C(=O)—O—, —NH—C(=O)—NH—, —NR—C(=O)—NR—, —NH—C=NH—NH—, —NH—C=NR—NH, —NR—C=NH—NR—, and —NR—C=NR—NR—, wherein R represents a $C_1$ to $C_{30}$ alkyl residue and R' represents a $C_1$ to $C_{30}$ heteroalkyl residue, both as defined above. Preferably, $X^4$ is selected from —O—, —S—, —NH—, —NR—, —O—C(=O)—, —C(=O)—O—, —NH—C(=O)—, —NR—C(=O)—, —C(=O)—NH—, and —C(=O)—NR—, more preferably from —O—, —NH—, —O—C(=O)—, —C(=O)—O—, —NH—C(=O)—, and —C(=O)—NH—.

$X^5$ is selected from —O—, —NH—, and —NR—, wherein R represents a $C_1$ to $C_{30}$ alkyl residue, as defined above.

q is an integer of from 0 (zero) to 12, preferably from zero to 8, and especially preferred from zero to 6, and t is an integer from zero to 1, preferably zero.

In a preferred embodiment of the compound having general formula (IX), $R^{18}$ is H or methyl; $X^4$ is O, S, NH, NR, —C(=O)—, —C(=O)O—, —OC(=O)—, —C(=O)NH—, or —NHC(=O)—; $X^5$ is O or NH; and q is an integer from 1 to 4. In an even more preferred embodiment of the compound having the general formula (IX), $R^{18}$ is H or methyl, $X^4$ is O, NH, —C(=O)O—, —OC(=O)—, —C(=O)NH—, or —NHC(=O)—, $X^5$ is O or NH, and q is an integer from zero to 4 and t is one or zero. In an especially preferred embodiment of the compound having the general formula (IX), $R^{18}$ is H or methyl, $X^4$ is O, —C(=O)O— or —C(=O)NH—, $X^5$ is O, and q is from zero to 2, and t=zero. In another especially preferred embodiment of the compound having the general formula (IX), $R^{18}$ is H or methyl, $X^4$ is O, $X^5$ is NH, and q=t=zero.

Advantageously, a polymer according to the present invention that comprises a repeat unit C derived from a compound having general formula (IX) can be crosslinked upon irradiation with radiation in the UV region, preferably in the region of from 200 to 400 nm, more preferably from 254 to 365 nm. Thereby, the polymer of the present invention can be attached to a material or substrate, e.g. a polymer material, and/or used for coating the surface of another material, substrate or product.

Preferably, the polymer according to the present invention comprises at least one repeat unit A as defined above, optionally in combination with at least one repeat unit B as defined above, and at least one repeat unit C, wherein the repeat unit C comprises a crosslinking moiety.

Preferably, the at least one repeat unit C is comprised in the polymer of the present invention in a ratio of up to 20% (mol-%), preferably of from 0.005 to 20%, further preferred from 0.5 to 10%, and especially preferred from 1 to 5%. If the polymer according to the invention comprises more than one different repeat units C are present in, the different repeat units are referred to as $C_i$ in the following.

In an preferred embodiment, the polymer of the invention consists of repeat units $A_i$ and $C_i$, wherein the one or more repeat units $C_i$ are comprised in the polymer of the present invention in a ratio of up to 20%, preferably of from 0.005 to 20%, further preferred from 0.5 to 10%, and especially preferred from 1 to 5%, with the respective balance being made up by the repeat units $A_i$.

Preferably, the sum of the molar fractions of repeat units $C_i$ (defined as c) is from 0.005 to 0.200, the sum of the molar fractions of repeat units $A_i$ (defined as r) is from 0.01 to 0.99 and the sum of the molar fractions of repeat units B (defined as s) is from 0.01 to 0.99, wherein in each case the sum of c and r and s is 1 (c+r+s=1) for each combination. Herein, c is defined as the sum of all the respective molar fractions $c_i$ (c=Σ$c_i$) wherein the molar fractions of the different repeat units $C_i$ are referred to as $c_i$, and the different versions of repeat unit C are referred to as $C_i$. Similarly, r is defined as the sum of all the respective molar fractions $r_i$ (r=Σ$r_i$), wherein the molar fractions of the different repeat units $A_i$ are referred to as $r_i$, and the different versions of repeat unit A are referred to as $A_i$, and s is defined as the sum of all the respective molar fractions $s_i$ (s=Σ$s_i$), wherein the molar fractions of the different repeat units $B_i$ are referred to as $s_i$, and the different versions of repeat unit B are referred to as $B_i$. Further preferred, c is from 0.01 to 0.20, more preferably 0.01 to 0.05, while, independently, r is preferred from 0.1 to 0.9, more preferably from 0.4 to 0.6, and s is preferred from 0.1 to 0.9, more preferably from 0.4 to 0.6, wherein c+r+s=1 for each combination. Especially preferred, both r and s are about equimolar in the polymer according to the present invention, wherein the remainder of the polymer is constituted by repeat units C with c from 0.005 to 0.100, preferably from 0.01 to 0.10, and especially preferred from 0.01 to 0.05.

Preferably, the total number (x) of all repeat units A, (optionally) B, and (optionally) C in the polymer of the present invention is from 2 to 4500, further preferred from 5 to 450, and especially preferred from 10 to 100. Thus, the polymer of the present invention has a molar mass of at least M*2 g/mol, wherein M represents the average molar mass of all repeat units.

Preferably, the polymer of the present invention has a number average molecular weight $M_n$ of from 220 to 1,000,000 g/mol, more preferred from 2,200 to 100,000 g/mol, further preferred from 2,200 to 50,000 g/mol, and especially from 2,200 to 10,000 g/mol. In the context of this invention, the number average molecular weight $M_n$ of the polymer is determined by gel permeation chromatography, which is calibrated with a polymer standard that is soluble in an appropriate solvent that also dissolves the inventive polymer, for example poly(methyl methacrylate) in chloroform, poly(ethylene oxide) in aqueous solution, poly(methylmethacrylate) in trifluoroethanol, etc. The same method is also used for modified polymers of the present invention, such as, e.g. the polymer with appropriate protective groups, and the like.

In the gel permeation chromatography measurements for determining the number average molecular weight $M_n$ of the polymer of the present invention, typical GPC conditions are used, e.g. SDV columns or GRAM columns (available from Polymer Standard Services, Mainz, Germany) for chloroform or tetrahydrofuran; Suprema or Novema columns (available from Polymer Standard Services, Mainz, Germany) for aqueous solutions; Suprema or Novema columns (available from Polymer Standard Services, Mainz, Germany) for trifluoroethanol. Typical flow conditions are from 0.5 to 1 ml/min, wherein an appropriate salt may be optionally added to aqueous solvents and trifluoroethanol as needed.

In another aspect of the present invention, the present invention provides the use of the inventive antimicrobial and/or antibiofouling (protein-repellent) polymer for preventing microbial growth and/or biofouling. Particularly preferred, the present invention provides the use of the inventive polymer for inhibiting the growth of bacteria and other pathogens (e.g. fungi), thereby preferably exhibiting a low toxicity to human cells. This allows for the use of the polymer of the present invention (or of compositions comprising the same) for the treatment and/or prevention of microbial infections in a (human) patient. Detailed examples are described below.

Preferably, the inventive antimicrobial and/or antibiofouling polymer exhibits a significant growth reduction of bacterial pathogens of at least about 7%, preferably at least about 70%, more preferably at least about 80%, even more preferably at least about 90%, likewise even more preferably at least about 95, 96, 97, 98, 99 or 99.99%, preferably of $E.$ $coli$, $P.$ $aeruginosa$, $K.$ $pneumoniae$, $S.$ $aureus$, $S.$ $epidermidis$, and $E.$ $faecalis$ and other pathogens. In solution, this is preferably determined by a minimum inhibitory concentration assay as defined below. On surfaces, this is preferably determined by the spray assay defined below.

In another aspect of the present invention, the present invention provides monomers to be used in a method of producing the polymer according to the present invention. The polymer of the present invention can be produced by a polymerization reaction using the respective monomers.

The monomers of the present invention are derived from itaconic acid or its thiocarboxylic acid analogues (i.e. comprising the corresponding carbothioic O and/or S acid groups) and are characterized by comprising at least one residue that is an organic residue comprising at least one cationic moiety having at least one positive charge, in particular an organic residue $R^1$ as defined above.

Preferably, a monomer for the repeat unit A is represented by one of general formulae (X-a), (X-b), (X-c), (X-d), (X-e), and (X-f), wherein $R^1$, $R^2$, $R^3$, $R^4$, $X^1$, $X^2$, $Y^1$, and $Y^2$ are defined as for general formulae (I-a), (I-b), (I-c), (I-d), (I-e) and (I-f) above.

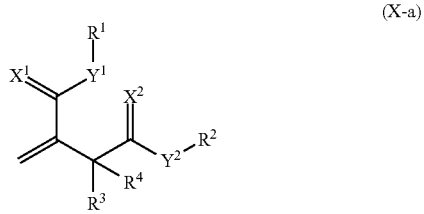
(X-a)

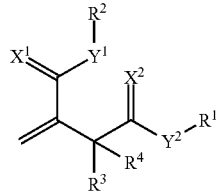
(X-b)

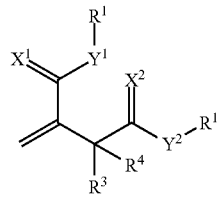
(X-c)

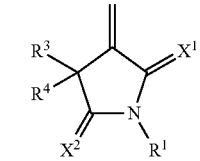
(X-d)

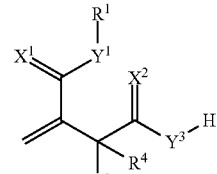
(X-e)

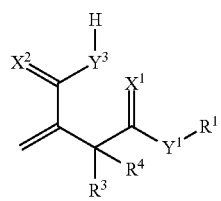
(X-f)

In general formulae (X-a), (X-b), (X-c), (X-d), (X-e), and (X-f), $R^1$ is an optionally substituted organic residue that comprises at least one cationic moiety having at least one positive charge; $R^2$ is an optionally substituted organic residue; $R^3$ and $R^4$ each represent independently from each other H or an optionally substituted organic residue; $X^1$ and $X^2$ are selected independently of each other from O or S; and $Y^1$ and $Y^2$ are selected independently of each other from O, S, NH, $NR^5$ or $PR^5$, wherein $R^5$ is $C_1$ to $C_{12}$ alkyl as defined above.

In formulae (X-e) and (X-f), the group $-C(=X^2)-Y^2-H$ may be present in its deprotonated form depending on environmental conditions, such as, e.g. adjacent groups, pH, ions contained in the environment, etc. Thus, the corresponding group $-C(=X^2)-Y^2-H$ may be represented by $-C(=O)O^-$, $-C(=O)S^-$, $-C(=S)O^-$, or $-C(=S)S^-$, respectively. Optionally, these deprotonated groups may be conjugated with a suitable counterion, which may be a mono- or multivalent organic or inorganic cation. Preferred examples of suitable cations comprise alkali metal cations, such as, e.g., Na+, K+, etc., ammonium ions, such as, e.g., $NH_4^+$, $N(R^5)_4^+$, etc.

In general formulae (X-a), (X-b), (X-c), (X-d), (X-e), and (X-f), $R^2$ preferably represents an organic residue, which is selected from an optionally substituted organic residue selected from the group consisting of linear or branched $C_1$ to $C_{30}$ alkyl, linear or branched $C_2$ to $C_{30}$ alkenyl, linear or branched $C_2$ to $C_{30}$ alkynyl, $C_3$ to $C_{30}$ cycloalkyl, $C_4$ to $C_{30}$ cycloalkenyl, $C_5$ to $C_{30}$ cycloalkynyl, $C_6$ to $C_{30}$ aryl, linear or branched $C_7$ to $C_{30}$ arylalkyl, linear or branched $C_1$ to $C_{30}$ heteroalkyl, linear or branched $C_2$ to $C_{30}$ heteroalkenyl, linear or branched $C_2$ to $C_{30}$ heteroalkynyl, $C_3$ to $C_{30}$ heterocycloalkyl, $C_3$ to $C_{30}$ heterocycloalkenyl, $C_4$ to $C_{30}$ heterocycloalkynyl, $C_5$ to $C_{30}$ heteroaryl, and linear or branched $C_6$ to $C_{30}$ heteroarylalkyl.

Preferably, $R^3$ and $R^4$ in general formulae (X-a), (X-b), (X-c), (X-d), (X-e), and (X-f) are selected independently of each other from the group consisting of H, $C_1$ to $C_{12}$ alkyl, $C_3$ to $C_{30}$ cycloalkyl, $C_1$ to $C_{12}$ heteroalkyl, $C_5$ to $C_{12}$ heterocycloalkyl, $C_6$ to $C_{12}$ aryl and $C_5$ to $C_{12}$ heteroaryl, wherein the respective residues are as defined above. Preferably, the $C_1$ to $C_{12}$ heteroalkyl is $C_1$ to $C_{12}$ alkoxy. Preferably, $R^3$ and $R^4$ are selected from the group consisting of H and $C_1$ to $C_3$ alkyl. Especially preferred, both $R^3$ and $R^4$ are H.

In general formulae (X-a), (X-b), (X-c), (X-d), (X-e), and (X-f), $X^1$ and $X^2$ are selected independently of each other from O or S. Preferably, both $X^1$ and $X^2$ are O.

In general formulae (X-a), (X-b), (X-c), (X-d), (X-e), and (X-f), $Y^1$ and $Y^2$ are selected independently of each other from O, S, NH, $NR^5$ or $PR^5$, wherein $R^5$ is $C_1$ to $C_{12}$ alkyl as defined above. Preferably, $R^5$ is $C_1$ to $C_5$ alkyl, more preferably $C_1$ to $C_3$ alkyl. Preferably, $Y^1$ and $Y^2$ are O or NH. In preferred embodiments, both $Y^1$ and $Y^2$ are O, or both $Y^1$ and $Y^2$ are NH, or one of $Y^1$ and $Y^2$ is O, and the other one is NH. In an especially preferred embodiment, both $Y^1$ and $Y^2$ are O.

Preferably, $R^1$ in general formulae (X-a), (X-b), (X-c), (X-d), (X-e), and (X-f) is an organic residue that comprises at least one cationic moiety having at least one positive charge, wherein the at least one positive charge is located at a heteroatom, further preferred at a nitrogen atom, a sulfur atom or a phosphorous atom, and especially preferred at a nitrogen atom.

Preferably, the at least one positive charge is located at a nitrogen atom which is a substituent, e.g. in form of a $—N^+H_3$ or $=N^+H_2$ group, or which is part of a linear or branched chain, e.g. in form of a $—N^+H_2R$, $—N^+H(R')R—$, or $—N+(R')_2R—$ group (with R and R' independently of each other being selected from an organic residue as defined herein), or which is part of a (partly) unsaturated or aromatic ring, e.g. an azolium ring, am imidazolium ring, a pyrazolium ring, a pyridinium ring, and the like. Especially preferred, the at least one positive charge is located at an ammonium nitrogen atom.

In especially preferred embodiments, $R^1$ is a $C_1$ to $C_{30}$ heteroalkyl, $C_1$ to $C_{30}$ heteroalkenyl, $C_1$ to $C_{30}$ heteroalkynyl, $C_1$ to $C_{30}$ heteroaryl, or $C_1$ to $C_{30}$ heteroarylalkyl selected from the group consisting of residues having one of the general formulae (II), (III), (IV), (V) or (VI) as defined above.

In general formulae (II), (III), (IV) and (V), the residues $R^6$, $R^7$, $R^8$, $R^9$, $R^{10}$, $R^{11}$ and $R^{12}$ represent independently from each other H or an organic residue selected from linear, branched, cyclic, saturated, partially saturated and/or unsaturated $C_1$ to $C_{12}$ alkyl, $C_2$ to $C_{12}$ alkenyl, $C_2$ to $C_{12}$ alkynyl, $C_3$ to $C_{12}$ cycloalkyl, $C_4$ to $C_{12}$ cycloalkenyl, $C_5$ to $C_{12}$ cycloalkynyl, $C_1$ to $C_{12}$ heteroalkyl, $C_2$ to $C_{12}$ heteroalkenyl, $C_2$ to $C_{12}$ heteroalkynyl, $C_3$ to $C_{12}$ heterocycloalkyl, $C_4$ to $C_{12}$ heterocycloalkenyl, $C_5$ to $C_{12}$ heterocycloalkynyl, $C_6$ to $C_{12}$ aryl, $C_7$ to $C_{12}$ arylalkyl, $C_5$ to $C_{12}$ heteroaryl, and $C_6$ to $C_{12}$ heteroarylalkyl group, which may be optionally substituted.

In general formulae (II), (III), (IV) and (V), $R^6$, $R^7$, $R^8$, $R^9$, $R^{10}$, $R^{11}$ and $R^{12}$ are preferably H or $C_1$ to $C_6$ alkyl, and especially preferred H or $C_1$ to $C_4$ alkyl.

In general formula (II) and (III), m is preferably an integer from 1 to 4, more preferably 1 or 2, and especially preferred m=2.

In general formula (IV) and (V), p is preferably an integer from 1 to 4, more preferably 1 or 2, and especially preferred p=1.

Alternatively, the monomer compound represented by general formulae (X-a), (X-b), (X-c), (X-d), (X-e), and (X-f) comprises a precursor of an organic residue comprising at least one cationic moiety having at least one positive charge. Preferably, the compound having general formulae (X-a), (X-b), (X-c), (X-d), (X-e), or (X-f) may comprise a precursor moiety for a cationic moiety, which is protected by one or more appropriate protective group(s).

For example, for certain embodiments of the repeat unit A having general formulae (I-a), (I-b), (I-c), (I-d), (I-e), and (I-f) that comprises a residue $R^1$ in form of one of the residues having the general formula (II), (III), (IV) or (V) as defined above, wherein $R^6$, $R^7$, $R^8$, $R^9$, $R^{10}$, $R^{11}$ and/or $R^{12}$ are equal to H, the corresponding residue $R^1$ of the monomer compound having general formulae (X-a), (X-b), (X-c), (X-d), (X-e), or (X-f) needs to be protected by an appropriate protective group in order to be polymerizable.

For these embodiments, the monomer for the repeat unit A, which monomer is represented by general formulae (X-a), (X-b), (X-c), (X-d), (X-e), and (X-f), comprises a residue $R^1$ represented by a general formula selected from general formulae (II-P), (III-P), (IV-P) and (IV-P) as defined in the following.

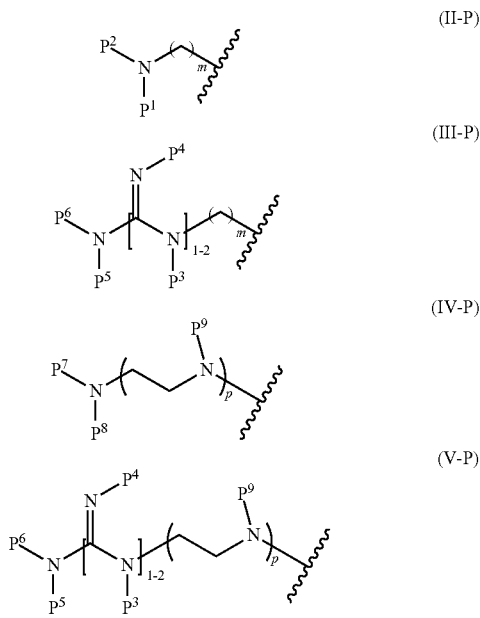

In general formulae (II-P), (III-P), (IV-P), and (V-P), m and p are as defined for formulae (II) and (III), and (IV) and (V), respectively. In general formulae (II-P) and (III-P), m is an integer from 0 to 12, preferably an integer from 1 to 4, more preferably 1 or 2, and especially preferred m=2. In general formula (IV-P) and (V-P), p is an integer from 1 to 12, preferably an integer from 1 to 4, more preferably 1 or 2, and especially preferred p=1.

In general formulae (II-P), (III-P), (IV-P), and (V-P), the residues $P^1$, $P^2$, $P^3$, $P^4$, $P^5$, $P^6$, $P^7$, $P^8$ and $P^9$ represent, independently of each other, H, $C_1$ to $C_6$ alkyl or a suitable protective group that can be cleaved off after the polymerization of the monomer having general formula (X-a), (X-b), (X-c), (X-d), (X-e) or (X-f) to convert the residues of formulae (II-P), (III-P), (IV-P) or (V-P) to the respective residue of formula (II), (III), (IV) or (V), respectively, as defined for general formulae (I-a), (I-b), (I-c), (I-d), (I-e) and (I-f).

$P^1$, $P^2$, $P^3$, $P^4$, $P^5$, $P^6$, $P^7$, $P^8$ and $P^9$ may be selected from any protective groups known to the skilled expert that can be incorporated into the monomer of general formula (X-a), (X-b), (X-c), (X-d), (X-e) or (X-f) without damaging its structural integrity. Further, $P^1$, $P^2$, $P^3$, $P^4$, $P^5$, $P^6$, $P^7$, $P^8$ and $P^9$ can be removed after the homopolymerization or copolymerization of the monomer of general formula (X-a), (X-b), (X-c), (X-d), (X-e) or (X-f) from the resulting homopolymer or copolymer, without damaging the structural integrity of that polymer.

Suitable protective groups known to the skilled expert can be found, for example, in *Greene's Protective Groups in Organic Synthesis*, Fifth Ed., Wuts, P. G., Ed., Wiley, New York: 2014. Preferably, $P^1$, $P^2$, $P^3$, $P^4$, $P^5$, $P^6$, $P^7$, $P^8$ and $P^9$ are independently of each other selected from H, a $C_1$ to $C_4$ alkyl group, a tert-butyloxycarbonyl (Boc) group, a 9-fluorenylmethyloxycarbonyl (FMOC) group, and a carbamate group. Especially preferred, $P^1$, $P^2$, $P^3$, $P^4$, $P^5$, $P^6$, $P^7$, $P^8$ and $P^9$ are H or Boc groups.

Any of $P^1$, $P^2$, $P^3$, $P^4$, $P^5$, $P^6$, $P^7$, $P^8$ and $P^9$ that are used to protect the same nitrogen atom (i.e. $P^1$ and $P^2$, or $P^5$ and $P^6$, or $P^7$ and $P^8$, respectively) may be linked and form a protective group that substitutes both H atoms attached to the N atom. Preferably, such protective group is a phthalimide group.

The monomer represented by the general formula (X-a), (X-b), (X-c), (X-d), (X-e) or (X-f) may be derived from itaconic acid or its anhydride. Itaconic acid is the trivial name for 2-methylene butane-1,4-dicarboxylic acid. The chemistry and polymerization behavior of itaconic acid and its anhydride are well-known in the art. Itaconic acid is a dicarboxylic acid that can be polymerized by radical polymerization. Several initiators, including potassium peroxodisulfate, dibenzoyl peroxide, and azoisobutyric acid nitrile have since then been reported as initiators for the radical polymerization of itaconic acid (cf. e.g. Braun and Sayed, Die Makromolekulare Chemie 1966, 96(1), 100; Hirano, Higashi, Seno, Sato, Journal of Polymer Science, Part A: Polymer Chemistry (2004), 42(19), 4895-4905; Hirano, Higashi, Seno, Makiko, Sato, European Polymer Journal (2003), 39(9), 1801-1808, Katime, Palomares, Cesteros, Laborra, Dominguez, Thermochimica Acta (1988), 132, 193-203; Katime, Palomares, Cesteros, Laborra, Dominguez, Thermochimica Acta (1989), 142(2), 317-28; Katime, Madoz, Velada, Thermochimica Acta (1993), 220 (1-2), 91-101). Important references of the patent literature include U.S. Pat. No. 3,560,529, which describes the polymerization of itaconic anhydride using a mixed itaconic-acyl peroxide; U.S. Pat. No. 3,055,873, which describes the polymerization of monoalkyl itaconate at 60° C. using 0.5% dibenzoyl peroxide as initiator (75% conversion after only 2 hours); and U.S. Pat. No. 5,223,592, which describes the polymerization of neutralized itaconic acid at 90° C. using sodium peroxodisulfate as initiator, and feeding the initiator and monomer solutions linearly over 2 hours, which gave about 98% conversion, even though the obtained molecular masses $M_n$, determined by gel permeation chromatography, were low.

One special feature of itaconic acid is that, being a side product in the Krebs cycle, it is non-toxic for humans. Industrially, itaconic acid is produced by fermentation of carbohydrates, e.g. molasses, using microorganisms (e.g. *Aspergillus*). Polyitaconic acid derivatives are currently used in shampoos (sulfonated polyitaconic acid), the polyitaconic esters are used as plastics, glues and coatings, artificial gems and glasses, and dental materials (cf. e.g. Okabe et al., Appl. Microbiol. Biotechnol. 2009, 84(4), 597; Haijan et al., Current Research Journal of Biological Sciences 2015, 7(2), 37).

In summary, itaconic acid and its derivatives are a cheap, non-toxic and sustainable starting material and thus an ideal candidate for the synthesis of polymers that are intended for use in medical products. The itaconic-acid based bioactive polymers of the present invention are either antimicrobially active or antifouling/protein-repellent (i.e. they prevent biofilm formation), or both, as specified in the claims and examples.

A monomer for repeat unit A represented by general formula (X-a), (X-b), (X-c), (X-d), (X-e) or (X-f) can be prepared, e.g., by addition of corresponding residues to itaconic acid or an itaconic acid derivative, respectively. Suitable reactions result in the formation of a corresponding ester, amide, etc., function connecting the respective residues to itaconic acid or the itaconic acid derivative, such as, e.g., itaconic acid anhydride, or the like. Suitable reactions for producing the respective linkage on basis of an ester, amide, or the like, are well-known to a person skilled in the art of synthetic organic chemistry, for example as described in R. Brückner, Reaktionsmechanismen, $3^r$ Ed., Spektrum Akademischer Verlag, 2009.

For example, the residue $R^1$ or $R^2$ can be introduced by nucleophilic substitution, or another (catalyzed) substitution reaction. For example, an alcohol, such as, e.g., methanol, ethanol, propanol, n-butanol, and the like, can be used to prepare a hydrophobic alkyl residue $R^2$ by formation of an ester bond with itaconic acid or a derivative thereof.

For example, a boc-protected ω-aminoalcohol, such as, e.g., N-boc-2-aminoethanol, a boc-protected ω-guanidinioalcohol, a boc-protected ω-biguanidinioalcohol, and the like, can be used to prepare a residue $R^1$ represented by general formula (II) or (III), respectively, by formation of an ester bond with itaconic acid or a derivative thereof. The so-formed residue having general formula (II-P) or (III-P), respectively, can then be converted to a corresponding organic residue that comprises at least one cationic moiety having at least one positive charge represented by general formula (II) or (III), respectively, in a subsequent step of removing the protective group boc by a suitable reaction (e.g. reaction with trifluoroethanol, hydrochloric acid, or the like).

Optionally, a suitable catalyst may be used in the respective substitution reaction. Suitable catalysts are well-known to a person skilled in the art. For example, an acid catalyst can be used in an esterification reaction, such as, e.g., an inorganic acid, e.g., HCl, $H_2SO_4$, or the like, and a base catalyst can be used in an amidification reaction, such as, e.g., 4-dimethylaminopyridine (DMAP), or the like, etc.

For example, an ω-boc-amino alkylamine, such as, e.g., ω—N-boc-2-amino ethylamine, or a boc-protected ω-guanidinio alkylamine, or a boc-protected ω-biguanidinio alkylamine, and the like, can be used to prepare a residue $R^1$ represented by general formula (II) or (III) by formation of an amine bond with itaconic acid or a derivative thereof. The so-formed residue can then be converted to a corresponding organic residue that comprises at least one cationic moiety having at least one positive charge represented by general formula (II) or (III) in a subsequent step of removing the protective group boc by a suitable reaction (e.g. reaction with trifluoroethanol or hydrochloric acid).

For example, a boc-protected ω-aminoalcohol, such as, e.g., N-boc-2-aminoethanol, or a boc-protected ω-guanidinioalcohol, or a boc-protected ω-biguanidinioalcohol, and the like, can be used to prepare a residue $R^1$ represented by general formula (II-P) or (III-P) by formation of a C—N with the itaconic imide. The so-formed residue can then be converted to a corresponding organic residue $R^1$ that comprises at least one cationic moiety having at least one positive charge represented by general formula (II) or (III) in a subsequent step of removing the protective group boc by a suitable reaction (e.g. reaction with trifluoroethanol or hydrochloric acid).

For example, a hydrophobic alkyl can be attached to the cyclic imide of itaconic acid e.g. in a Mitsunobu reaction (e.g. in the presence of diethylazodicarboxylate and $PPh_3$). For example, an alcohol, such as, e.g., methanol, ethanol, propanol, n-butanol, and the like, can be used to introduce the hydrophobic alkyl group by forming a C—N bond in the imide. Preferably, a hydrophobic alkyl imide compound can be used as a co-monomer for repeat unit B in the polymer according to the present invention.

Preferably, an optional co-monomer for repeat unit B is selected from a group consisting of vinyl ether, styrene or styrene derivatives, N-vinylpyrrolidone, vinyl chloride, vinyl acetate, vinylpyridine, vinylpyridinium ions or salts, a compound having general formula (VII) and a compound having general formula (VIII) as specified above. Preferably, a vinyl ether is a $C_1$ to $C_{12}$ alkyl, alkenyl, or alkynyl vinyl ether, more preferably $C_2$ alkyl, alkenyl, or alkynyl vinyl ether.

Further, itaconic acid, its sulfur containing analogues or its respective derivatives may also be used as co-monomer for repeat unit B, as long as the respective monomer is not a monomer represented by one of general formulae (X-a), (X-b), (X-c), (X-d), (X-e) and (X-f). Preferred examples of such optional co-monomers comprise e.g. itaconic acid, its anhydride, or a derivative of itaconic acid, as represented by general formula (X-c), (X-d), (X-e) or (X-f), wherein each residue $R^1$ is substituted by a residue $R^2$, and wherein all of $R^3$, $R^4$, $X^1$, $X^2$, $Y^1$, $Y^2$ and $Y^3$ are as defined for general formulae (X-c), (X-d), (X-e) and (X-f). Especially preferred examples comprise the mono and di $C_1$ to $C_4$ alky esters or amides of itaconic acid as well as the $C_1$ to $C_4$ alkyl imides of itaconic acid.

Monomers represented by general formulae (VII) and (VIII) are commercially available or can be prepared by suitable addition reaction well-known to a person skilled in the art.

Preferably, an optional co-monomer used to introduce repeat unit C into the inventive polymer is a compound, which comprises a crosslinking moiety, preferably a photo-crosslinking moiety and/or a thermo-crosslinking moiety, and a moiety for polymerization with the monomers for repeat units A and B. Preferably, a moiety for polymerization with the monomers for repeat units A and B comprises a polymerizable double bond, especially preferred a vinyl, acrylate, methacrylate or styreneresidue. More preferably, the moiety for polymerization with the monomers for repeat units A and B is a vinylether, acrylate, methacrylate or styrene derivative.

Preferably, a co-monomer for repeat unit C is represented by general formula (XI) as defined below.

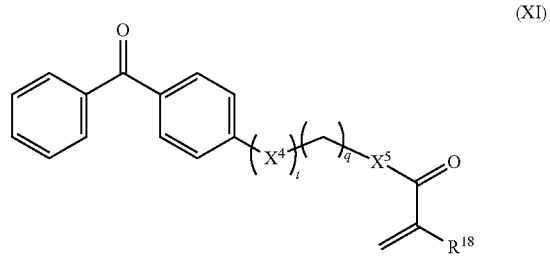

(XI)

In general formula (XI), $R^{18}$, $X^4$, $X^5$ and q and t are as defined for general formula (IX) above.

In particular, $R^{18}$ is selected from H or an organic residue selected from $C_1$ to $C_{12}$ alkyl, $C_2$ to $C_{12}$ alkenyl, $C_2$ to $C_{12}$ alkynyl, $C_3$ to $C_{12}$ cycloalkyl, and $C_6$ to $C_{12}$ aryl. Preferably, $R^{18}$ is selected from H, or $C_1$ to $C_6$ alkyl, alkenyl, and alkynyl, and especially preferred from H, methyl, ethyl, or vinyl.

$X^4$ is selected from —O—, —S—, —NH—, —NR—, NR'—, —C(=O)—, —C(=S)—, —O—C(=O)—, —C(=O)—O—, —NH—C(=O)—, —NR—C(=O)—, —C(=O)—NH—, —C(=O)—NR—, —O—C(=O)—O—, —NH—C(=O)—NH—, —NR—C(=O)—NR—, —NH—C=NH—NH—, —NH—C=NR—NH, —NR—C=NH—NR—, and —NR—C=NR—NR—, wherein R represents a $C_1$ to $C_{30}$ alkyl residue and R' represents a $C_1$ to $C_{30}$ heteroalkyl residue, both as defined above. Preferably, $X^4$ is selected from —O—, —S—, —NH—, —NR—, —O—C(=O)—, —C(=O)—O—, —NH—C(=O)—, —NR—C(=O)—, —C(=O)—NH—, and —C(=O)—NR—, more preferably from —O—, —NH—, —O—C(=O)—, —C(=O)—O—, —NH—C(=O)—, and —C(=O)—NH—.

$X^5$ is selected from —O—, —NH—, and —NR—, wherein R represents a $C_1$ to $C_{30}$ alkyl residue, as defined above.

q is an integer of from 0 to 12, preferably from 0 to 8, and especially preferred from 0 to 6.

t is zero or 1, preferably zero.

A co-monomer for repeat unit C represented by general formula (XI) can be prepared, e.g., by addition of a benzophenone-comprising compound having a reactive group, such as, for example an alcohol group, an amine group, or the like, to an acrylic acid molecule or an acrylic acid derivative compound, respectively. Appropriate addition reactions for producing the respective linkage on basis of an ester, amide, or the like, are well-known to a person skilled in the art.

Alternative preparation methods are described, e.g., in WO2015/197472, WO2014/123706, US200100/227076, or in "Acylation of 2-phenoxyethyl esters of 2-methyl- and 3-phenyl-2-propenoic acids" by Lukac, Ivan et al., Collection of Czechoslovak Chemical Communications, 49(11), 2635-7; 1984.

In another aspect of the present invention, the present invention provides a method of producing the polymer according to the present invention using the monomer according to the present invention.

The polymer according to the present invention can be produced by a known polymerization reaction from at least one monomer represented by the general formula (X-a), (X-b), (X-c), (X-d), (X-e) and (X-f), optionally in combination with at least one monomer (co-monomer) selected from the group consisting of vinyl ether, styrene or styrene derivatives, N-vinylpyrrolidone, vinyl chloride, vinyl acetate, vinylpyridine, vinylpyridinium ions or salts, a compound represented by general formula (VII), a compound represented by general formula (VIII), a compound represented by general formula (XI), each as defined above, itaconic acid, its sulfur containing analogues or its respective derivatives, as long as the respective monomer compound is not a monomer represented by one of general formulae (X-a), (X-b), (X-c), (X-d), (X-e) and (X-f). Preferably, a vinyl ether is a $C_1$ to $C_{12}$ alkyl, alkenyl, or alkynyl vinyl ether, more preferably $C_2$ alkyl, alkenyl, or alkynyl vinyl ether.

Preferably, the reaction is carried out by providing the at least one monomer represented by general formula (X-a), (X-b), (X-c), (X-d), (X-e) and (X-f) as well as all co-monomers, as required, in admixture, starting the polymerization reaction to polymerize the monomers and optional co-monomers, and recovering the product polymer.

In case of the production of a co-polymer, the monomer(s) represented by general formula (X-a), (X-b), (X-c), (X-d), (X-e) and (X-f) and the respective co-monomer(s) are provided in a predetermined molar ratio to obtain the desired composition of repeat units in the polymer to be produced. For the monomers of the present invention, statistical, statistical to alternating, alternating or gradient polymers may be obtained. In case of sequential monomer addition, gradient block copolymers or block copolymers may be obtained.

In case of the production of a co-polymer consisting of repeat units A and B as defined above, the ratio of monomers for repeat units A to monomers for repeat units B is from 99:1 to 1:99, preferably from 10:1 to 1:10, further preferred from 2:1 to 1:2, further preferred from 3:2 to 2:3, and especially preferred about 1:1.

In case of the production of a co-polymer consisting of repeat units A and C as defined above, the monomer for repeat unit C is comprised in the reaction mixture in a ratio of up to 20% (mol-%) with respect to the content of monomers for repeat unit A, preferably of from 0.005 to 20%, further preferred from 0.5 to 10%, and especially preferred from 1 to 5%.

In case of the production of a co-polymer consisting of repeat units A, B and C as defined above, the monomer for repeat unit C is comprised in the reaction mixture in a ratio of up to 20% (mol-%) with respect to the total content of monomers for repeat units A and B, preferably of from 0.005 to 20%, further preferred from 0.5 to 10%, and especially preferred from 1 to 5%.

Preferably, the polymerization reaction is a radical polymerization reaction or a group transfer polymerization.

Preferably, the polymerization reaction is carried out in bulk, in a solvent or in a solvent mixture, wherein the monomers are dissolved prior to starting the reaction or added to the solvent during the polymerization reaction. The solvent may be any solvent know to the skilled expert as a solvent that tolerates radical polymerization or group transfer polymerization, and has the appropriate solubility for the chosen mixture of monomers and/or protected monomers. Preferred solvents are selected from the group consisting of water, methanol, ethanol, propanol, isopropanol, DMF, DMSO, benzene, toluene, acetone, 2-butanone, or the like, and mixtures thereof.

Preferably, the monomers are dissolved in the solvent or solvent mixture with a total concentration of from 0.01 g/ml to bulk, preferably about 0.5 g/ml. Herein, the term 'total concentration' refers to the concentration of all monomers represented by the general formulae (X-a), (X-b), (X-c), (X-d), (X-e) and (X-f) as well as optional co-monomers.

Preferably, the radical polymerization reaction is initiated using a radical starter (initiator). Suitable radical starters or initiators that can be used for controlled radical polymerization are known to the skilled expert, for example from Matyjaszewski/Davis, Handbook of Radical Polymerization, Wiley interscience, 2002. Preferably, a radical starter is selected from sodium or potassium peroxodisulfate, dibenzoyl peroxide, and azoisobutyric acid nitrile (AIBN), 3-halogeno-3-methyl-2-buntanone, preferably 3-bromo-3-methyl-2-buntanone, benzyl halogenide, preferably, benzyl chloride, and the like.

Preferably, the radical polymerization reaction is carried out in the presence of a suitable catalyst or activity moderator that induces controlled radical polymerization instead of the above described free radical polymerization.

In such cases, the polymerization either is a reversible addition fragmentation chain transfer (RAFT) radical polymerization, atom transfer radical polymerization (ATRP), or nitrogen mediated radical polymerization (NMP), for example as described by Z. Szablan, A. A. Toy, A. Terrenoire, T. P. Davis, M. H. Stenzel, A. H. E. Muller, C. Barner-Kowollik, Journal of Polymer Science, Part A: Polymer Chemistry 2006, 44, 3692-3710, or Z. Szablan, A. A. Toy, T. P. Davis, X. Hao, M. H. Stenzel, C. Barner-Kowollik, Journal of Polymer Science, Part A: Polymer Chemistry 2004, 42, 2432-2443. Alternatively, the polymerization is a group transfer radical polymerization, e.g. as described by Kassi, Constantinou, Patrickios, European Polymer Journal (2013), 49(4), 761-767.

For example, cumyl dithiobenzoate, cumyl phenyl dithioacetate, 2-cyanoprop-2-yl-dithiobenzoate, 4-cyanopentanoic acid dithiobenzoate, and S-methoxycarbonylphenylmethyl dithiobenzoate can be used as RAFT agents; the CuCl/methyl benzoate/N,N,N',N",N"-pentamethyldiethylenetriamine/cyclohexanone system for ATRP, and SG1 for NMP.

Using such a initiator/catalyst system advantageously allows to control the molar mass and polydispersity of the polymer produced.

Preferably, the polymerization reaction is carried out at a temperature of from 25° C. to 120° C., more preferably 40° C. to 90° C., and even more preferably from 50° C. to 80° C., especially preferably from 60 to 70° C.

Preferably, the polymerization reaction is carried out at a pressure of from atmospheric pressure to 10 bar.

Preferably, the polymerization reaction is carried out for a duration of from 30 min to 1 week.

Preferably, the polymerization reaction is carried out under a protective atmosphere, e.g., under nitrogen, argon, or the like.

In case the residues $R^1$ of the monomer represented by the general formulae (X-a), (X-b), (X-c), (X-d), (X-e) and (X-f) comprise a protective group as in general formulae (II-P), (III-P), (IV-P) and (V-P), the production method additionally comprises a step of removing the protective group(s) in order to obtain the respective residue comprising at least one cationic moiety having at least one positive charge.

Preferably, the step of removing the protective group(s) is carried out after the step of polymerizing the monomers.

The step of removing the protective group(s) is carried out following standard procedures for the respective protective group known in the art, e.g. from *Greene's Protective Groups in Organic Synthesis*, Fifth Ed., Wuts, P. G., Ed., Wiley, New York: 2014.

For example, Boc protective groups can be removed from a polymer comprising corresponding Boc-protected repeat units A by dissolving the polymer in an appropriate amount of solvent, e.g. methanol (anhydrous) or dicloromethane, and adding an acid, such as, e.g., trifluoroacetic acid (TFA), HCl, optionally dissolved in a suitable solvent, such as, e.g. 1,4-dioxane, or the like, in an appropriate amount.

In another aspect of the present invention, the present invention provides a polymer produced by the method of producing a polymer according to the present invention.

The polymer produced by the method of producing a polymer according to the present invention is a polymer according to the present invention, as defined above.

In another aspect of the present invention, the present invention provides a use of the polymer according to the present invention and products prepared using the polymer according to the present invention.

Advantageously, the polymer according to the present invention can be used to provide antimicrobial and/or antifouling (protein-repellent) properties to materials, compositions, substrates and/or products.

Preferably, the polymer according to the invention is admixed in a composition to be provided with antimicrobial and/or antifouling properties, wherein the composition can be liquid, semi-solid or solid.

In a preferred embodiment, the polymer of the invention is dissolved in a suitable solvent to provide a liquid composition having antimicrobial and/or antifouling properties.

Examples of suitable solvents comprise DMSO, acetone, 2-butanone, isopropanol, ethanol, methanol, water, and mixtures thereof.

Preferably, the solution of the polymer of the invention is an aqueous or non-aqueous solution or formulation.

Preferably, the polymer of the invention is present in the solution in a concentration from the value of its minimum inhibitory concentration to 1000 times its minimum inhibitory concentration, preferably 2 times to 100 times its minimum inhibitory concentration, more preferably 5 times to 50 times its minimum inhibitory concentration, especially preferably 100 times its minimum inhibitory concentration.

In another preferred embodiment, the polymer of the invention is present in an emulsion or gel, a paste or cream, further preferred a W/O or O/W emulsion, or a lipid emulsion.

Preferably, the lotion, emulsion or gel, paste or cream comprises water, fat and/or oil selected from mineral oil, silicon oil, beeswax, lanolin, jojoba oil, shea butter, shea oil, palm oil, olive oil, petroleum jelly, paraffin, stearin, or any other fatty component known to the skilled expert; emulsifiers, preservatives or stabilizers like liproproteins, lecithines, stodium stearyl lactylate, cetearyl alcohol, polysorbate 20, aceteareth 20, glycerol, proteins, alcohol, and any other additives known to the skilled expert.

Preferably, the polymer of the invention is present in the lotion, emulsion or gel, paste or cream in a concentration from its minimum inhibitory concentration to 1000 times its minimum inhibitory concentration, preferably 2 to 100 times its minimum inhibitory concentration, more preferably 5 to 50 times its minimum inhibitory concentration, especially preferably 10 times its minimum inhibitory concentration.

Preferred examples of products comprising a lotion, emulsion, gel, paste or cream comprising the inventive polymer are cosmetics, medical preparations, filler media, lubrication agents, etc.

Owing to the antimicrobial property of the polymer according to the present invention, the polymer can be used to treat or prevent microbial infections in a patient. Therefore, in another aspect of the present invention, the present invention provides the use of the inventive polymer for the treatment or prevention of microbial infections in a patient, as well as medical preparations (compositions) comprising the polymer of the invention which are suitable for treatment or prevention of microbial infections. Similarly, the polymer of the present invention provides products comprising the polymer of the present invention, such as e.g. cosmetics, with an antimicrobial property, which not only protects the product against microbial contamination, but may also treat or prevent a microbial infection upon application, e.g. to the skin.

The polymer of the present invention can be administered as usual in the art, e.g. by oral administration, systemic administration, topical administration, etc. in dependence of the respective indication, e.g. the infecting microbe or pathogen, the infected area, and the like. A skilled person can readily adapt the appropriate dosage and dosage regime, and the like, in dependence of the respective indication. Preferred is a topical administration, e.g. by application of the polymer or a medical preparation thereof directly to the infected area or the area where infection should be prevented, e.g. to an (infected) area of skin or mucosa, etc.

Medical preparations comprising the polymer of the invention may further comprise any additive and/adjuvant commonly used in the art for the preparation of a respective pharmaceutical formulation, e.g. a suitable carrier, diluent, buffer, etc. Moreover, the medical preparation comprising the polymer of the present invention may also comprise other active ingredients, e.g. another antibiotic, or the like. The skilled person knows how to prepare respective formulations for the corresponding indications, e.g. as fluid or semi-solid formulation (e.g. a solution, lotion, emulsion, gel, paste or cream comprising the inventive polymer) e.g. for external application, a fluid or solid formulation, e.g. for spray application (inhalation), injection (also as depot), and the like.

The antimicrobial activity of the composition (solution, emulsion, cream, paste or gel) comprising the polymer according to the present invention can be determined by standard procedures, e.g., those described by Al-Ahmad et al., PLoS One 2013, 8(9), e73812 or by Rennie et al., Journal of Industrial Microbiology & Biotechnology 2005, 32(7), 296.

The antifouling activity of the polymer according to the present invention can be determined by standard procedures, e.g., those described by Jiang et al. or Riihe et al. as described above.

In a preferred further embodiment, the solution, emulsion, cream, lotion, paste or gel comprising the polymer of the invention can be used to impregnate or coat a material, substrate or product. Preferably, the solution, cream, lotion, paste, emulsion or gel comprising the polymer of the invention is applied to the surface of the material, substrate or product. In case of porous materials, substrates or products, the solution, cream, lotion, paste, emulsion or gel comprising the inventive polymer can soak into those pores. In case of non-porous materials, substrates or product, the solution, emulsion or gel comprising the inventive polymer can remain of the surface unaltered, or the solution, cream, lotion, paste, emulsion or gel can be modified as desired. For example, a solution, cream, lotion, paste, emulsion or gel comprising the inventive polymer can be dried by removing the solvent under appropriate conditions, resulting in the formation of a dry coating of inventive polymer on the surface of the respective material, substrate or product. Alternatively, a solution, cream, lotion, paste, emulsion or gel may be modified after application to the surface, e.g. by triggering gelling reactions, or the like, which may result in a more solid gel coating the surface of the material, substrate or product, or the like.

In another preferred embodiment, the polymer of the invention is used to coat the surface of a material, substrate or product, preferably by covalently attaching the polymer to the surface thereof, i.e. by forming at least one covalent chemical bond between the polymer of the present invention and the material, substrate or product (i.e. the surface thereof).

Preferably, the polymer of the invention is covalently attached to a surface of a material, substrate or product. Such a surface may be any suitable surface that carries appropriate functional groups or can be pre-treated so that it carries appropriate functional groups, preferably any surface that can be oxidized, thiolated or silanized, preferably an inorganic surface, such as e.g. surfaces containing or comprising metals or alloys, e.g. from iron, gold, silver, copper, aluminum, nickel, chrome, titanium, molybdenum, magnesium, zirconium, etc., or ceramics, titanium or zirconium oxides ($TiO_2$, etc.), etc, or an organic or polymeric surface, including thermosets, thermoplasts, elastomers, etc., and combinations thereof, such as oxidized poly(styrene) or oxidized poly(ethylene), (substituted) poly(ethyleneimine) (PEI), (substituted) poly(vinylpyridine) (PVP), (substituted) PVP-based polymers and co-polymers, poly(diallyldimethylammonium)-based, (substituted) poly(butylmethacrylate-co-amino-ethyl methyl-acrylate), (substituted) poly(2-(dimethyl-amino)-ethyl methacrylate)-based surfaces, co-polymers thereof, or fluorinated polymers or co-polymers thereof, or silicone polymers or co-polymers thereof, including combinations thereof, or any further polymer suitable for such an approach, or silicon surfaces, such as e.g. $SiO_2$, glass etc. Such surfaces may be furthermore a surface of a substrate, e.g. of any implant, dental implant, prosthesis, joint, bone, tooth, e.g. of an artificial joint, artificial bone, artificial tooth, inlay, etc., as well as any material used or to be used for implanting such a substrate, e.g. screws, anchors, any fastener or fixing material, etc. as well as any material used or to be used for implanting such a substrate. Such substrates may furthermore be selected from any medical or surgical device or tool, including implant trephine or trepan drill, scalpels, forceps, scissors, screws, fasteners and/or fixing material used for implantation, holders, clips, clamps, needles, linings, tubes, water tubes, pipes, water pipes, bottles and bottle inlays, inlays for medical equipment, etc., but also (surfaces of e.g.) operating tables, treatment chairs, catheter, stents, any wound dressing material, including plaster, gazes, bandages, but also bed sheets for clinical or medical purposes, sheets for covering medical devices, etc. Furthermore, surfaces or substrates may be selected from any further device, such as bindings or book covers, keyboards, computer keyboards, computer, laptops, displays, display covers, lamps, grips of tools and instruments, etc. Surfaces or substrates may also include any biomaterial suitable for tissue support, e.g. as a cell or tissue carrier system for wound dressing, or for volume preservation of solid body tissues. Surfaces or substrates may also include any substrate or surface used for storage of cells, tissue, organs, etc., but also any substrate or surface used for storage of food, such as refrigerators, coolers, storage boxes, etc.

For the purposes of the present invention, such a surface or (surface of a) substrate as defined herein may be pre-treated to allow covalent binding of the polymer of the invention. More preferably, the surface as defined above may be pretreated in two steps. The first step (defined as Step I) may allow binding of a reactive compound, e.g. a reactive silane compound or a photo-reactive silane compound or a thermo-reactive silane compound, or a photo-reactive thiol/disulfide, or a thermo-reactive thiol/disulfide, or a photo-reactive alkenyl, vinyl or acryl compound, or a thermo-reactive alkenyl, vinyl or acryl compound, to the surface or (surface of a) substrate as defined herein. After this pretreatment, the actual reactive compound as defined above is attached (defined as Step II). Preferably, Step I modifies the surface to comprise, e.g., oxide or hydroxide groups, thiol moieties, etc. It thus allows binding reactive compounds by reacting with the oxide or hydroxide groups or with thiol groups on the surface. Accordingly, the surface may be treated prior to binding of the polymer of the invention to generate e.g. hydroxide or oxide groups, e.g. with a strong base such as sodium hydroxide, ammonium hydroxide, oxygen plasma, air plasma, UV, ozone, UV-ozone, heat, open flame, and the like, or with analogous methods to generate thiol groups. In the case of a metal, the metal can be subject to an oxidizing potential to generate oxide or hydroxide sites on the surface of the metal. In the case of an organic material, the organic material may be likewise pretreated to comprise e.g. oxide or hydroxide groups, etc. Alternatively, the organic material already comprises e.g. oxide or hydroxide groups, thiol moieties, etc.

Preferably, in Step II, a reactive compound as defined above is reacted with the surface or (surface of a) substrate as defined herein. This reactive compound carries one moiety that can attach to said surface, and another moiety that can attach to the inventive polymer. It thus enables covalent binding between the oxide, thiol or other functional group on the surface, and the inventive polymer. This reactive compound is termed "surface crosslinker" in the following. It is to be distinguished from the crosslinking repeat units C of the inventive polymer defined above, or the "external" crosslinkers added to the inventive polymer to enable the network-formation of the inventive polymers that have been defined above.

Just like the external crosslinkers and the crosslinking repeat units C of the inventive polymer, the surface crosslinker may be activated thermally or photo-chemically. In the context of surface immobilization, the term "photo-crosslinking" typically means covalently attaching the polymer of the invention to a (pretreated) surface as defined herein via a photo-reactive surface crosslinker. For this purpose, the surface, which may have been pretreated with a process according to Step I, may be preferably further functionalized with a photo-reactive surface crosslinker, which is specified below.

If an additional external photo-crosslinker or a photo-crosslinkable repeat unit C is present in the inventive polymer, said polymer is immobilized on the surface as a network. If no external photo-crosslinker or photo-crosslinkable repeat unit C is present in the inventive polymer, said polymer is immobilized on the surface as a monolayer.

In the context of surface immobilization, the term "thermo-crosslinking" means covalently attaching the polymer of the invention to a (pretreated) surface as defined herein via a thermo-reactive surface-crosslinker. For this purpose, the surface which may have been pretreated with a process according to Step I may be preferably further functionalized with a thermo-reactive surface-crosslinker. If an additional external thermo-crosslinker or a thermo-crosslinkable repeat unit C is present in the inventive polymer, said polymer immobilized on the surface as a network. If no external thermo-crosslinker or thermo-crosslinkable repeat unit C is present in the inventive polymer, said polymer is immobilized on the surface as a monolayer.

The "photo-crosslinking" and "thermo-crosslinking" may also be combined. For example, the surface attachment may simultaneously or sequentially proceed via a thermo-reactive surface-crosslinker and a photo-reactive surface-crosslinker. Further, the network formation of the inventive polymer may simultaneously or sequentially proceed via a thermo-reactive external crosslinker and a photo-reactive external crosslinker, and/or via the presence of a thermo-crosslinkable repeat unit C in the inventive polymer and/or a photo-crosslinkable repeat unit C in the inventive polymer.

In this context, a suitable photo-reactive surface cross-linker may be covalently attached to such a (pretreated) surface, and may comprise, without being limited thereto, e.g. any silane, thiol or disulfide compound, preferably as mentioned herein, which has at least one photo-reactive group thereon and allows formation of a covalent bond between said photo-reactive group and the inventive polymer. For example, the photo-reactive surface-crosslinker may comprise at least one photo-reactive group as defined herein, and at least one of the group of silane compounds. Silane compounds are defined by having mono-, di-, or tri-alkoxyl silane moieties and/or mono-, di-, or tri-chlorosilane moieties, preferably silane compounds having at least one tri($C_1$-$C_3$)alkoxysilyl group and/or at least one chlorosilane group. Suitable tri($C_1$-$C_3$)alkoxysilyl groups include e.g. trimethoxysilyl, triethoxysilyl, and tripropoxysilyl, and combinations thereof. More preferably, the photo-reactive surface crosslinker may comprise, e.g., triethoxysilane-$CH_2$—$CH_2$—$CH_2$—O-benzophenone, (4-benzoylbenzoyl)amino($C_1$-$C_3$)alkyltri($C_1$-$C_3$)alkoxy silane, (4-benzoylbenzoyl)aminopropyltrimethoxy silane, (4-benzoylbenzoyl)aminoethyltrimethoxy silane, and 4-(3'-chlorodimethylsilyl)propyloxybenzophenone. Also suitable are the corresponding thiol, dithiol or disulfide compounds, for example the compound depicted in formula (XII):

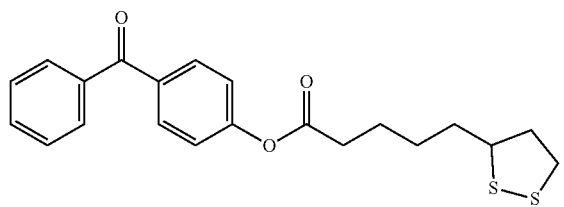

(XII)

Alternatively, the photo-reactive surface cross-linker may contain any functional group that can participate in a photo-activated reaction with any of the residues of repeat units A, B, or C of the inventive polymer, and one of the moiety defined above (silane, thiol, disulfide, etc.) that can be used to attach the photo-reactive surface cross-linker to the (pretreated) surface as defined above.

Binding of the photo-reactive surface crosslinker to the (pretreated) surface preferably occurs via its silane moiety, if a silane compound is used, alternative via any further functionality, if a non-silane compound is used, e.g. hydroxyl moieties, —C(O)OH moieties, etc., or any further functional moiety of these crosslinkers suitable to bind to the pretreated surface. Furthermore, binding of the polymer of the invention preferably occurs via the at least one photo-reactive moiety of the photo-reactive surface crosslinker.

If the polymer of the present invention consisting of different repeat units $A_i$, $B_i$ or $C_i$, carries a residue containing a double bond or triple bond on any of these repeat units, for example, if $R^1$ or $R^2$ of any of the repeat units A, comprise an alkenyl or alkynly residue as defined above, they may react with a photo-reactive surface crosslinker that contains a moiety that can be used to attach the photo-reactive surface-crosslinker to the (pretreated) surface as defined above, and an additional (protected) thiol or disulfide group. In this case, the (pretreated) surface would be first reacted with the silane, disulfide or thiol moiety of the photo-reactive surface crosslinker. Said cross-linker would then optionally be deprotected or reduced on the surface to form the desired thiol group. That thiol group would then be reacted with the alkenyl or alkynyl moiety of the inventive polymer by photoactivation, preferably UV irradiation, in a thiol-ene reaction. Thus, a surface-attached monolayer of the inventive polymer can be produced on the surface.

For example, if either $A_i$, $B_i$, or $C_i$ carry a residue containing a SH group, for example if $R^1$ or $R^2$ of any of the repeat units $A_i$ comprise an alkyl thiol, preferably a $C_1$ to $C_6$ alkyl ω-thiol, more preferably a $CH_2CH_2SH$, or $CH_2CH_2CH_2SH$, they may react with a photo-reactive surface-crosslinker (containing a moiety to attach said surface-crosslinker to the surface), and an additional alkenyl, acrylate, methacrylate, vinylbenzene, divinylbenzene, trivinylbenzene group or the like on that surface-crosslinker, in a photoactivated thiol-ene-reaction.

The functional group that is used for the reaction with the photo-reactive surface crosslinker may have to be present in a protected form until after the radical polymerization reaction, using protected groups known to a skilled expert, as specified, for example, in Greene's Protective Groups in Organic Synthesis (cf. complete citation above). After polymerization, the protective groups are then removed using a method known to the skilled expert, so that the cross-linking functionality becomes available, without otherwise altering the chemical integrity of the polymer structure.

A suitable catalyst may be added to the photo-crosslinking mixture.

In addition to the above-described surface-attached monolayer of the inventive polymer, a surface-attached polymer network of the inventive polymer can be produced, if an additional polymer-bound photo-crosslinking moiety is present in the inventive polymer or a suitable external photo-reactive cross-linker is added thereto. Preferably, the polymer bound photo-reactive crosslinking moiety is contained in repeat unit C as defined above. If the polymer consists only of repeat units A and/or B, and any of the $A_i$ or $B_i$, comprise a residue containing a double bond or triple bond on any of these repeat units, for example if $R^1$ or $R^2$ of any of the repeat units $A_i$ comprise an alkenyl or alkynly residue as defined above, they may react with an external photo-crosslinker, such as, e.g., pentaerythrityl tetrathiol, pentaerythritol tetrakis(3-mercaptopropionate), trimethylolpropane tris(3-mercaptopropionate), 2,2-bis(sulfanylmethyl)propane-1,3-dithiol, 1,2-ethandithiol, 1,3-propanedithiol, 1,3-butanedithiol 1,3-(2-methyl)-propane dithiol, 1,2, 3-trithiol propane, 1,3,8-trithiol octane, or the like, or any other photo-crosslinkable molecule with at least two thiol groups known to those skilled in the art, in a thiol-ene-reaction.

For example, if either $A_i$ or $B_i$ comprises a residue containing a SH group, for example, if $R^1$ or $R^2$ of any of the repeat units $A_i$ comprise an alkyl thiol, preferably a $C_1$ to $C_6$ alkyl co-thiol, more preferably a group —$CH_2CH_2SH$, or —$CH_2CH_2CH_2SH$, they may react with a photo-crosslinker, such as, e.g., trimethylolpropane trivinyl ether, trimethylolpropane trimethacrylate, trimethylolpropane triacrylate pentaerythritol triallyl ether, 1,3,5-triallyl-1,3,5-triazine-2,4,6-trione, 2,2-Bis[4-(2-hydroxy-3-methacryloyloxypropyloxy) phenyl]propane, triethyleneglycol dimethacrylate, triethyleneglycol diacrylate, divinylbenzene, trivinylbenzene, or any other other photo-crosslinkable molecule with at least two alkenyl, vinyl, allyl, acrylate, methacrylate groups known to those skilled in the art, in a thiol-ene-reaction.

The functional group that is used for the reaction with the external photo-crosslinker may have to be present in a protected form until after the radical polymerization reaction, using protected groups known to a skilled expert, as specified, for example, in Greene's Protective groups in organic synthesis (cf. complete citation above). After polymerization, the protective groups are then removed using a method known to the skilled expert, so that the cross-linking functionality becomes available, without otherwise altering the chemical integrity of the polymer structure.

A suitable catalyst may be added to the photo-crosslinking mixture.

External Photo-Crosslinker:

Thiol compounds suitable for network formation via photo-crosslinking may be selected from any (photo-reactive) thiol crosslinker bearing at least two thiol groups, preferably (photo-reactive) di-, tri-, tetrafunctional or multifunctional thiol crosslinker as defined herein and/or from adducts/condensation products of photo-reactive compounds and thiol compounds, e.g. an condensation product between benzophenone or any and a thiol-crosslinker as defined herein.

According to an alternative aspect of the photo-crosslinking approach, the (pretreated) surface may be functionalized with a reactive silane, thiol or disulfide compound as defined herein, which does not comprise a photo-reactive moiety. In this context, the reactive silane, thiol or disulfide compound is preferably covalently attached to the (pretreated) surface as defined herein in a first step. Then, preferably, a photo-reactive surface crosslinker is bound to the silane, thiol or disulfide e.g. via a reactive moiety of the silane, thiol or disulfide, e.g. an SH-moiety, a hydroxyl moiety, a —C(O)OH moiety, etc. In a final step, the polymer of the invention is then covalently attached to the surface via the photo-reactive moiety of the photo-reactive surface crosslinker in a photo-crosslinking reaction, e.g. via UV activation. The same applies analogously for a UV-activated thiol ene reaction between the silane and the inventive polymer.

In this context, a reactive silane compound, which does not comprise a photo-reactive moiety and which may be covalently attached to the (pretreated) surface as defined herein in a first step, is preferably selected from silane compounds having at least one or at least two tri($C_1$-$C_3$) alkoxysilyl groups. Such silane compounds may provide a more hydrolytically stable bond to the substrate at least because each tri($C_1$-$C_3$)alkoxysilyl group can result in a bond (Si—O-Metal) with the surface. Examples of suitable tri($C_1$-$C_3$)alkoxysilyl containing silane compounds include, but are not limited to bis(trimethoxysilyl)hexane, bis(trimethyoxysilyl)ethane, and bis(trimethoxysilylethyl)benzene, preferably 1,4-bis(trimethoxysilylethyl)benzene. Furthermore, a mixture of these reactive silane compounds, preferably of tri($C_1$-$C_3$)alkoxysilyl silane compounds, can be used. The silane compound may also include [gamma]-methacryloxypropyltrimethoxysilane, either alone or in combination with other silanes, e.g. [gamma]-methacryloxypropyltrimethoxysilane and 1,4-bis(trimethoxysilylethyl)benzene. The silane compound may also have hydrophobic properties, e.g. selected from 3-(3-methoxy-4-methacryloyloxyphenyl) propyltrimethoxysilane. Additionally, the reactive silane compound may be selected from e.g. dimethyl chlorosilane, methyldichlorosilane or trichlorosilane. In the latter cases (also for all chlorosilanes), the silanization reaction is preferably carried out under exclusion of moisture in dry toluene and in the presence of a base, e.g. triethylamine.

Furthermore, a photo-reactive crosslinking agent, which may be bound to the (preferably already covalently attached) reactive silane compound may be selected from any suitable photo-reactive crosslinking agent known to a skilled person to be photo-reactive. Furthermore, such a photo-reactive crosslinking agent has preferably at least one latent photo-reactive group that can become chemically reactive when exposed to an appropriate energy source, e.g. UV-radiation (UV-activation), visible light, microwaves, etc. As used herein, the phrase "photo-reactive group" refers to a chemical moiety that is sufficiently stable to remain in an inactive state (i.e., ground state) under normal storage conditions but that can undergo a transformation from the inactive state to an activated state when subjected to an appropriate energy source. Photo-reactive groups respond to specific applied external stimuli to undergo active species generation with resultant covalent bonding to an adjacent chemical structure, e.g., as provided by the same or a different molecule. Photo-reactive groups can thus be chosen to be responsive to an appropriate energy source, e.g. UV-radiation, visible light/radiation, microwaves, etc.

Such a photo-activation typically involves addition of an appropriate energy source as defined above, e.g. UV-radiation, visible light, microwaves, etc., preferably sufficient to allow covalent binding of the photo-reactive moiety to the inventive antimicrobial and/or antibiofouling polymer. Preferably, the inventive antimicrobial and/or antibiofouling polymer is bound via UV-radiation (UV-mediated crosslinking). More preferably, the integral light intensity at the sample location is typically about 50 to 150 mW cm$^{-2}$, preferably about 75 to 125 mW cm$^{-2}$, more preferably about 900 to 110 mW cm$^{-2}$, e.g. about 100 mW cm$^{-2}$. For UV-activation any suitable energy source may be applied known to a skilled person, e.g. a high-pressure mercury UV lamp, such as a high-pressure mercury UV lamp (e.g. 500 W, preferably from Oriel), or a StrataLinker 2400 (75 W, Stratagene). UV-activation may be about 2 to 300 min, activation energy from 0.1 to 100 J cm$^{-2}$.

Suitable photo-reactive groups in the context of the present invention include, for example, azides, diazos, diazirines, ketones, and quinones. Upon "activation" with an appropriate energy source, the photo-reactive group generates an active species such as free radicals including, for example, nitrenes, carbenes, and excited states of ketones.

According to one specific aspect of the photo-crosslinking approach, each photo-reactive group on the photo-reactive crosslinking agent can abstract an atom, e.g. a hydrogen atom from an alkyl group on either the silane compounds, the hydrolysis reaction product of the silane compound, the polymeric reaction product formed from the hydrolysis reaction product of the silane compound, or a combination thereof, and/or the inventive antimicrobial or antibiofouling polymer as defined above to be covalently attached. By covalently attaching to both the silane compound and the polymer of the invention, the photo-reactive crosslinking agent promotes adhesion and/or increases binding strength when attaching the polymer of the invention to a surface as described herein.

Preferably, the photo-reactive crosslinking agent is an aryl ketone, such as acetophenone, benzophenone, anthrone, and anthrone-like heterocycles (i.e., heterocyclic analogs of anthrone such as those having N, O, or S in the 10-position), or their substituted (e.g., ring substituted) derivatives. Examples of aryl ketones include heterocyclic derivatives of anthrone, including acridone, xanthone, and thioxanthone, and their ring substituted derivatives. Other suitable photo-reactive crosslinking agents include quinone such as, for example anthraquinone. The functional groups of such aryl ketones can undergo multiple activation/inactivation/reactivation cycles. For example, benzophenone is capable of photochemical excitation with the initial formation of an excited singlet state that undergoes intersystem crossing to the triplet state. The excited triplet state can insert into carbon-hydrogen bonds by abstraction of a hydrogen atom (from a polymeric coating layer, for example), thus creating a radical pair. Subsequent collapse of the radical pair leads to formation of a new carbon-carbon bond. The radical pair, or free radical, can also be used to incite chain polymerization if the appropriate monomer species are present. If a reactive bond (e.g., carbon/hydrogen) is not available for bonding, the ultraviolet light-induced excitation of the benzophenone group is reversible and the molecule returns to ground state energy level upon removal of the energy source.

Alternatively, the photo-reactive crosslinking agent may be selected from e.g. arylazides ($C_6R_5N_3$) such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide, or diazo compounds constitute another class of photo-reactive groups and include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate; etc. R may be preferably hydrogen or an alkyl as defined above. Other photo-reactive groups include the diazirines (—$CHN_2$) such as 3-trifluoromethyl-3-phenyldiazirine; and ketenes CH—C—O) such as ketene and diphenylketene.

Preferably, covalently attaching the polymer of the invention to a surface via photo-crosslinking, specifically to the photo-reactive group of the photo-reactive crosslinking agent, usually occurs via photoactivation involving one or more photo-reactive moieties of the photo-reactive crosslinking agent or the photo-reactive silane compound.

According to a further aspect, the polymer of the invention may be covalently attached to a (pretreated) surface as defined herein via a thermo-reactive compound, preferably a thermo-crosslinker, following the afore mentioned "thermocrosslinking approach". For this purpose, the (pretreated) surface is preferably further functionalized with a thermo-crosslinker. In the context of the present invention, such a thermocrosslinker may be selected from any suitable compound forming covalent bonds to a substrate and/or the polymer of the invention upon subjecting the compound to heat treatment, e.g. $C_1(Me)_2$-Si—$CH_2$—$CH_2$—$C_6H_4$—$SO_3$—$N_3$, etc.

For example, if either $A_i$, $B_i$ or $C_i$ comprise a residue containing an alkyl hydroxy group, for example if $R^1$ or $R^2$ of any of the repeat units $A_i$ comprise an alkyl hydroxy group, or if any $B_i$ is 2-hydroxyethyl methacrylate, 2-hydroxyethyl acrylate, or the like, they may react with a thermo-reactive surface cross-linker comprising an active ester, such as, e.g., succinic ester, pentafluorophenol ester, or the like, or acid chloride, anhydride, or the like.

For example, if either $A_i$ or $B_i$ comprise a residue containing an alkyl hydroxy group, for example if $R^1$ or $R^2$ of any of the repeat units $A_i$ comprise an alkyl hydroxy group, or if any $B_i$ is 2-hydroxyethyl methacrylate, 2-hydroxyethyl acrylate, or the like, they may react with acryloyl chlorid, methacryloyl chloride, vinyl chloride, allyl chlorid, vinylbenzyl chloride, 2-(ethenyloxy)-1-methanesulfonate ethane diol, 2-e(ethenyloxy)-1-toluenesulfonate ethane diol, or the like, or any other reagent known to the skilled expert to introduce a vinyl, vinylether, acryl or methacryl group by post-polymerization modification. The resulting polymer is then used as a thermo-crosslinkable polymer with or without additional external thermo-crosslinker. Examples for such an external thermo-crosslinker are compounds carrying two or more alkenyl, acrylate, methacrylate groups, vinyl, allyl, vinylether, or vinylbenzyl groups, or the like, e.g. trimethylolpropane trivinyl ether, trimethylolpropane trimethacrylate, trimethylolpropane triacrylate pentaerythritol triallyl ether, 1,3,5-triallyl-1,3,5-triazine-2,4,6-trione, 2,2-Bis[4-(2-hydroxy-3-methacryloyloxypropyloxy) phenyl]propane, triethyleneglycol dimethacrylate, triethyleneglycol diacrylate, divinylbenzene, trivinylbenzene, or any other other thermo-crosslinkers known to those skilled in the art.

The functional group that is used for the reaction with the thermo-crosslinker (defined below) may have to be present in a protected form until after the radical polymerization reaction, using protected groups known to a skilled expert, as specified, for example, in Greene's Protective groups in organic synthesis (cf. complete citation above). After polymerization, the protective groups are then removed using a method known to the skilled expert, so that the cross-linking functionality becomes available, without otherwise altering the chemical integrity of the polymer structure.

In another preferred embodiment, the above-described photo-crosslinker approach and thermo-crosslinker may be used in combination, e.g. by using a photo-crosslinker to attach the polymer of the present invention to a (pre-treated) surface and a thermo-crosslinker for preparing a polymer network of the polymer of the present invention, or vice versa, for preparing a surface coating comprising a polymer network of the polymer of the present invention, etc.

According to a first particular preferred embodiment, a surface as defined herein is preferably coated with an inventive polymer according to the following steps:

a) optionally pretreating a surface of a substrate as defined herein to comprise oxide or hydroxide groups, or other groups know to the skilled expert to react with a reactive silane;

b) functionalizing the optionally pretreated surface by covalently binding a reactive silane, thiol or disulfide compound comprising a photo-reactive crosslinker as defined herein to the pretreated surface as obtained according to step a);

c) coating the surface with the (protected) inventive polymer as prepared according to the present invention, optionally adding an external photo-crosslinker, onto the surface as obtained according to step b), d) irradiating the surface comprising the photo-reactive surface crosslinker and the optionally present external photo-crosslinker with UV light, thereby covalently binding the (protected) inventive polymer to a photo-reactive group of the photo-reactive surface crosslinker, thereby covalently binding the inventive polymer to the surface and optionally crosslinking it to a surface attached network, e) optionally carrying out a post-irradiaton treatment of the covalently bound inventive polymer as obtained by step d) by deprotection as defined herein, e.g. with an acid as defined herein, and/or carrying out washing steps.

The steps individual may be carried out as generally defined herein.

According to a second particular preferred embodiment, a surface as defined herein is preferably coated with an inventive polymer according to the following steps:

a) optionally pretreating a surface of a substrate as defined herein to comprise oxide or hydroxide groups, or other groups know to the skilled expert to react with a reactive silane;

b) functionalizing the optionally pretreated surface by covalently binding a reactive silane, thiol or disulfide compound comprising a thermo-reactive crosslinker as defined herein to the pretreated surface as obtained according to step a);

c) coating the surface with the (protected) inventive polymer as prepared according to the present invention, optionally adding an external thermo-crosslinker, onto the surface as obtained according to step b), d) heating the surface comprising the thermo-reactive surface crosslinker and the optionally present external thermo-crosslinker, thereby covalently binding the (protected) inventive polymer to a thermo-reactive group of the thermo-reactive surface crosslinker, thereby covalently binding the inventive polymer to the surface and optionally crosslinking it to a surface attached network, e) optionally carrying out a post-irradiaton treatment of the covalently bound inventive polymer as obtained by step d) by deprotection as defined herein, e.g. with an acid as defined herein, and/or carrying out washing steps.

The steps individual may be carried out as generally defined herein.

According to a third particular preferred embodiment, a surface as defined herein is preferably coated with an inventive polymer according to the following steps:

a) optionally pretreating a surface of a substrate as defined herein to comprise oxide or hydroxide groups, or other groups know to the skilled expert to react with a reactive silane;

b) functionalizing the optionally pretreated surface by covalently binding a reactive silane, thiol or disulfide compound comprising a photo-reactive crosslinker as defined herein to the pretreated surface as obtained according to step a);

c) coating the surface with the (protected) inventive polymer as prepared according to the present invention, adding an external thermo-crosslinker, onto the surface as obtained according to step b), d) irradiating the surface comprising the photo-reactive surface crosslinker with UV light, thereby covalently binding the (protected) inventive polymer to a photo-reactive group of the photo-reactive surface crosslinker, thereby covalently binding the inventive polymer to the surface, and subsequently heating the present external thermo-crosslinker, thereby further crosslinking the inventive polymer to a surface attached network, e) optionally carrying out a post-irradiaton treatment of the covalently bound inventive polymer network as obtained by step d) by deprotection as defined herein, e.g. with an acid as defined herein, and/or carrying out washing steps.

The steps individual may be carried out as generally defined herein. Alternatively, this third surface coating reaction may be carried out by using a compound comprising a thermo-crosslinker for functionalizing the pretreated surface in step b), by adding an external photo-crosslinker in step c), and by heating the surface comprising the thermo-reactive surface crosslinker, thereby covalently binding the (protected) inventive polymer to a thermo-reactive group of the thermo-reactive surface crosslinker, thereby covalently binding the inventive polymer to the surface, and subsequently irradiating the present external photo-crosslinker with UV light, thereby further crosslinking the inventive polymer to a surface attached network In case the inventive polymer comprises repeat units C comprising a photo-crosslinking and/or thermo-crosslinking moiety, it is possible to carry out the above reactions for coating a surface with a polymer network of the inventive polymer without addition of an external photo-crosslinker and/or thermo-crosslinker, respectively. For example, if the inventive polymer comprises a repeat unit C comprising a photo-crosslinking moiety, the above-described first embodiment of a surface coating reaction is carried out by irrigating the surface comprising the photo-reactive surface crosslinker and the photo-crosslinking moiety comprised in repeat unit C of the inventive polymer with UV light in step d), thereby covalently binding the (protected) inventive polymer to a photo-reactive group of the photo-reactive surface crosslinker, thereby covalently binding the inventive polymer to the surface and crosslinking it to a surface attached network at the same time. Similarly, if the inventive polymer comprises a repeat unit C comprising a thermo-crosslinking moiety, the above-described second embodiment of a surface coating reaction can be carried out by heating the surface comprising the thermo-reactive surface crosslinker and the thermo-crosslinking moiety comprised in repeat unit C of the inventive polymer in step d). Further, if the inventive polymer comprises a repeat unit C comprising a photo-crosslinking and/or thermo-crosslinking moiety, respectively, the above-described third embodiment of a surface coating reaction can be carried out without the addition of an external photo-crosslinker and/or thermo-crosslinker, respectively, by adapting step c) accordingly.

A monolayer surface coating layer may comprise a thickness of about 2 nm to about 50 nm. A surface-attached network may comprise a thickness of about 10 nm to 10 µm.

The thickness of the surface coating layer may be dependent on the different methods used for application. Preferably, the thickness of the antimicrobial and/or antifouling (protein-repellent) surface coating layer, comprising the protected or already deprotected inventive polymer, may be about 50 nm to about 500 nm.

According to another preferred embodiment of the present invention, the inventive polymer may be surface attached via "grafting onto". In this case, the inventive polymer carries a functional group that can react with the surface carrying a complementary functional group, in a thermally or photochemically activated reaction. For example, if either $A_i$, $B_i$ or $C_i$ carry a residue containing an alkyl hydroxy group, for example if $R^1$ or $R^2$ of any of the repeat units $A_i$ are an alkyl hydroxy group, or if any $B_i$ is 2-hydroxyethyl methacrylate, 2-hydroxyethyl acrylate, or the like, they may react with a surface cross-linker carrying an active ester, e.g. succinic ester, pentafluorophenol ester, or the like, or acid chloride, anhydride, or the like. Vice versa, if such an activated active ester, e.g. succinic ester, pentafluorophenol ester, or the like, or acid chloride, anhydride, or the like, is present in the inventive polymer, they may react with a complementary OH group on the surface in a "grafting onto" reaction.

According to another preferred embodiment of the present invention, a suitable surface initiator that is able to initiate the radical polymerization from a surface (e.g. the initiator reported in O. Prucker, C. A. Naumann, J. Ruehe, W. Knoll, C. W. Frank, *J. Am. Chem. Soc.* 1999, 121, 8766-8770, or any other known initiator for free or controlled radical polymerization known to the skilled expert) is immobilized on the surface as defined herein. The thus functionalized surface is then immersed into the monomer mixture needed to synthesize the inventive polymer (in an appropriate solvent or in bulk), and the polymerization reaction is initiated thermally or photo-chemically. Thus, the inventive polymer forms as surface-attached "polymer brush" in a "grafting-from" approach.

According to another preferred embodiment of the present invention, a polymer network coating of the polymer of the present invention can be applied to a pretreated surface by a) mixing the respective monomers, i.e. monomers for repeat unit A selected from monomers represented by one of formulae (X-a), (X-b), (X-c), (X-d), (X-e) and/or (X-f), and optionally comonomers for repeat units B and/or C (e.g. monomers represented by formula (XI), etc.), and a thermo-crosslinker, b) coating the surface, and then c) thermo-curing, thereby forming a polymer network on the substrate, optionally including binding to the substrate. Optionally, the active monomers may be applied in their respective protected forms and then de-protected in the polymer network coating the substrate in a subsequent step.

According to a second alternative, a coating is obtained using the polymer of the invention comprises repeat units C, which provide the inventive polymer with crosslinking functions, preferably with photo-crosslinking and/or thermally activated crosslinking functions. The inventive polymer comprising repeat units C can be advantageously applied to a surface and covalently attached thereto without the need for extensive and/or complicated preparations of the respective surface. For example, when using the inventive polymer comprising repeat units C, it is not necessary to functionalize with a crosslinking agent the surface prior to coating with the polymer.

According to one particular preferred embodiment, a surface as defined herein is preferably coated with an inventive polymer comprising repeat units C comprising a photo-crosslinking moiety according to the following steps:
a) optionally pretreating a surface of a substrate as defined herein to comprise oxide or hydroxide groups;
d) coating the optionally pretreated surface with the (protected) inventive polymer as prepared according to the present invention onto the surface as obtained according to optional step a),
e) irradiating the photo-reactive crosslinking agent with UV light thereby covalently binding the (protected) inventive polymer to a photo-reactive group of the photo-reactive crosslinking agent, thereby covalently binding the inventive polymer to the surface.
f) optionally carrying out a post-irradiaton treatment of the covalently bound inventive polymer as obtained by step e) by deprotection as defined herein, e.g. with an acid as defined herein, and/or carrying out washing steps.

The steps individual may be carried out as generally defined herein.

Preferably, applying the different compounds and/or compositions as defined above to the surface as defined herein and hence coating the surface may occur using any technique known to a skilled person to apply a liquid or semi-liquid compound to a surface, e.g. via a technique, such as immersion, spraying, spray-coating, spin coating or dip coating, pouring, Doctor blading, etc., preferably via spin-coating or dip-coating.

In this context, "spin coating" is typically a procedure used to apply uniform thin films to a planar or non-planar surface of a substrate, wherein an excess amount of a solution is usually placed on the surface, which is then rotated at high speed in order to spread the excess fluid by centrifugal force. Machines suitable for the inventive purpose preferably include spin coater or spinner. Typically, four distinct stages may be defined during the spin coating process: 1) Deposition of the coating fluid onto the surface of a substrate, e.g. by using a nozzle, pouring the coating solution or by spraying it onto the surface. A substantial excess of coating solution is usually applied compared to the amount that is required. 2) Acceleration of the substrate up to a final, desired, rotation speed. 3) Spinning of the substrate at a constant rate, wherein fluid viscous forces dominate the fluid thinning behavior. 4) Optionally spinning of the substrate at a constant rate, wherein solvent evaporation dominates the coating thinning behavior. In the continuous process, the steps are carried out directly after each other.

Furthermore, "dip-coating" is typically a procedure used to apply uniform thin films onto flat or cylindrical/round-shaped or otherwise shaped surfaces of substrates and typically can be separated into five stages: 1) Immersion: The substrate is preferably immersed in the solution of the coating material, either without or at a constant speed. 2) Start-up: The substrate preferably remains inside the solution for a while and is started to been pulled up. 3) Deposition: The thin layer is preferably deposited on the substrate while it is pulled up. The withdrawing is optionally carried out by rotating at a preferably constant speed. The speed determines the thickness of the coating. 4) Drainage: Excess liquid usually drains from the surface. 5) Optionally evaporation: The solvent may evaporate from the liquid, forming the thin layer. In the continuous process, the steps are carried out directly after each other.

Preferably, the surface as defined above, preferably a pretreated and functionalized surface may be coated as defined above, e.g. with the polymer of the invention via spin coating or dip-coating.

Preferably, the polymer of the invention comprising repeat units C may be used to prepare a multi-layer of polymer on the surface of the substrate. The crosslinking moiety present in repeat unit C of the inventive polymer is capable of crosslinking the inventive polymer to a polymer coating already present on the surface of the substrate. The polymer coating already present is a coating of the inventive polymer or another polymer, preferably a coating of the inventive polymer. By this method of coating, a multi-layered crosslinked polymer network coating can be advantageously prepared. The multi-layered crosslinked polymer network coating is associated with the advantageous properties of higher layer thickness and more homogeneous surface coverage.

In a preferred method of coating a multi-layered crosslinked polymer network to a substrate, the steps d) and e) of the above method are repeated at least twice, preferably two times to twenty times, more preferably two to five times, and especially preferred about two times.

A coating comprising a multi-layered crosslinked polymer network can also be prepared by adding a suitable crosslinking agent as described in the following.

Preferably, a (thiol-ene) crosslinked network of the polymers of the invention is preferably formed via a thiol-crosslinker to form covalent bonds between the inventive polymers via their double bonds, as described above ("thiol-ene crosslinking approach"). Such formation of the network structure can also be carried out prior to attaching the polymer network of the inventive polymers to a surface or simultaneously or even subsequently.

For any of these variants, the polymers of the invention are preferably mixed with a multifunctional crosslinker, preferably a di-, tri-, tetrafunctional or multifunctional crosslinker, preferably a multifunctional thiol crosslinker, more preferably a di-, tri- or even tetrafunctional thiol crosslinker, which allows crosslinking of the inventive polymers to form a crosslinked network. In this context, the term "multifunctional" preferably refers to the number of thiol-moieties or SH-moieties of such a crosslinker compound, e.g. 2, 3, 4, 5, 6, 7, 8, 9, 100 or even more thiol-moieties or SH-moieties may be contained in such a multifunctional thiol crosslinker.

Crosslinking the inventive polymers with each other preferably occurs via activation of the double bonds present in the repeat units of the polymers, e.g. thermally or via photo-activation as described above, and thereby crosslinking the polymers with each other. Generally, for this purpose, a solution of polymers of the invention in their protected form and a multifunctional crosslinker as defined herein, e.g. a tetrafunctional thiol cross-linker (SH), may be mixed and then spin-coated, dip-coated or spray-coated onto the surface of a substrate, or the mixture may be kept in solution. Upon activation, e.g. irradiation with UV light, the polymer precursors are crosslinked to neighboring polymer chains of other polymers through the multifunctional thiol moieties. A deprotection step then yields the antimicrobial and/or antibiofouling (protein-repellent) functionality.

Alternatively, the thiol-ene crosslinking of inventive polymers with each other may occur simultaneously to attaching the inventive polymers to the surface of a substrate. Generally, for this purpose, a solution of polymers of the invention in their protected form and a multifunctional crosslinker as defined herein, e.g. a tetrafunctional thiol cross-linker (SH), may be is spin-coated onto the surface of a substrate that has been preferably pretreated as mentioned above and modified with a photo-reactive crosslinking agent, e.g. a benzophenone crosslinker (BP). Upon activation, e.g. irradiation with UV light, the polymers are simultaneously attached to the surface through the benzophenone cross-linker and to neighboring polymer chains of other polymers of the invention to form a coating comprising a multi-layered crosslinked polymer network.

Preferably, a multifunctional crosslinker for the "thiol-ene crosslinking approach" is selected from a di-, tri-, tetrafunctional or multifunctional crosslinker, preferably a multifunctional thiol crosslinker, more preferably preferably a di-, tri- or even tetrafunctional thiol crosslinker, e.g. 1,2-ethandithiol, 1,3-propane trithiol, analogous higher bifunctional homologoues thereof, analogous tri- and tetrafunctional aliphatic homologoues thereof including ethane-1,1,2,2-tetrathiol, ethene-1,1,2,2-tetrathiol, and pentaerythryltetrathiol (=2,2-bis(mercaptomethyl)propane-1,3-dithiol,

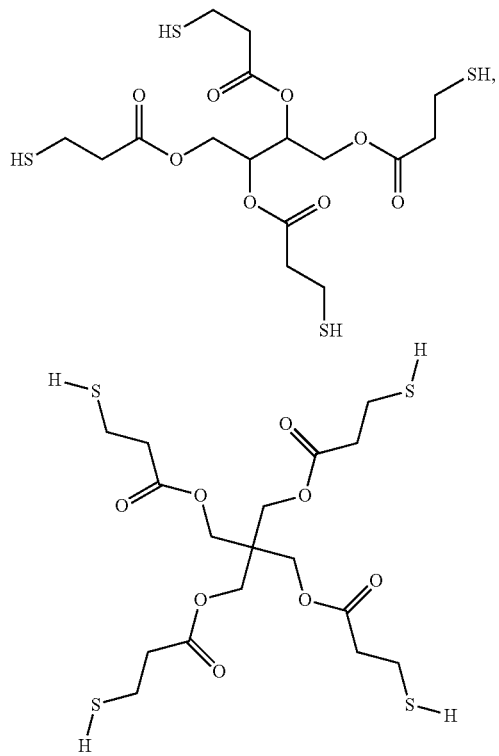

2,2'-(ethylenedioxy)diethanethiol and higher bifunctional homologoues thereof such as tetra(ethylene glycol) dithiol and hexa(ethylene glycol) dithiol, ananolgous trifunctional ethylenen glycol and polyethylen glycol thiols, and analogous ethylenen glycol and polyethylen glycol tetrafunctional thiols, 1,4-benzenedimethanethiol and analogous bi-, tri, or tetrafunctional aromatic thiols including 2,2-bis(sulfanylmethyl)propane-1,3-dithiol), benzene-1,2,4,5-tetrathiol, SH-functionalized nanoparticles, etc.

Using an additional crosslinking agent, such as, e.g., a multifunctional thiol-crosslinker, allows to prepare a coating comprising a multi-layered crosslinked polymer network from a polymer of the invention comprising no repeat unit C (i.e. a homopolymer of repeat units A or a co-polymer of repeat units A and B).

As defined above, the polymer of the invention can be covalently attached to a surface to obtain an antimicrobially active and/or antifouling (protein-repellent) surface. Preferably, such a surface coating layer has a thickness of about 10 nm to about 1000 µm, preferably a thickness from about 10 nm to about 100 µm, to about 200 µm, to about 300 µm, to about 400 µm, to about 500 µm, to about 600 µm, to about 700 µm, to about 800 µm, to about 900 µm, to about 1000 µm, to about 2000 µm, to about 3000 µm, likewise from about 100 nm, 500 nm or 1000 nm to any of the above defined upper values, etc.

The antimicrobial activity of the coating comprising the polymer according to the present invention can be determined by standard procedures, e.g., by JIS Z 2801:2000, or those described by Haldar et al. Nature Protocols 2007, 2(19), 2412 or by Al-Ahmad et al., PLoS One 2014, e111357.

Preferably, the coating exhibits protein-repellency or antifouling properties. The antifouling activity of the coating comprising the polymer according to the present invention can be determined, for example, by surface plasmon resonance spectroscopy, as described above.

In another aspect, the present invention provides a material, substrate or product, the surface of which is coated with a polymer according to the present invention.

Preferably, the substrate comprises a polymer coating having a thickness of from 10 nm to 1000 μm, further preferred of from 100 nm to 100 μm, and especially preferred of from 200 nm to 10 μm.

Preferably, the antimicrobial property of the substrate comprising the coating according to the present invention can be determined by standard procedures, e.g., by JIS Z 2801:2000, or those described by Haldar et al. Nature Protocols 2007, 2(19), 2412 or by Al-Ahmad et al., PLoS One 2014, e111357.

Preferably, the protein-repellency or antifouling properties of the substrate comprising the coating according to the present invention can be determined, for example, by surface plasmon resonance spectroscopy.

EXAMPLES

General Methods.

All oxygen-sensitive reactions were carried out in inert gas atmosphere (e.g. nitrogen). Glassware used for such reactions was heated in vacuo. Solid components were added to reaction flasks under nitrogen flow. Liquid components were de-gassed prior to use with freeze-pump-thaw cycles and added using nitrogen-purged syringes. The polymerization mixtures were subject to three freeze-pump-thaw cycles prior to heating.

All chemicals were ACS reagent or p.a. quality, and used as received. All solvents were 99% quality and used as received unless otherwise indicated. Dimethyl acrylamide was filtered over aluminum oxide before use. Dichloromethane, the most commonly used reaction solvent, was freshly distilled from phosphorous pentoxide under nitrogen atmosphere. Aqueous solutions used for workup, for example NaCl and NaHCO$_3$, were saturated solutions in equilibrium with solid precipitate.

Gel permeation chromatography (GPC) elugrams were recorded on a SDV column from PSS (Polymer Standard Services, Mainz, Germany) in Chloroform at 20 to 30° C. and a flow rate of 1 mL min$^{-1}$. $M_n$ of the polymer was determined by calibration with poly(methyl methacrylate) standards form PSS.

All NMR spectra were recorded on a 250 MHz Avance Spectrometer (Bruker, Madison, Wis.) in deuterated solvents (typically CDCl$_3$, DMSO-d$_6$, Aceton-d$_6$ and D$_2$O). Coupling constants are stated in Hertz, the chemical shifts δ are given in ppm. Mass spectra were recorded on a LCQ Advantage or Exactive mass spectrometer by Thermo Fisher (Waltham, Mass., USA) using electrospray ionization (ESI) or atmospheric pressure chemical ionization (APCI). The FTIR spectra were recorded from 4000 to 400 cm$^{-1}$ with a Bio-Rad Excalibur spectrometer (Bio-Rad, Miinchen, Germany), using a spectrum of the blank double side polished silicon wafer as background. Sample solution (dissolved in dichloromethane or another suitable solvent) were drop coated onto double side polished silicon wafers and measured after the solvent was evaporated. In the analytical data, the symbol ** designates that the peak assignments is interchangeable.

Determination of the Minimum Inhibitory Concentration (MIC$_{90}$).

The bacterial strain used (*Escherichia coli* ATCC 25922) had been long-term stored at −80° C. in basic growth medium containing 15% (v/v) glycerol. An overnight culture of the bacterial strain was prepared (10$^6$ colony forming units (CFU) mL$^{-1}$ in Mueller-Hinton Broth (MHB)). Using a multi-channel pipette, a 96-well microtiter plate was inoculated with the appropriate volumes of bacterial cultures previously prepared in MHB. Stock solutions of the polymers to be tested were prepared in dimethyl sulfoxide. All polymers were tested in MHB containing residuals of DMSO in a concentration series ranging from 400 μg mL$^{-1}$ to 6.25 μg mL$^{-1}$. The total volume in each well was 150 μL. In parallel, a dilution series of DMSO was also tested to exclude possible effects of DMSO residuals. Inoculated wells with MHB which contained neither polymers nor DMSO served as positive control for bacterial growth. Sterile MHB was taken as blank to exclude any contamination. The plates were incubated for 18 h at 37° C. in an aerobic atmosphere with 5% CO$_2$. After incubation, the optical density (OD) at 600 nm was determined using a Tecan Infinite 200 plate-reader (Tecan, Crailsheim, Germany). All tests for each strain were carried out at least in duplicate. The MIC was defined as the lowest concentration of each polymer that was able to inhibit bacterial growth, and is reported with the percentage of bacterial growth at that concentration. The MIC$_{900}$ was defined as the concentration at which at least 90% growth reduction was observed.

*S. aureus* was handled analogously, as described in A. Al-Ahmad, D. Laird, P. Zou, P. Tomakidi, T. Steinberg, K. Lienkamp, PLoS One 2013, 8, e73812.

Monomer Synthesis.

Example 1

Synthesis of itaconic acid 4-alkyl ester (methyl to butyl). 4.25 g (37.9 mmol) itaconic anhydride was dissolved in 10 mL dichloromethane (DCM) was added to an excess of the respective alcohol (methanol, ethanol, propanol or butanol, 40 mL). 12 drops of concentrated H$_2$SO$_4$ were added. The reaction mixture was stirred for 48 h at room temperature. Then, 50 mL DCM was added. This solution was extracted three times with 50 mL K$_2$CO$_3$ solution (10%) and the aqueous phase was washed three times with DCM. The organic layers were dried over Na$_2$SO$_4$ and the solvent was evaporated at the rotary evaporator. This phase contained the side product, itaconic acid dialkyl ester, which was dried in dynamic vacuum. Concentrated HCl was added to the aqueous phase until the pH was 2. The aqueous phase was then extracted three times with 100 mL DCM and dried over Na$_2$SO$_4$. The solvent was evaporated at the rotary evaporator and the product was dried in dynamic vacuum overnight. Itaconic acid-4-alkyl ester was received as a colorless solid. The structure of the obtained monomers and the proton numbering for $^1$H-NMR assignment are shown below.

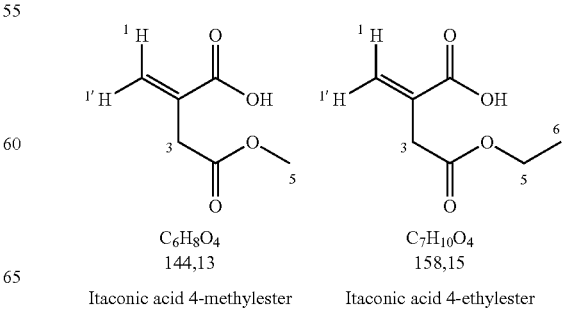

-continued

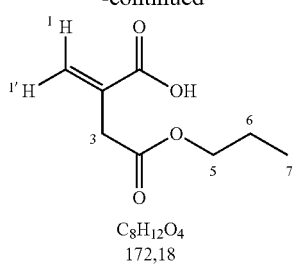

$C_8H_{12}O_4$
172,18

Itaconic acid 4-propylester

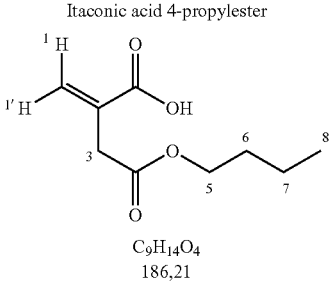

$C_9H_{14}O_4$
186,21

Itaconic acid 4-butylester

Analytical Data:
Itaconic Acid 4-Methylester:
  Yield: 1.65 g; 11.4 mmol; 30%
  MS (APCI, 5 µA): m/z={[M−H]$^+$}=143.03
  $^1$H-NMR (250 MHz, CDCl$_3$): δ=6.50 (s, 1-H), 5.88 (s, 1'-H), 3.74 (s, 5-CH$_3$), 3.39 (s, 3-CH$_2$).
  $^{13}$C-NMR (63 MHz, CDCl$_3$): δ=171.97 (s, 3'-CO), 171.51 (s, 4-CO), 133.60 (s, 2-C), 131.33 (s, 1-C), 52.56 (s, 5-C), 37.43 (s, 3-C).
Itaconic Acid 4-Ethylester:
  Yield: 4.57 g; 28.9 mmol; 75%
  MS (APCI, 5 µA): m/z={[M−H]$^+$}=157.05
  $^1$H-NMR (250 MHz, CDCl$_3$): δ=6.49 (s, 1-H), 5.86 (s, 1'-H), 4.20 (td, J=7.10 Hz, 5-CH$_2$), 3.37 (s, 3-CH$_2$), 1.29 (t, J=7.11 Hz, 6-CH$_3$).
  $^{13}$C-NMR (63 MHz, CDCl$_3$): δ=172.03 (s, 3'-CO), 171.07 (s, 4-CO), 133.76 (s, 2-C), 131.10 (s, 1-C), 61.44 (s, 5-C), 37.70 (s, 3-C), 14.43 (s, 6-C).
Itaconic Acid 4-Propylester:
  Yield: 5.09 g; 29.6 mmol; 80%
  MS (APCI, 5 µA): m/z={[M−H]$^+$}=171,06
  $^1$H-NMR (250 MHz, CDCl$_3$): δ=6.49 (s, 1-H), 5.87 (s, 1'-H), 4.10 (t, J=6.71 Hz, 5-CH$_2$), 3.38 (s, 3-CH$_2$), 1.68 (tq, J=7.10 Hz, 6-CH$_2$), 0.96 (t, J=7.42 Hz, 7-CH$_3$).
  $^{13}$C-NMR (63 MHz, CDCl$_3$): δ=171.98 (s, 3'-CO), 171.14 (s, 4-CO), 133.81 (s, 2-C), 130.99 (s, 1-C), 67.04 (s, 5-C), 37.71 (s, 3-C), 22.24 (s, 6-C), 10.63 (s, 7-C).
Itaconic Acid 4-Butylester:
  Yield: 5.16 g; 27.7 mmol; 75%
  MS (APCI, 5 µA): m/z={[M−H]$^+$}=185.08
  $^1$H-NMR (250 MHz, CDCl$_3$): δ=6.48 (s, 1-H), 5.86 (s, 1'-H), 4.14 (t, J=6.56 Hz, 5-CH$_2$), 3.37 (s, 3-CH$_2$), 1.54-1.76 (m, 8-CH$_2$), 1.40 (tq, J=7.30 Hz, 7-CH$_2$), 0.95 (t, J=7.27 Hz, 8-CH$_3$).
  $^{13}$C-NMR (63 MHz, CDCl$_3$): δ=172.05 (s, 3'-CO), 171.10 (s, 4-CO), 133.81 (s, 2-C), 130.98 (s, 1-C), 65.30 (s, 5-C), 37.71 (s, 3-C), 30.90 (s, 6-C), 19.40 (s, 7-C), 13.97 (s, 8-C).

Example 2

Synthesis of Itaconic Acid 1-(N-Boc-Aminoethyl) 4-Alkyl Diester (Methyl to Butyl).

6.6 mmol Itaconic acid 4-alkyl ester (prepared as described in Example 1) was dissolved in 10 mL DCM. 1.3 g (7.9 mmol, 1.2 equivalents) N-Boc-2-aminoethanol and 1.2 g (9.9 mmol, 1.5 equivalents) N,N-dimethyl aminopyridine (DMAP) were added. The reaction mixture was stirred for 10 min. An ice bath was added and the reaction mixture was stirred for another 10 min. After that, 1.5 g (7.3 mmol, 1.1 equivalents) dicyclohexyl carbodiimide (DCC) in 10 mL DCM were added dropwise. The reaction mixture was stirred overnight. The precipitate was removed by filtration, and the solution was washed with KHSO$_4$ (10 w %, 3×100 mL) and NaHCO$_3$ (conc., 2×100 mL). It was then dried over Na$_2$SO$_4$. The solvent was evaporated at the rotary evaporator. The product was then dissolved in a minimum amount of DCM, and frozen (−20° C.) overnight to remove the side product, which precipitated. The cold organic phase was filtrated quickly using pre-cooled equipment, and the solvent was removed at the rotary evaporator. The pure 1-(N-Boc-aminoethyl) 4-alkyl diester was obtained as colorless solid (for Ethyl to Butyl), or pale yellow oil (Methyl). The structure of the obtained monomers and the proton numbering for $^1$H-NMR assignment are shown below.

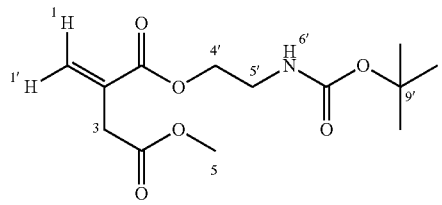

$C_{13}H_{21}NO_6$
287, 31

1-(N-Boc-aminoethyl) 4-methyl diester

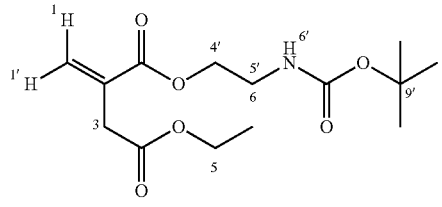

$C_{14}H_{23}NO_6$
301, 34

1-(N-Boc-aminoethyl) 4-ethyl diester

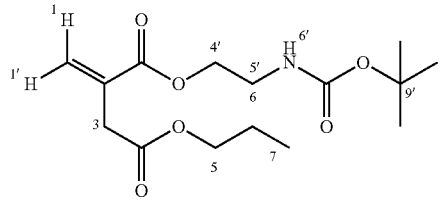

$C_{15}H_{25}NO_6$
315, 37

1-(N-Boc-aminoethyl) 4-propyl diester

-continued

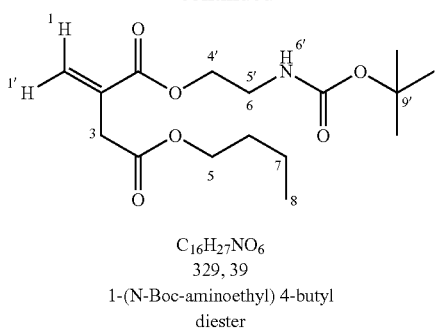

C$_{16}$H$_{27}$NO$_6$
329, 39
1-(N-Boc-aminoethyl) 4-butyl diester

Analytical Data:
1-(N-Boc-Aminoethyl) 4-Methyl Diester:
Yield: 1.2 g; 4.0 mmol; 61%
MS (ESI, 4-5 kV): m/z={[M+Na]$^+$}=310.12
$^1$H-NMR (250 MHz, CDCl$_3$): δ=6.35 (s, 1-H), 5.72 (s, 1'-H), 4.94 (br. s, 6'-H), 4.22 (t, J=5.21 Hz, 4'-CH$_2$), 3.71 (s, 5-CH$_3$), 3.41 (tq, J=5.20 Hz, 5'-CH$_2$), 3.35 (s, 3-CH$_2$), 1.44 (s, 9'-(CH$_3$)$_3$).
$^{13}$C-NMR (63 MHz, CDCl$_3$): δ=171.68 (s, 3'-CO), 166.23 (s, 4-CO), 156.15 (s, 7'-CO), 133.92 (s, 2-CH$_2$), 129.47 (s, 1-C), 79.83 (s, 9'-C—(CH$_3$)$_3$), 64.74 (s, 4'-CH$_2$), 52.45 (s, 5-CH$_3$), 39.92 (s, 5'-CH$_2$), 37.96 (s, 3-CH$_2$), 28.72 (s, 9'-C—(CH$_3$)$_3$).

1-(N-Boc-Aminoethyl) 4-Ethyl Diester:
Yield: 1.9 g; 6.3 mmol; 94%
MS (ESI, 4-5 kV): m/z={[M+Na]$^+$}=324.14
$^1$H-NMR (250 MHz, CDCl$_3$): δ=6.39 (s, 1-H), 5.75 (s, 1'-H), 4.92 (br. s., 6'-H), 4.26 (t, J=5.30 Hz, 4'-CH$_2$), 4.20 (q, J=7.20 Hz, 5-CH$_2$), 3.46 (td, J=5.30 Hz, 5'-CH$_2$), 3.37 (s, 3-CH$_2$), 1.47 (s, 9'-(CH$_3$)$_3$), 1.30 (t, J=7.19 Hz, 6-CH$_3$).
$^{13}$C-NMR (63 MHz, CDCl$_3$): δ=171.25 (s, 3'-CO), 166.30 (s, 4-CO), 156.16 (s, 7'-CO), 134.6 (s, 2-C), 129.31 (s, 1-CH$_2$), 79.81 (s, 9'-C—(CH$_3$)$_3$), 64.76 (s, 4'-CH$_2$), 61.37 (s, 5-CH$_2$), 39.94 (s, 5'-CH$_2$), 38.23 (s, 3-CH$_2$), 28.73 (s, 9'-C—(CH$_3$)$_3$), 14.51 (s, 6-CH$_3$).

1-(N-Boc-Aminoethyl) 4-Propyl Diester:
Yield: 1.9 g; 6.3 mmol; 91%
MS (APCI, 5 μA): m/z={[M+H]$^+$}=316.17
$^1$H-NMR (250 MHz, CDCl$_3$): δ=6.38 (s, 1-H), 5.75 (s, 1'-H), 4.92 (br. s, 6'-H), 4.25 (t, J=5.20 Hz, 4'-CH$_2$), 4.10 (t, J=6.70 Hz, 5-CH$_2$), 3.46 (td, J=5.20 Hz, 5'-CH$_2$), 3.39 (s, 3-CH$_2$), 1.69 (tq, J=7.10 Hz, 6-CH$_2$), 1.47 (s, 9'-(CH$_3$)$_3$), 0.96 (t, J=7.35 Hz, 7-CH$_3$).
$^{13}$C-NMR (63 MHz, CDCl$_3$): δ=171.35 (s, 3'-CO), 166.33 (s, 4-CO), 156.18 (s, 7'-CO), 134.8 (s, 2-C), 129.32 (s, 1-CH$_2$), 79.84 (s, 9'-C—(CH$_3$)), 66.99 (s, 5-CH$_2$), 64.81 (s, 4'-CH$_2$), 39.93 (s, 5'-CH$_2$), 38.24 (s, 3-CH$_2$), 28.73 (s, 9'-C—(CH$_3$)$_3$), 22.27 (s, 6-CH$_2$), 10.69 (s, 7-CH$_3$).

1-(N-Boc-Aminoethyl) 4-Butyl Diester:
Yield: 1. g, 4.6 mmol; 70%
MS (ESI, 4-5 kV): m/z={[M+Na]$^+$}=352.17
$^1$H-NMR (250 MHz, CDCl$_3$): δ=6.26 (s, 1-H), 5.64 (s, 1'-H), 5.05 (br. s., 6'-H), 4.13 (t, J=5.29 Hz, 4'-CH$_2$), 4.03 (t, J=6.63 Hz, 5-CH$_2$), 3.33 (td, J=5.20 Hz, 5'-CH$_2$), 3.27 (s, 3-CH$_2$), 1.45-1.62 (m, 6-CH$_2$), 1.36 (s, 9'-(CH$_3$)$_3$), 1.19-1.34 (m, 7-CH$_2$), 0.84 (t, J=7.20 Hz, 8-CH$_3$).
$^{13}$C-NMR (63 MHz, CDCl$_3$): δ=171.20 (s, 3'-CO), 166.24 (s, 4-CO), 156.15 (s, 7'-CO), 134.8 (s, 2-C), 129.09 (s, 1-CH$_2$), 79.62 (s, 9'-C—(CH$_3$)), 65.13 (s, 5-CH$_2$), 64.65 (s, 4'-CH$_2$), 39.84 (s, 5'-CH$_2$), 38.10 (s, 3-CH$_2$), 30.87 (s, 6-CH$_2$), 28.65 (s, 9'-C—(CH$_3$)$_3$), 19.34 (s, 7-CH$_2$), 13.93 (s, 8-CH$_3$).

Example 3

Synthesis of Itaconic Acid 4-Propylamide.

Itaconic anhydride (5.1 g, 45.5 mmol) was dissolved in DCM (20 mL). H$_2$SO$_4$ (conc., 5 drops) was added. After ice cooling for 15 min propylamine (4.0 mL, 49.1 mmol, 1.1 eq.) in DCM (10 mL) was added dropwise over 30 min. The ice bath was removed and the solution stirred for 24 h. Then, the precipitate (pure product) was removed by filtration. The solution was extracted three times with 50 mL K$_2$CO$_3$ solution (10%) and the aqueous phase was washed three times with DCM. Concentrated HCl was added to the aqueous phase until the pH was 2. The aqueous phase was now extracted three times with 100 mL DCM and dried over Na$_2$SO$_4$. The solvent was evaporated at the rotary evaporator and the product was dried in dynamic vacuum overnight. Itaconic acid-4-propylamide was received as a colorless solid. The structure of the obtained monomer and the proton numbering for $^1$H-NMR assignment are shown below.

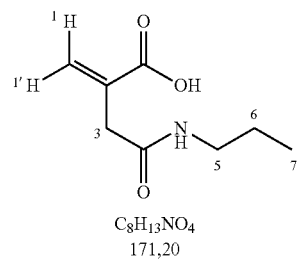

C$_8$H$_{13}$NO$_4$
171,20

Yield: 3.9 g, 23.0 mmol, 51%
MS (ESI, 4-5 kV): m/z={[M+Na]$^+$}=194.08
$^1$H NMR (250 MHz, Acetone-d6): δ=11.46 (br. s, OH), 7.24 (br. s., NH), 6.22 (s, 1-H), 5.73 (s, 1'-H), 3.24 (s, 3-CH$_2$), 3.17 (td, J=6.50 Hz, 5-CH$_2$), 1.51 (tq, J=7.30 Hz, 6-CH$_2$), 0.90 (t, J=70.42 Hz, 7-CH$_3$).
$^{13}$C NMR (63 MHz, Acetone-d6): δ=170.22 (s, 4-CO), 167.57 (s, 2'-CO), 136.42 (s, 2-C), 127.38 (s, 1-C), 41.18 (s, 5-C), 39.40 (s, 3-C), 22.92 (s, 6-C), 11.13 (s, 7-C).

Example 4

Synthesis of Itaconic Acid 1-(N-Boc-Aminoethyl)-4-Propyldiamide.

5.8 mmol Itaconic acid 4-propylamide (prepared as described in Example 3) was dissolved in 10 mL DCM or acetonitrile. 1.12 g (7.0 mmol, 1.2 equivalents) N-Boc-ethylenediamine and 1.06 g (8.6 mmol, 1.5 equivalents) N,N-dimethyl aminopyridine (DMAP) were added. The reaction mixture was stirred for 10 min. An ice bath was added and the reaction mixture was stirred for another 10 min. After that, 1.32 g (6.4 mmol, 1.1 equivalents) dicyclohexyl carbodiimide (DCC) in 10 mL DCM were added dropwise. The reaction mixture was stirred overnight. The precipitate was removed by filtration, and the solution was washed with KHSO$_4$ (10 w %, 3×50 mL) and NaHCO$_3$ (saturated, 2×50 mL). It was then dried over Na$_2$SO$_4$. The solvent was evaporated at the rotary evaporator. The product was recrystallized from diethylether. The structure of the obtained monomer and the proton numbering for $^1$H-NMR assignment are shown below. The procedure was also successfully realized with 0.1 eq. of DMAP to yield 27% raw product which needs to be further purified.

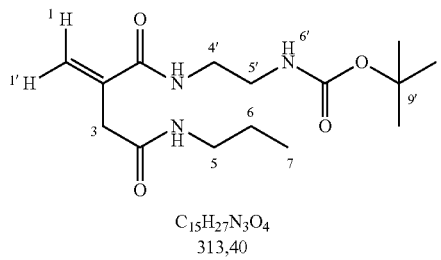 [SMILES: C=C(CC(=O)NCCC)C(=O)NCCNC(=O)OC(C)(C)C]

$C_{15}H_{27}N_3O_4$
313,40

Yield: 0.49 g, 1.6 mmol, 27%
MS (ESI, 4-5 kV): m/z={[M+Na]$^+$}=336.19
$^1$H NMR (250 MHz, Acetone-d$_6$) δ=7.89 (br. s., NH), 7.35 (br. s., NH), 6.14 (br. s., NH), 5.84 (s, 1-H), 5.46 (s, 1'-H), 3.36 (td, J=6.10 Hz, 4'-CH$_2$), 3.26 (t, J=6.10 Hz, 5-CH$_2$), 3.20 (s, 3-CH$_2$), 3.14 (td, J=7.00 Hz, 5'-CH$_2$), 1.50 (tq, J=70.20 Hz, 6-CH$_2$), 1.42 (s, 9'-(CH$_3$)$_3$), 0.90 (t, J=70.42 Hz, 7-CH$_3$).
$^{13}$C-NMR (63 MHz, Acetone-d$_6$): δ=170.18 (s, 3'-CO), 168.39 (s, 4-CO), 156.61 (s, 7'-CO), 134.08 (s, 2-C), 129.32 (s, 1-CH$_2$), 78.25 (s, 9'-C—(CH$_3$)$_3$), 51.93 (s, 5'-CH$_2$), 48.62 (s, 4'-CH$_2$), 40.40 (s, 5-CH$_2$), 34.06 (s, 3-CH$_2$), 28.13 (s, 9'-C—(CH$_3$)$_3$), 22.98 (s, 6-CH$_2$), 11.15 (s, 7-CH$_3$).
Polymer Synthesis.

Example 5

Homopolymers: Synthesis of Itaconic Acid 1-(N-Boc-Aminoethyl) 4-Propyl Ester 0.400 g of itaconic acid 1-(N-Boc-aminoethyl)-4-propyl ester (1.27 mmol, 1.0 equivalents) was added to a heat-dried Schlenk tube under nitrogen. Solvent (N,N-dimethylformamid, DMF) was added so that the monomer concentration was 2.0 mol L$^{-1}$ (0.6 g mL$^{-1}$). The initiator azoisobutyric acid nitrile (AIBN, 0.2 mg, 0.001 equivalents) was then added to the reaction mixture, and the reaction mixture was subject to three freeze-pump-thaw cycles. An oil bath was set to the reaction temperature of 60° C., and the reaction was allowed to proceed for 6 d. The reaction was quenched by stirring the open flask under ambient atmosphere. DMF was then removed by applying high vacuum over 12 h. It was then taken up in little DCM and added dropwise into cold hexane (100-150 mL) while stirring vigorously. The polymer precipitated. It was removed by filtration, washed with cold hexane. The precipitation procedure was repeated once more before the polymer was dried under vacuum. The structure of the obtained polymers obtained and the proton numbering for $^1$H-NMR assignment are shown below.

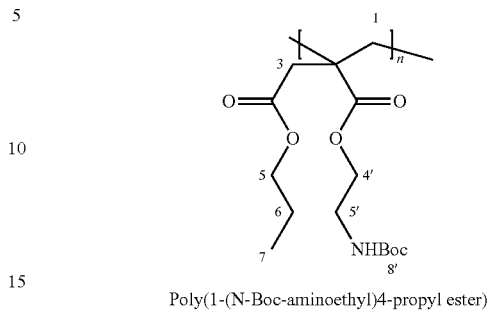

Poly(1-(N-Boc-aminoethyl)4-propyl ester)

Structure of Itaconic Acid Propyl Ester Homopolymers and Proton Numbering for $^1$H-NMR Assignment.
Yield: 90 mg, 22%
GPC (CHCl$_3$): M$_n$=8600 g mol$^{-1}$, D=1.6
$^1$H-NMR of Poly(1-(N-Boc-aminoethyl) 4-propyl ester) (250 MHz, CDCl$_3$): δ=5.65 (br. s, NH), 4.02 (br. s, 4'-CH$_2$, 5-CH$_2$), 3.38 (br. s, 5'-CH$_2$), 2.73 (br. s, 1-CH$_2$, 3-CH$_2$), 1.70 (m, 6-CH$_2$), 1.46 (s, 8'-(CH$_3$)$_3$), 0.97 (br. s, 7-CH$_3$).

Example 6

Copolymers: Synthesis of Poly[(Itaconic Acid 1-(N-Boc-Aminoethyl) 4-Alkyl Diester)-Co—(N,N-Dimethyl Acrylamide)]

Series 1:

Itaconic acid 1-(N-Boc-aminoethyl) 4-methyl ester (equivalents as specified in Table 1 was added to a heat-dried Schlenk tube under nitrogen. Freshly purified dimethyl acrylamide (DMMA, equivalents as specified in Table 1) was added using a syringe. Solvent (dimethyl sulfoxide, DMSO; or N,N-dimethylformamid, DMF) was added so that the monomer concentration was 0.5 g L$^{-1}$. The initiator azoisobutyric acid nitrile (AIBN, equivalents as specified in Table 1) was then added to the reaction mixture, and the reaction mixture was subject to three freeze-pump-thaw cycles. An oil bath was set to the reaction temperature of 70° C., and the reaction was allowed to proceed for the time specified in Table 1.

The mixture was then cooled and the reaction was quenched by stirring the open flask under ambient atmosphere. It was then added dropwise into cold hexane (100-150 mL) while stirring vigorously. The polymer precipitated. It was removed by filtration, washed with cold hexane and dried in dynamic vacuum. The yields are given in Table 2. The structure of the obtained polymers obtained and the proton numbering for $^1$H-NMR assignment are shown below.

TABLE 1

Reaction Parameters for the copolymerization of itaconic Acid 1-(N-Boc-aminoethyl) 4-alkyl ester with DMAA (Series 1). The target molecular mass was 3,000 g mol$^{-1}$. Methyl, Ethyl, Propyl and Butyl refer to the respective 1-(N-boc-aminoethyl) 4-methyl esters. DMAA refers to dimethyl acrylamide.

| Copolymer Name | Ester to DMAA ratio | Ester mass/mg | Ester amount/ mmol | DMAA mass/ mg | DMAA amount/ mmol | AIBN/mmol | AIBN mass/ mg |
|---|---|---|---|---|---|---|---|
| Methyl-co-DMAA 1 | 0.4/0.6 | 400 | 1.4 | 207 | 2.1 | 0.2 | 33.3 |

TABLE 1-continued

Reaction Parameters for the copolymerization of itaconic Acid 1-(N-Boc-aminoethyl) 4-alkyl ester with DMAA (Series 1). The target molecular mass was 3,000 g mol$^{-1}$. Methyl, Ethyl, Propyl and Butyl refer to the respective 1-(N-boc-aminoethyl) 4-methyl esters. DMAA refers to dimethyl acrylamide.

| Copolymer Name | Ester to DMAA ratio | Ester mass/mg | Ester amount/ mmol | DMAA mass/ mg | DMAA amount/ mmol | AIBN/mmol | AIBN mass/ mg |
|---|---|---|---|---|---|---|---|
| Methyl-co-DMAA 2 | 0.5/0.5 | 400 | 1.4 | 138 | 1.4 | 0.18 | 29.4 |
| Methyl-co-DMAA 3 | 0.6/0.4 | 400 | 1.4 | 92 | 0.9 | 0.16 | 26.3 |
| Ethyl-co-DMAA 1 | 0.4/0.6 | 400 | 1.3 | 179 | 2.0 | 0.20 | 32.5 |
| Ethyl-co-DMAA 2 | 0.5/0.5 | 400 | 1.3 | 132 | 1.3 | 0.17 | 28.6 |
| Ethyl-co-DMAA 3 | 0.6/0.4 | 400 | 1.3 | 88 | 0.9 | 0.16 | 26.7 |
| Propyl-co-DMAA 1 | 0.4/0.6 | 400 | 1.2 | 189 | 1.8 | 0.21 | 34.0 |
| Propyl-co-DMAA 2 | 0.5/0.5 | 400 | 1.2 | 126 | 1.2 | 0.12 | 27.2 |
| Propyl-co-DMAA 3 | 0.6/0.4 | 400 | 1.2 | 84 | 0.8 | 0.12 | 20.4 |
| Butyl-co-DMAA 1 | 0.4/0.6 | 400 | 1.2 | 181 | 1.8 | 0.19 | 31.5 |
| Butyl-co-DMAA 2 | 0.5/0.5 | 400 | 1.2 | 120 | 1.2 | 0.17 | 28.0 |
| Butyl-co-DMAA 3 | 0.6/0.4 | 400 | 1.2 | 80 | 0.8 | 0.16 | 25.9 |

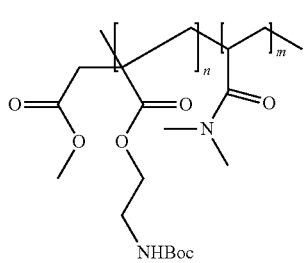

Poly[(1-(N-Boc-aminoethyl) 4-methyl diester)-co-DMAA]

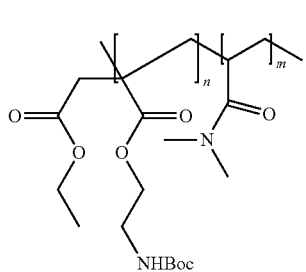

Poly[(1-(N-Boc-aminoethyl) 4-ethyl diester)-co-DMAA]

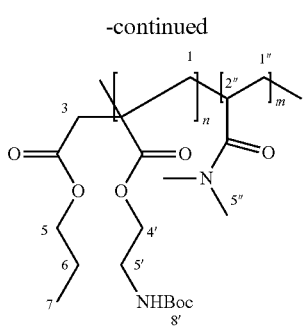

Poly[(1-(N-Boc-aminoethyl) 4-propyl diester)-co-DMAA]

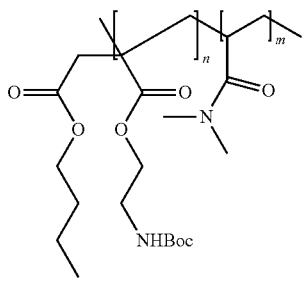

Poly[(1-(N-Boc-aminoethyl) 4-butyl diester)-co-DMAA]

Yields:

TABLE 2

Yields and GPC data obtained for the Copolymers of Series 1

| Copolymer | Ester to DMAA ratio | Yield/mg | Yield/% | $M_n$/ g mol$^{-1}$ | $M_w$/ g mol$^{-1}$ | PDI |
| --- | --- | --- | --- | --- | --- | --- |
| Methyl-co-DMAA 1 | 0.4/0.6 | 405 | 66 | 19.100 | 58.300 | 3.0 |
| Methyl-co-DMAA 2 | 0.5/0.5 | 88 | 16 | 11.900 | 31.900 | 2.6 |
| Methyl-co-DMAA 3 | 0.6/0.4 | 55 | 11 | 12.500 | 33.900 | 2.7 |
| Ethyl-co-DMAA 1 | 0.4/0.6 | 545 | 94 | 19.500 | 41.500 | 2.1 |
| Ethyl-co-DMAA 2 | 0.5/0.5 | 443 | 83 | 7.300 | 18.800 | 2.6 |
| Ethyl-co-DMAA 3 | 0.6/0.4 | 420 | 86 | 6.900 | 22.800 | 3.3 |
| Propyl-co-DMAA 1 | 0.4/0.6 | 550 | 93 | 11.200 | 29.000 | 2.5 |
| Propyl-co-DMAA 2 | 0.5/0.5 | 503 | 95 | 12.500 | 37.500 | 2.9 |
| Propyl-co-DMAA 3 | 0.6/0.4 | 464 | 95 | 6.600 | 23.700 | 3.5 |
| Butyl-co-DMAA 1 | 0.4/0.6 | 389 | 67 | 24.000 | 93.500 | 3.9 |
| Butyl-co-DMAA 2 | 0.5/0.5 | 156 | 30 | 17.700 | 51.400 | 2.8 |
| Butyl-co-DMAA 3 | 0.6/0.4 | 228 | 47 | 11.800 | 32.500 | 2.7 |

$^1$H-NMR of Propyl-co-DMAA 2 (250 MHz, CDCl$_3$): δ=4.01 (br. s, 4'-CH$_2$, 5-CH$_2$), 3.39 (br. s, 3-CH$_2$), 3.08 (br. s, 5"-CH$_3$), 2.23 (br. s, 1"-CH$_2$), 2.90 (br. s, 1-CH$_2$, 2"-CH), 1.70 (s, 6-CH$_2$), 1.46 (s, 8'-(CH$_3$)$_3$), 0.95 (br. s, 7-CH$_3$).

The position of the $^1$H-NMR spectra of the other polymers were similar and are therefore not listed here.

Series 2:

Copolymers of itaconic acid 1-(N-Boc-aminoethyl) 4-propyl ester were synthesized by adding 400 mg of the 1-(N-Boc-aminoethyl) 4-propyl ester monomer (1.4 mmol) to a heat-dried Schlenk tube under nitrogen. 126 mg (1.2 mmol) freshly purified dimethyl acrylamide (DMMA) was added using a syringe. Solvent (dimethyl sulfoxide, DMSO; or N,N-dimethylformamid, DMF) was added so that the monomer concentration given in Table 3 was obtained. The initiator azoisobutyric acid nitrile (AIBN, equivalents as specified)) was then added to the reaction mixture, and the reaction mixture was subject to three freeze-pump-thaw cycles. An oil bath was set to the reaction temperature of 70° C., and the reaction was allowed to proceed for the time specified in Table 3. The reaction mixture was then cooled and the reaction was quenched by stirring the open flask under ambient atmosphere. It was then added dropwise into cold hexane (100-150 mL) while stirring vigorously. The polymer precipitated. It was removed by filtration, washed with cold hexane and dried in dynamic vacuum. The yields are included in Table 3.

TABLE 3

Reaction Parameters for the copolymerization of itaconic Acid 1-(N-Boc-aminoethyl) 4-propyl diester with DMAA (Series 2). The target molecular mass ranged from 2,000 to 20,000 g mol$^{-1}$ and was adjusted by different amounts of the initiator AIBN and different reaction times.

| Copolymer name | Ester mass/ mg | Ester amount/ mmol | DMAA mass/ mg | DMAA amount/ mmol | Target molecular weight/ g mol$^{-1}$ | AIBN equivalents | AIBN mass/ mg |
| --- | --- | --- | --- | --- | --- | --- | --- |
| M 1600 | 400 | 1.4 | 126 | 1.2 | 2000 | 0.104 | 43.3 |
| M 4300 | 400 | 1.4 | 126 | 1.2 | 3000 | 0.069 | 27.2 |
| M 7200 | 400 | 1.4 | 126 | 1.2 | 3000 | 0.069 | 27.2 |
| M 12500 | 400 | 1.3 | 126 | 1.2 | 3000 | 0.069 | 27.2 |
| M 41000 | 400 | 1.3 | 126 | 1.2 | 20000 | 0.010 | 4.3 |

| Copolymer name | Concentration/ g mL$^{-1}$ | Reaction time/h | Yield/ mg | Yield/% | $M_n$/ g mol$^{-1}$ | $M_w$/ g mol$^{-1}$ | PDI |
| --- | --- | --- | --- | --- | --- | --- | --- |
| M 1600 | 0.05 | 8 | 246 | 44 | 1600 | 5300 | 3.4 |
| M 4300 | 0.1 | 16 | 490 | 83 | 4300 | 7300 | 1.6 |
| M 7200 | 0.25 | 16 | 380 | 72 | 7200 | 20400 | 2.8 |
| M 12500 | 0.5 | 22 | 503 | 95 | 12500 | 37500 | 2.9 |
| M 41000 | 1.0 | 24 | 498 | 94 | 41000 | 75300 | 1.8 |

Example 7

Homopolymer and Copolymer Deprotection

For deprotection, each polymer was dissolved in anhydrous methanol (methyl and ethyl homo- and copolymers) or chloroform (propyl or butyl homo- and copolymers). Typically, 1 mL solvent per 100 mg polymer was used. The reaction mixture was stirred, and HCl (4M in 1,4-dioxane, 1 mL per 100 mg polymer) was added. If the solution became turbid (homopolymers), methanol was added dropwise to clear the solution. The reaction was further stirred overnight. The solvent was removed using a rotary evaporator, the residue was taken up in methanol or chloroform, and the product was precipitated in hexane (100-150 mL). The polymers precipitated as a colorless powder and could be recovered by filtration or dekanting, and were dried in dynamic vacuum. The structure of the deprotected copolymers is shown below.

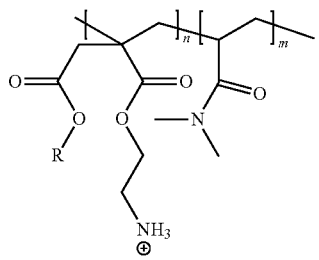

R = Methyl, Ethyl, Propyl, Butyl

Analytical Data:

$^1$H-NMR (250 MHz, CDCl$_3$): δ=8.63 (br. s., 1H), 4.01 (br. s., 1H), 2.92 (br. s., 7H), 2.20 (S, 1H), 1.99 (br. s., 4H), 1.66 (br. s., 3H), 1.28 (s, 2H), 0.95 (br. s., 3H). The spectra for the other alkyl residues and ratios were similar and are therefore not listed here.

Example 8

Figure 2:
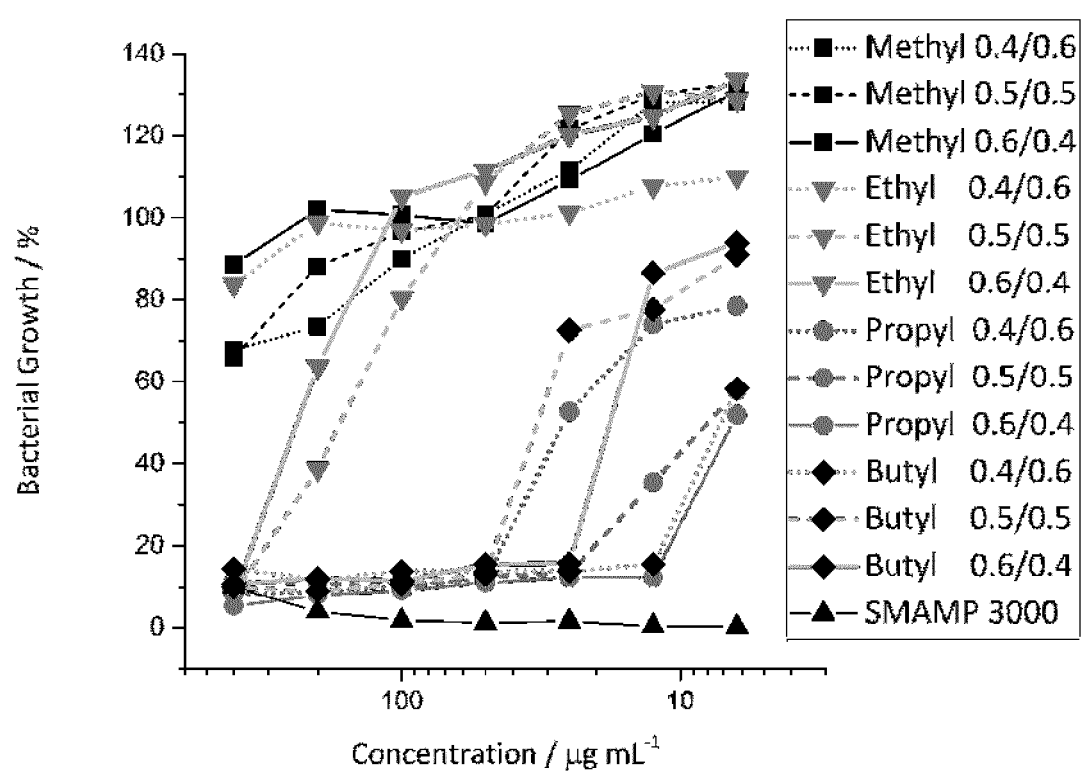
FIG. 2 shows the antimicrobial activity of Series 1 copolymers against *S. aureus* (cf. Example 8).

Antimicrobial Activities:

The antimicrobial activity was determined for the copolymers from series 1 and 2 against *Escherichia coli* (*E. coli*) and *Staphylococcus aureus* (*S. aureus*). The data is shown in FIGS. 1 and 2, and summarized in Tables 4 and 5.

TABLE 4

Minimum inhibitory concentration of Alkyl-co-DMAA Polymers against *E. coli*. For example Methly 0.4/0.6 refers to a Poly[(1-(ammoniumethyl) 4-methyl diester)-co-DMAA] copolymer with a monomer feed ratio of 0.4 equivalents itaconate monomer to 0.6 equivalents DMAA monomer. MIC$_{90}$ refers to the concentration where at least 90% of the bacteria are killed. The polymer with the lowest MIC$_{90}$ is the most active one. A Polyoxonorbornene SMAMP with Propyl residue and molecular weight 3000 g mol–1, as described in K. Lienkamp, A. E. Madkour, A. Musante, C. F. Nelson, K. Nusslein, G. N. Tew, *J. Am. Chem. Soc.* 2008, 130, 9836-9843, was used as reference.

| Copolymer | MIC$_{90}$/μg mL$^{-1}$ |
|---|---|
| Methyl 0.4/0.6 | >400 |
| Methyl 0.5/0.5 | >400 |
| Methyl 0.6/0.4 | >400 |
| Ethyl 0.4/0.6 | >400 |
| Ethyl 0.5/0.5 | >400 |
| Ethyl 0.6/0.4 | >400 |
| Propyl 0.4/0.6 | <100 |
| Propyl 0.5/0.5 | <50 |
| Propyl 0.6/0.4 | <50 |
| Butyl 0.4/0.6 | <12.5 |
| Butyl 0.5/0.5 | <12.5 |
| Butyl 0.6/0.4 | <12.5 |
| Poly(oxonorbornen)-SMAMP 3000 | <6.25 |

TABLE 5

Minimum inhibitory concentration of Alkyl-co-DMAA Polymers against *S. aureus*. For example Methly 0.4/0.6 refers to a Poly[(1-(ammoniumethyl) 4-methyl diester)-co-DMAA] copolymer with a monomer feed ratio of 0.4 equivalents itaconate monomer to 0.6 equivalents DMAA monomer. MIC$_{90}$ refers to the concentration where at least 90% of the bacteria are killed. The polymer with the lowest MIC$_{90}$ is the most active one. A Polyoxonorbornene SMAMP with Propyl residue and molecular weight 3000 g mol–1, as described in K. Lienkamp, A. E. Madkour, A. Musante, C. F. Nelson, K. Nusslein, G. N. Tew, *J. Am. Chem. Soc.* 2008, 130, 9836-9843, was used as reference.

| Copolymer | MIC$_{90}$/μg mL$^{-1}$ |
|---|---|
| Methyl 0.4/0.6 | >400 |
| Methyl 0.5/0.5 | >400 |
| Methyl 0.6/0.4 | >400 |
| Ethyl 0.4/0.6 | >400 |
| Ethyl 0.5/0.5 | <400 |
| Ethyl 0.6/0.4 | <400 |
| Propyl 0.4/0.6 | <50 |
| Propyl 0.5/0.5 | <25 |
| Propyl 0.6/0.4 | <12.5 |
| Butyl 0.4/0.6 | <12.5 |
| Butyl 0.5/0.5 | <50 |
| Butyl 0.6/0.4 | <25 |
| Poly(oxonorbornen)-SMAMP 3000 | <6.25 |

The invention claimed is:

1. A polymer, comprising a repeat unit A having a general formula selected from one of the following general formulae (I-a), (I-b), (I-c), (I-d), (I-e) and (I-f):

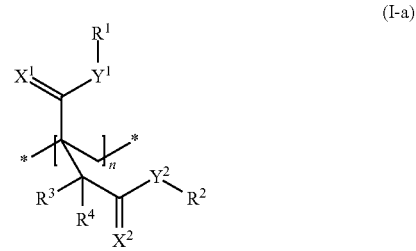

(I-a)

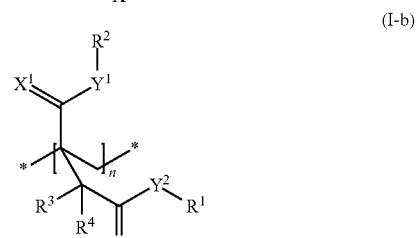

(I-b)

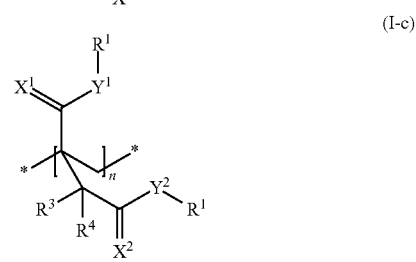

(I-c)

-continued

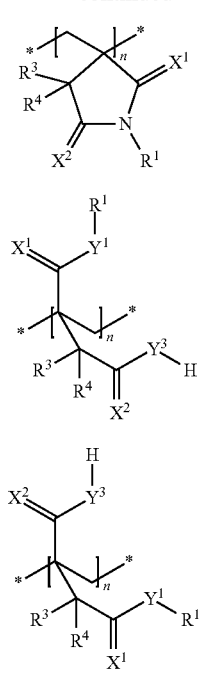

(I-d)

(I-e)

(I-f)

wherein
R$^1$ is an optionally substituted organic residue that comprises at least one cationic moiety having at least one positive charge;
R$^2$ is an optionally substituted organic residue;
R$^3$ and R$^4$ are selected independently of each other from H and an optionally substituted organic residue;
X$^1$ and X$^2$ are selected independently of each other from O and S;
Y$^1$ and Y$^2$ are selected independently of each other from O, S, NH, NR$^5$ and PR$^5$,
wherein R$^5$ is C$_1$ to C$_{12}$ alkyl;
Y$^3$ is selected from O and S; and
n is from 2 to 4500.

2. The polymer according to claim 1, wherein R$^1$ and R$^2$ are selected independently of each other from an optionally substituted residue selected from the group consisting of linear or branched C$_1$ to C$_{30}$ alkyl, linear or branched C$_2$ to C$_{30}$ alkenyl, linear or branched C$_2$ to C$_{30}$ alkynyl, linear or branched C$_1$ to C$_{30}$ heteroalkyl, linear or branched C$_2$ to C$_{30}$ heteroalkenyl, linear or branched C$_2$ to C$_{30}$ heteroalkynyl, C$_3$ to C$_{30}$ cycloalkyl, C$_4$ to C$_{30}$ cycloalkenyl, C$_5$ to C$_{30}$ cycloalkynyl, C$_6$ to C$_{30}$ aryl, C$_3$ to C$_{30}$ heterocycloalkyl, C$_4$ to C$_{30}$ heterocycloalkenyl, C$_5$ to C$_{30}$ heterocycloalkynyl, C$_6$ to C$_{30}$ aryl, linear or branched C$_7$ to C$_{30}$ arylalkyl, C$_5$ to C$_{30}$ heteroaryl, and linear or branched C$_6$ to C$_{30}$ heteroarylalkyl.

3. The polymer according to claim 1, wherein R$^2$ is selected from the group consisting of C$_1$ to C$_{12}$ alkyl, C$_3$ to C$_{12}$ cycloalkyl, C$_1$ to C$_{12}$ heteroalkyl, C$_5$ to C$_{12}$ heterocycloalkyl, C$_6$ to C$_{12}$ aryl and C$_5$ to C$_{12}$ heteroaryl.

4. The polymer according to claim 1, wherein R$^3$ and R$^4$ are selected independently of each other from the group consisting of H, C$_1$ to C$_{12}$ alkyl, C$_3$ to C$_{12}$ cycloalkyl, C$_1$ to C$_{12}$ heteroalkyl, C$_5$ to C$_{12}$ heterocycloalkyl, C$_6$ to C$_{12}$ aryl and C$_5$ to C$_{12}$ heteroaryl.

5. The polymer according to claim 1, wherein R$^1$ is a C$_1$ to C$_{30}$ heteroalkyl, C$_1$ to C$_{30}$ heteroalkenyl, C$_1$ to C$_{30}$ heteroalkynyl, C$_3$ to C$_{30}$ heterocycloalkyl, C$_4$ to C$_{30}$ heterocycloalkenyl, C$_5$ to C$_{30}$ heterocycloalkynyl, C$_1$ to C$_{30}$ heteroaryl, or C$_1$ to C$_{30}$ heteroarylalkyl selected from the group consisting of residues having the general formula (II), (III), (IV), (V) or (VI):

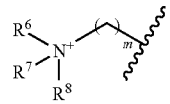

(II)

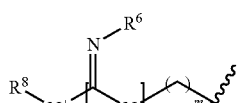

(III)

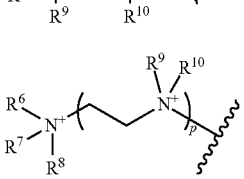

(IV)

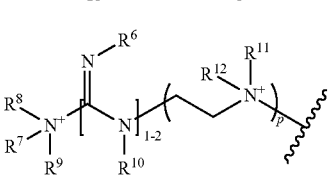

(V)

wherein
R$^6$, R$^7$, R$^8$, R$^9$, R$^{10}$, R$^{11}$ and R$^{12}$ are selected independently from each other from the group consisting of H, C$_1$ to C$_{12}$ alkyl, C$_2$ to C$_{12}$ alkenyl, C$_2$ to C$_{12}$ alkynyl, C$_3$ to C$_{12}$ cycloalkyl, C$_4$ to C$_{12}$ cycloalkenyl, C$_5$ to C$_{12}$ cycloalkynyl, C$_6$ to C$_{12}$ aryl, C$_7$ to C$_{12}$ arylalkyl, C$_1$ to C$_{12}$ heteroalkyl, C$_2$ to C$_{12}$ heteroalkenyl, C$_2$ to C$_{12}$ heteroalkynyl, C$_3$ to C$_{12}$ heterocycloalkyl, C$_4$ to C$_{12}$ heterocycloalkenyl, C$_5$ to C$_{12}$ heteroaryl, and C$_6$ to C$_{12}$ heteroarylalkyl;
m is an integer selected from 0 to 12; and
p is an integer selected from 1 to 12;

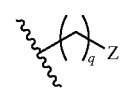

(VI)

wherein
Z is selected from azolium ions or salts, imidazolium ions or salts, pyrazolium ions or salts, triazolium ions or salts, tetrazolium ions or salts, pyridinium ions or salts, pyrimidinium ions or salts, triazininum ions or salts, tetrazinium ions or salts, azepinium ions or salts, diazepinium ions or salts, thiazolium ions or salts, thiadiazolium ions or salts, thiazinium ions or salts, oxazolium ions or salts, oxadiazolium ions or salts, azirinidium ions or salts, azirinium ions or salts, azetidinium ions or salts, pyrrolidinium ions or salts, pyrrolidinium ions or salts, piperidinium ions or salts, azepanium ion or salts, imidazolinium ions or salts, purinium ions or salts, sulfonium ions or salts, phosphonium ions or salts, guanidinium ions or salts, biguanidinium ions or salts, polyguanidinium ions or salts, and combinations thereof; and
q is an integer selected from 0 to 12.

6. The polymer according to claim 1, which comprises a repeat unit A represented by general formula (I-a) or (I-b), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, $R^2$ is an unsubstituted $C_1$ to $C_{12}$ alkyl; both $R^3$ and $R^4$ are H; and each of $X^1$, $X^2$, $Y^1$ and $Y^2$ is O.

7. The polymer according to claim 1, which comprises a repeat unit A represented by general formula (I-c), wherein both $R^1$ are a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.

8. The polymer according to claim 1, which comprises a repeat unit A represented by general formula (I-d), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.

9. The polymer according to claim 1, which comprises a repeat unit A represented by one of general formulae (I-e) or (I-f), wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, both $R^3$ and $R^4$ are H; and each of $X^1$, $X^2$, $Y^1$ and $Y^2$ is O.

10. The polymer according to claim 1, which consists of repeat units A only.

11. The polymer according to claim 10, wherein $R^1$ is a residue having the general formula (II) or (III) with m being 1 or 2, preferably with $R^6$, $R^7$, $R^8$, $R^9$ and $R^{10}$ being H or $C_1$ to $C_4$ alkyl, $R^2$, if present, is an unsubstituted $C_1$ to $C_{12}$ alkyl, both $R^3$ and $R^4$ are H, and each of $X^1$, $X^2$, $Y^1$ and $Y^2$ is O.

12. The polymer according to claim 1, wherein the polymer comprises at least one further repeat unit B which is derived from a monomer compound selected from the group consisting of vinyl ether, styrene or styrene derivatives, N-vinylpyrrolidone, vinyl chloride, vinyl acetate, vinylpyridine, vinylpyridinium ions or salts, a compound having general formula (VII), a compound having general formula (VIII), and itaconic acid, its sulfur containing analogues and its derivatives, as long as the respective repeat unit B is not a repeat unit A represented by one of general formulae (I-a), (I-b), (I-c), (I-d), (I-e) and (I-f):

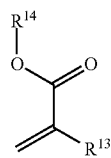

(VII)

wherein
$R^{13}$ is selected from H and $C_1$ to $C_{12}$ alkyl; and
$R^{14}$ is selected from the group consisting of H and an organic residue selected from $C_1$ to $C_{12}$ alkyl and $C_1$ to $C_{12}$ heteroalkyl;

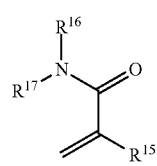

(VIII)

wherein
$R^{15}$ is selected from the group consisting of H and $C_1$ to $C_{12}$ alkyl; and
$R^{16}$ and $R^{17}$ are selected independently from each other from the group consisting of H and an organic residue selected from $C_1$ to $C_{12}$ alkyl and $C_1$ to $C_{12}$ heteroalkyl.

13. The polymer according to claim 12, wherein the repeat unit B is based on styrene or on a compound having general formula (VIII) with $R^{16}$ and $R^{17}$ selected from linear $C_1$ to $C_4$ alkyl, —$CH_2OH$, —$CH_2CH_2OH$ or isopropyl, and the repeat unit A is represented by general formula (I-a) or (I-b), wherein IV is a residue having the general formula (II) or (III) with m being 1 or 2, and all of $R^6$, $R^7$, $R^8$, $R^9$ and $R^{10}$ being identically H or $C_1$ to $C_4$ alkyl, $R^2$ is an unsubstituted $C_1$ to $C_4$ alkyl, both $R^3$ and $R^4$ are H, and each of $X^1$, $X^2$, $Y^1$ and $Y^2$ is O.

14. The polymer according to claim 12, wherein the different versions of repeat unit A are referred to as $A_i$, and wherein the molar fractions of the different repeat units $A_i$ are referred to as $r_i$, and r is defined as the sum of all the respective molar fractions $r_i$ d($r=\Sigma r_i$), and wherein the different versions of repeat unit B are referred to as $B_i$, and wherein the molar fractions of the different repeat units $B_i$ are referred to as $s_i$, and s is defined as the sum of all the respective molar fractions $s_i$ ($s=\Sigma s_i$), and r=0.01 to 0.99, preferably 0.4 to 0.6, more preferably 0.5, and s=0.01 to 0.99, preferably 0.4 to 0.6, more preferably 0.5, and r+s=1 for each combination.

15. The polymer according to claim 1, wherein the polymer comprises at least one further repeat unit C, which comprises a crosslinking moiety, preferably selected from a photo-crosslinking moiety and a thermally activated crosslinking moiety.

16. The polymer according to claim 15, wherein the polymer comprises at least one further repeat unit C, which is derived from a monomer compound having the general formula (IX):

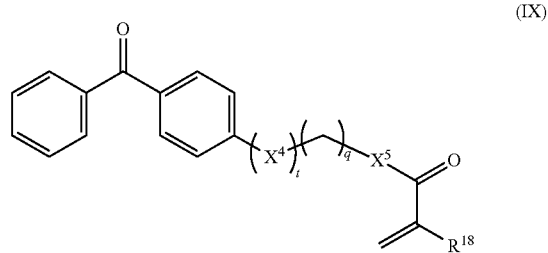

(IX)

wherein
$R^{18}$ is independently selected from H or an organic residue selected from $C_1$ to $C_{12}$ alkyl, $C_2$ to $C_{12}$ alkenyl, $C_2$ to $C_{12}$ alkynyl, $C_3$ to $C_{12}$ cycloalkyl, and $C_6$ to $C_{12}$ aryl;

$X^4$ is selected from —O—, —S—, —NH—, —NR—, NR'—, —C(=O)—, —C(=S)—, —O—C(=O)—, —C(=O)—O—, —NH—C(=O)—, —NR—C(=O)—, —C(=O)—NH—, —C(=O)—NR—, —O—C(=O)—O—, —NH—C(=O)—NH—, —NR—C(=O)—NR—, —NH—C=NH—NH—, —NH—C=NR—NH, —NR—C=NH—NR—, and —NR—C═NR—NR—, wherein R represents a $C_1$ to $C_{30}$ alkyl residue and R' represents a $C_1$ to $C_{30}$ heteroalkyl residue;

$X^5$ is selected from —O—, —NH—, and —NR—, wherein R represents a $C_1$ to $C_{30}$ alkyl residue;

q is an integer of from 0 (zero) to 12; and t is 0 (zero) or 1.

17. The polymer according to claim 15, wherein the at least one repeat unit C is comprised in the polymer of the present invention in a ratio of up to 20%.

18. The polymer according to claim 1, wherein the total number of all repeat units A, optional repeat units B, and optional repeat units C in the polymer is from 2 to 4500.

19. The polymer according to claim 1, wherein the polymer has a number average molecular weight $M_n$ of from 220 to 1,000,000 g/mol.

20. Use of the polymer according to claim 1 for preventing microbial growth, and/or microbial adhesion, and/or protein adhesion, and/or biofouling, and/or biofilm formation by microbes or other organisms.

21. A compound represented by one of general formulae (X-a), (X-b), (X-c), (X-d), (X-e), and (X-f):

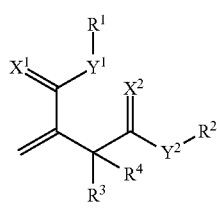
(X-a)

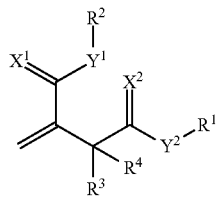
(X-b)

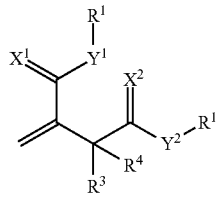
(X-c)

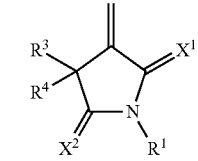
(X-d)

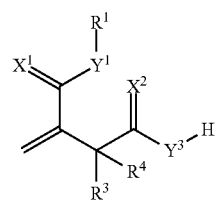
(X-e)

-continued

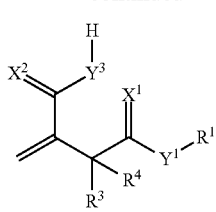
(X-f)

wherein $R^1$, $R^2$, $R^3$, $R^4$, $X^1$, $X^2$, $Y^1$, $Y^2$ and $Y^3$ are defined as for general formulae (I-a), (I-b), (I-c), (I-d), (I-e) and (I-f).

22. The compound according to claim 21, wherein $R^1$ is represented by a general formula selected from general formulae (II-P), (III-P), (IV-P) and (IV-P):

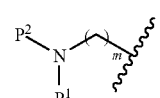
(II-P)

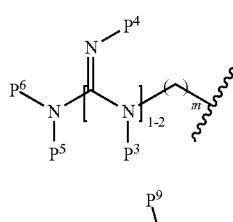
(III-P)

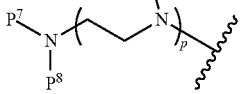
(IV-P)

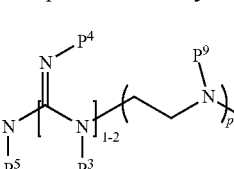
(V-P)

wherein m and p are as defined for formulae (II) and (III), and (IV) and (V), respectively, and $P^1$, $P^2$, $P^3$, $P^4$, $P^5$, $P^6$, $P^7$, $P^8$ and $P^9$ each represent, independently of each other, H, $C_1$ to $C_6$ alkyl or a suitable protective group, preferably selected from a tert-butyloxycarbonyl (Boc) group, a 9-fluorenylmethyloxycarbonyl (FMOC) group, and a carbamate group, or wherein $P^1$ and $P^2$, or $P^5$ and $P^6$, or $P^7$ and $P^8$, respectively, are linked and form a protective group, preferably a phthalimide group.

23. A composition, comprising the polymer according to claim 1.

24. The composition according to claim 23, wherein the composition is a solution, preferably an aqueous solution or a non-aqueous solution, an emulsion, preferably a lipid emulsion or an O/W or W/O emulsion, or a formulation, a paste, a lotion, a cream or a gel.

25. Use of the composition according to claim 23 as a medical preparation for treating or preventing microbial infections in a patient.

26. Use of the composition according to claim 23 for preventing microbial growth on a substrate, device or tool.

27. A medical formulation, comprising the polymer according to claim 1.

28. A substrate impregnated or coated with the polymer according to claim 1.

29. The polymer according to claim 1, wherein the polymer is bound to a surface of a substrate via a non-covalent or a covalent bond.

30. A method of coating a substrate with a polymer, comprising the steps of:
   a) optionally pretreating a surface of a substrate to comprise oxide or hydroxide groups, or other groups known to the skilled expert to react with a reactive silane;
   b) functionalizing the optionally pretreated surface by covalently binding a reactive silane, thiol or disulfide compound comprising a photo-reactive crosslinker to the pretreated surface as obtained according to step a);
   c) coating the surface with the polymer according to claim 1, optionally adding an external photo-crosslinker, onto the surface as obtained according to step b),
   d) irradiating the surface comprising the photo-reactive surface crosslinker and the optionally present external photo-crosslinker with UV light, thereby covalently binding the optionally protected polymer to a photo-reactive group of the photo-reactive surface crosslinker, thereby covalently binding the polymer to the surface and optionally crosslinking it to a surface attached network,
   e) optionally carrying out a post-irradiaton treatment of the covalently bound polymer as obtained by step d) by deprotection, or carrying out washing steps.

31. A method of coating a substrate with a polymer, comprising the steps of:
   a) optionally pretreating a surface of a substrate to comprise oxide or hydroxide groups, or other groups known to the skilled expert to react with a reactive silane;
   b) functionalizing the optionally pretreated surface by covalently binding a reactive silane, thiol or disulfide compound comprising a thermo-reactive crosslinker to the pretreated surface as obtained according to step a);
   c) coating the surface with the polymer according to claim 1, optionally adding an external thermo-crosslinker, onto the surface as obtained according to step b),
   d) heating the surface comprising the thermo-reactive surface crosslinker and the optionally present external thermo-crosslinker, thereby covalently binding the optionally protected polymer to a thermo-reactive group of the thermo-reactive surface crosslinker, thereby covalently binding the polymer to the surface and optionally crosslinking it to a surface attached network,
   e) optionally carrying out a post-irradiaton treatment of the covalently bound polymer as obtained by step d) by deprotection, or carrying out washing steps.

32. A method of coating a substrate with a polymer, comprising the steps of:
   a) optionally pretreating a surface of a substrate to comprise oxide or hydroxide groups, or other groups known to the skilled expert to react with a reactive silane;
   b) functionalizing the optionally pretreated surface by covalently binding a reactive silane, thiol or disulfide compound comprising a photo-reactive crosslinker to the pretreated surface as obtained according to step a);
   c) coating the surface with the polymer according to claim 1, adding an external thermo-crosslinker, onto the surface as obtained according to step b),
   d) irradiating the surface comprising the photo-reactive surface crosslinker with UV light, thereby covalently binding the optionally protected polymer to a photo-reactive group of the photo-reactive surface crosslinker, thereby covalently binding the polymer to the surface, and heating the external thermo-crosslinker, thereby crosslinking the polymer to a surface attached polymer network,
   e) optionally carrying out a post-irradiaton treatment of the covalently bound polymer as obtained by step d) by deprotection, or carrying out washing steps.

33. A substrate coated with a polymer, said substrate being obtained by the method according to claim 30.

34. The substrate according to claim 28, wherein the polymer coating has a thickness of from 10 nm to 1000 μm.

35. A medical formulation, comprising the composition according to claim 23.

36. A substrate impregnated or coated with the composition according to claim 23.

* * * * *